United States Patent [19]

Knauf et al.

[11] Patent Number: 5,981,839
[45] Date of Patent: *Nov. 9, 1999

[54] METHODS AND COMPOSITIONS FOR REGULATED TRANSCRIPTION AND EXPRESSION OF HETEROLOGOUS GENES

[75] Inventors: Vic C. Knauf, Winters; Jean C. Kridl, Davis, both of Calif.

[73] Assignee: Calgene, LLC, Davis, Calif.

[ * ] Notice: This patent is subject to a terminal disclaimer.

[21] Appl. No.: 08/812,665

[22] Filed: Mar. 7, 1997

Related U.S. Application Data

[63] Continuation of application No. 08/484,941, Jun. 7, 1995, Pat. No. 5,750,385, which is a continuation of application No. 08/105,852, Aug. 10, 1993, Pat. No. 5,753,475, which is a continuation-in-part of application No. 07/526,123, May 21, 1990, which is a continuation of application No. 07/267,865, Nov. 2, 1988, abandoned, which is a continuation of application No. 06/692,605, Jan. 17, 1985, abandoned, said application No. 08/105,852, is a continuation-in-part of application No. 07/582,241, Sep. 14, 1990, abandoned, which is a continuation of application No. 07/188,361, Apr. 29, 1988, abandoned, which is a continuation-in-part of application No. 07/168,190, Mar. 15, 1988, abandoned, which is a continuation-in-part of application No. 07/054,369, May 26, 1987, Pat. No. 4,943,674, said application No. 08/105,852, is a continuation-in-part of application No. 07/742,834, Aug. 8, 1991, Pat. No. 5,420,034, which is a continuation of application No. 07/550,804, Jul. 9, 1990, abandoned, which is a continuation of application No. 07/147,781, Jan. 25, 1988, abandoned, which is a continuation-in-part of application No. 07/078,538, Jul. 28, 1987, abandoned, which is a continuation-in-part of application No. 06/891,529, Jul. 31, 1986, abandoned.

[51] Int. Cl.[6] .............................. A01H 5/00; A01H 5/10; C12N 5/04; C12N 15/82

[52] U.S. Cl. ..................... 800/287; 800/286; 800/294; 800/298; 800/306; 800/312; 800/314; 800/320; 800/322; 435/69.1; 435/70.1; 435/183; 435/419; 435/415; 435/416; 435/468; 435/469; 536/23.6; 536/24.1; 536/24.5

[58] Field of Search .................... 536/23.6, 24.1, 536/24.5; 800/205, 250, 255, DIG. 15–17, 11, 14, 26, 27, 55–58, 278, 286, 287, 294, 298, 306, 312, 314, 320, 322; 435/69.1, 172.3, 415, 419, 416, 70.1, 183, 468, 469

[56] References Cited

U.S. PATENT DOCUMENTS 5,420,034  5/1995  Kridl et al. ............................ 435/419
5,504,200  4/1996  Hall et al. ............................. 536/24.1

OTHER PUBLICATIONS

DeBlock et al. 1984. EMBO J. 3(8):1681–1689.

Horsch et al. 1984. Science 223:496–498.

Pedersen et al. 1983. Plant Cell Reports 2:201–204.

Sengupta–Gopalan et al. 1985. Proc. Natl. Acad. Sci. USA 82:3320–3324.

Zambryski et al. 1983. EMBO J. 2(12):2143–2150.

*Primary Examiner*—David T. Fox
*Attorney, Agent, or Firm*—Barbara Rae-Venter; Rae-Venter Law Group P.C.

[57] ABSTRACT

Regulatory regions from genes expressed during a particular developmental stage or in a specific tissue are identified employing cDNA screening. The resulting regulatory regions are manipulated for use with foreign sequences for introduction into plant cells to provide transformed plants having phenotypic property which can be modulated. The invention is exemplified with light, seed and fruit-specific promoters.

16 Claims, 44 Drawing Sheets pGN1

```
                                                        HindIII
                                                          AluI                TaqI
    TaqI                                                  | |                  | |
    | |                                                    52                  66
     3                                                     50                                              69
  1 GTCGAGGCAGTCACTAACATGAAGTTTGACGAGGAGCCCAACTATGGGAAGCTTATTTCTCTTTTCGAT SacI
              HhaI XbaI                                    AluI
               | | | |                                    | |
                89  95                                    119
                                                          121                                             138
 70 ACTCTAATTGAGCCGTGCGCTCTATCTAGACCAATTAGAATTGATGGAGCTCTAAAGGTTGCTGGCTGT NdeI
               | |                                                                                      NdeI
               150                                                                                       | |
                                                                                                         206                  207
139 TTTCTTGTTTCATATGATTAACTTCTAAACTTGTGTATAAATATTCTCTGAAAGTGCTTCTTTTGGCATA 276
208 TGTAGGTTGGGCAAAAACGAGGAAGATTGCTTCTCAATTTGGAAGATGATGAACAGCCGAAGAAGAAAA Sau3AI
     DdeI
     | |
     309                                                                                                                      345
277 TAAGAATAGGCAGTCCTGCTACTCAATGATCTCAGTCTATAACGGTCGTCGTCCCATGAAACAGAGGT
     305
```

FIG. 1A

SacI

|       | AluI                                                                  | AluI |
|-------|-----------------------------------------------------------------------|------|
| 691   | TACTATATAAGCTCCATAGCGGGGTTCAGATAACGGGGAGCTCTTTAGTTGTTATGTCAAAAGGTTAGTGT | 759  |
|       | 702                                                                   | 729  |
|       |                                                                       | 731  |

760 TTAGTGAATAATAAACTTATTATATCAAAAAGTCTTCATTGACTTATTTATATACTTGTTGTGAATTGGTA 828

DdeI                    HinfI
829 GGAACTACTACTTATTCTCAGCAGTCATACAAAGTGAGTGACTCATTTCCATTCAAGTGGATAAATAAGAAA 897
                843                              866

XmnI                                                    TaqI
898 TGGAAAGAAGATTTTCATGTAACCTCCATGACAACTGCTGGTAATCGTTGGGGTGTGGTAATGTCGAGG 966
           909                                                     962

Sau3AI
BclI
982
982

967 AACTCTGGCTTCTCTCTGATCAGGTAGGTTTTTGTCTCTTATTGTCTGGTGTTTTATTTCCCCTGATAG 1035

AluI        RsaI
1036 TCTAATATGATAAACTCTGCGTTGTGAAAGGTGGTGGAGCTTGACTTTTTGTACCCAAGCGATGGGATA 1104
                                                 1075        1088

FIG. 1C

```
Lambda CGNI-2

NCG-I86 Linear          Length = 4325

XhoI
     TaqI                                      HindIII
     AvaI                                      AluI        TaqI
     ¦¦¦                                       ¦ ¦         ¦ ¦
CTCGAGGCAGTCACTAACATGAAGTTTGACGAGGAGCCCAACTATGGGAAGCTTATTTCTCTTTTCGAT    69
2                                                 52          66
3                                                 50

SacI
                HhaI XbaI         AluI
                ¦  ¦ ¦ ¦          ¦ ¦
ACTCTAATTGAGCCGTGCGCTCTATCTAGACCAATTAGAATTGATGGAGCTCTAAAGGTTGCTGGCTGT   138
                89  95                   119
                                             121

NdeI                                                                 NdeI
   ¦  ¦                                                                 ¦  ¦
TTTCTTGTTCATATGATTAACTTCTAAACTTGTGTATAAATATTCTCTGAAAGTGCTTCTTTTGGCATA   207
   150                                                             206

TGTAGGTTGGGCAAAAACGAGGAAGATTGCTTCTCAATTTGGAAGAGGATGAACAGCCGAAGAAGAAAA   276

Sau3AI
           DdeI
           ¦  ¦
TAAGAATAGGCAGTCCTGCTACTCAATGGATCTCAGTCTCTATAACGGTCGTCGTCCCATGAAACAGAGGT 345
              309
           305

EcoRV
                                                   ¦   ¦
AAAACATTTTTTGCATATACACTTTGAAAGTTCCTCACTAACTGTGTAATCTTTTTGGTAGATATCACTA   414
                                                    408
```

FIGURE 2A

```
                          AluI            Sau3AI                          DdeI
                           |                |                              |
CTCATGTCAAGGTTGGTTTCTTTAGCTTTGAACACAGATTTGGATCTTTTTGTTTTGTTTCCATATACT   1311
                          1268             1285                           1311

DdeI
      |
  AvaI AluI                                         HinfI    RsaI
   |   |                                              |       |
TAGGACCTGAGAGCTTTTGGTTGATTTTTTTTTCAGGACAAATGGGCGAAGAATCTGTACATTGCATCA   1380
1315 1325                                            1363   1370
1319

ATATGCTATGGCAGGACAGTGTGCTGATACACACTTAAGCATCATGTGAAAGCCAAAGACAATTGGAG   1449

HinfI
    DdeI
    | |                                    RsaI
CGAGACTCAGGGTCGTCATAATACCAATCAAAGACGTAAACCAGACGCAACCTCTTTGGTTGAATGTA   1518
   1456                                    1548
   1454

EcoRV
                                                              |
ATGAAAGGGATGTGTCTTGGTATGTATGTACGAATAACAAAAGAGAAGATGGAATTAGTAGTAGAAATA   1587

AluI
           |
TTTGGGAGCTTTTTAAGCCCTTCAAGTGTCTTTTTATCTTATTGATATCATCCATTTGCGTTGTTTAA   1656
          1596                                       1635

XbaI                      DdeI
    |                          |
TGCGTCTCTAGATATGTTCCTATATCTTCTCAGTGTCTGATAAGTGAAATGTGAGAAAACCATACCAA   1725
   1664                       1687
```

FIGURE 2D

Brassica campestris ACP Genomic Sequence

```
                          AccI
                           |
  1 AAGAGTATGTCTACTACTACTACTCTATAATCAAGTTTCAAGAAGCTGAGCTTGGCTCTCACTTTATAT   69
                    11                              DdeI
                                                 AluI AluI
                                                  |   |
                                                 46   51
                                                  47

DdeI
                                      |
 70 GTTTGATGTGTTGTGTGCAGGTATGGTAAATCATGGAAAGAGATAAAGAATGCAAACCCTGAAGTATTGG  138

RsaI
               |
139 CAGAGAGGACTGAGGTGAGAGAGCATGTCACTTTTGTGTTACTCATCTGAATTATCTTATATGCGAATT  207
                 149                                  217

208 GTAAGTGGTACTAAAAGGTTTGTAACTTTTGGTAGGTGGATTTGAAGGATAAATGGAGGAACTTGCTTC  276

HindIII                   PvuII
                                           AluI                     AluI
                                            |                        |
277 GGTAGCGGTAACAAGTTTTATATTGCTATGAAGCTTTTTGCCTGCGTGACGTATCAGCAGCTGTGGAG  345
                                         308                        338
                                             310                     338
```

FIGURE 3A

```
                                                                          MspI
                                                                          HpaII
                                                                          HaeIII
                                                                            ||
346  AAGATGGTATTAGAAAGGGTCTTTTCACATTTTGTGTTGTGACAAATATTAATTCGGCCGGTATGGTTT   414
                                                                            403
                                                                            404
                                                                            404

415  GGTTAAGACTTGTTGAGAGACGTGTGGGGTTTTTTGATGTATAATTAGTCTGTGTTTAGAACGAAACAA   483

Tth111I
                                                                     |
484  GACTTGTGTGNGTATGCTTTTTTTTAACTTGAGGGGGTTTGTTGTGTTAGTTAGGAACTTGACTTTGTCT   552
                                                                         547

Sau3AI                             ScaI
             BglII                              RsaI
               |                                  |
553  CTTTCTCTCAAGATCTGATTGGTAAGGTCTCGGGTGGTAGTACTGTTTGGTTTAATTTGTTTTGACTATT   621
               564                              593
               564                              593

HpaII
     HinfI  HaeIII        DraI                             DraI MspI DdeI
       |     |              |                               |    |    |
622  GAGTCACTGTGGCCCATTGACTTTAAATTAGGCTGGTATATTTTTTGGTTTAAAACCGGTCTGAGATAG   690
      623   634             646                            673  678  683
                                                                678

FIGURE 3B
```

```
                                                           HindIII                    AluI AvaI
                                  HaeIII                     AluI                      |   |       1035
                                   |                          |                  AGCCAGCTACCTC
 967 AAGGCCCATGTTATCATAAAACGCCCGTCGTTTGAGTGCACCAAGCTTATAAATGT               1029 1034
                                                             1012
                                                             1010

XhoI
                                                    TaqI Sau3AI
                                RsaI                AvaI BglIII    AvaI           TaqI
                                 |                   |||           |               |     1104
1036 GGGACATCACGCTCTTTGTACACTCCGCCATCTCTCCTCTCTCTCGAGCAGATCTCTCTCTCGGGAATATCG  1103
                                  1055                       1078 1085         1093
                                                             1079 1085
                                                             1078

Tth111I
     TaqI
     SalI
     HincII
     AccI
     ||||                                                                                1173
1105 ACAATGTCGACCACTTTCTGCTCTTCCGTCTCCATGCAAGCCACTTCTCTGGTAATCTCATCTCCTTCT
     1108 METSerThrPheCysSerSerValSerMETGlnAlaThrSerLeu
     1110
     1111
     1112
     1112
```

FIGURE 3D

```
                                                    HhaI              DdeI
1519 TCCTTCAACCTCGCCGTTCAATCCCCACTCGTTCTCAATCTCCTGCGCGGTATGTTCTCATTCTCAG 1587
     SerPheAsnLeuArgSerIleProThrArgPheSerIleSerCysAla
           TaqI            AluI          RsaI        1568                 1584
                                                              HaeIII
1588 CATTTATTTCGAGCTTGCTGTCATGGTACTCTCTCTAATTGTCTATTTGGTTTATTAGGCCAAACCAG 1656
                                                                   AlaLysProG
     1597           1601              1616                              1648
                           DdeI                        AluI
1657 AGACGGTTGAGAAAGTGTCTAAGATAGTTAAGAAGCAGCTATCACTCAAAGACGACCAAAAGGTCGTTG 1725
     luThrValGluLysValSerLysIleValLysLysGlnLeuSerLeuLysAspAspGlnLysValValA
                                                          1695
                    Sau3AI      HinfI  TaqI
1726 CGGAGACCAAGTTTGCTGATCTTGGAGCAGATTCTCTCGACACTGTAAGTCATCAATCATTCTCTTATG 1794
     laGluThrLysPheAlaAspLeuGlyAlaAspSerLeuAspThr
                                       1743       1756   1763
                                                     DdeI                SphI
1795 TGAATAAAGAGAACTTGAAGAGTTTGTTTTTAACATATTAACTGAGTGTTTGCATGCAGGTTGAGATA 1863
                                                                       ValGluIle
                                               1837                 1852
```

FIGURE 3F

Brassica Campestris Seed Specific cDNA-EA9

```
                    Sau3AI
                    |
1   TTCAACTTTTCTAAACCAAATGGCTTTAACACAGATCCAAATCTTTCTCATTGTCTCTCTAGTCTCATC    69
                      METAlaLeuThrGlnIleGlnIleIlePheLeuIleValSerLeuValSerSe
                                  34

TaqI
    Sau3AI                                    TaqI
    ClaI                                      |
    | |
70  ATTCAGTTTATGATCACTCTTTCTCGTCCATTACTCGATGAAGTCGCCATGCAAAAGAGACATGCCGA    138
    rPheSerLeuSerIleThrLeuSerArgProLeuLeuAspGluValAlaMETGlnLysArgHisAlaGl
        81                                       106
         82
         81

HaeIII
                                                |
139 GTGGATGACCGAAACACGGCCGTGTTTACGCAGATGCGAACGAGAAAAACAACCGCTACGCTGTTTCAA    207
    uTrpMETThrGluHisGlyArgValTyrAlaAspAlaAsnGluLysAsnAsnArgTyrAlaValPheLy
                                       157
```

Complete nucleotide sequence of B. campestris cDNA EA9. The longest open reading frame is designated by three letter amino acid code. PolyA tails are evident at the end of the sequence and a potential polyadenylation signal is underlined.

FIGURE 4A

```
         PvuII
         AluI
         |
    484  TTCAGCTGTTGCGGCTATAGAAGGAGTAGCACAGATAAAGAAAGGGAAACTCATTTCTTTGTCTGAACA   552
         eSerAlaValAlaAlaIleGluGlyValAlaGlnIleLysLysGlyLysLysLeuIleSerLeuSerGluGl
         489
         489

TaqI
              SalI
              HincII
              AluI AccI
              |   | | |
    553  AGAGCTTGTCGACTGCGACACAAACGATGGTGGCTGCATGGGCGGTTTGATGGATACAGGTTTAACTA   621
         nGluLeuValAspCysAspThrAsnAspGlyGlyCysMETGlyGlyLeuMETAspThrAlaPheAsnTy
         557  562
              560
              561
              562

622  CACAATAACTATTGGCGGCTTAACCCTCTGAATCAAATTATCCTTATAAAGCACAAACGGCACTTGCAA   690
         rThrIleThrIleGlyGlyLeuAsnProLeuAsnGlnIleIleLeuLysHisLysArgHisLeuGln
                                                                    HpaII
                                                                    |--|
    691  CTTCAATAAAACTAAACAGATAGCAACTTCTATCAAAGGTTTTGAGGATGTCCCGGCTAACGATGAGAA   759
         nPheGlnLysThrLysGlnIleAlaThrSerIleLysGlyPheGluAspValProAlaAsnAspGluLy
                                                                    744
```

FIGURE 4C

```
                                                    HindIII
                              HpaII    AluI
     RsaI                       |       |
      |
1036 TTCGTACCCAACTATGTGAAAAAATCGGTTCAATATCCGGTTAAGCTTTAGAATAAATGTGTGTGTTGG 1104
     aSerTyrProThrMET
        1041                                1073  1081
                                               1079

1105 TTATAATTAAGACTCTGTGTTGCATGTAATTTGTGAAATGGTAAGTTTATGTGATGCAAAAGATTGATA 1173

1174 AAAAAAAAAAAAA 1186
```

FIGURE 4E

```
3H11   TTTTTTTGAGCAAAGGGCAACTCAGATATCCAAAGATGAATCCAACATATA  51

3H11   GCTTACAGCTGGGAGAACATTGTCTAACTCTTCTGAAATTTAAATGTTATC 102

3H11   CAGAATCCTTCATCATAAAATAATATCAAAATGCAAATCTATTTTTTCTAC 153

3H11   TCTTGTCTAGCTTCAACTTTCTTCTTCTGCTCATCAATTAGCAATTAATCC 204
                                     TGCTCATCAATTAGCAATTAATCC

3H11   AAAACCATTATGGCTGCCAAAAATTCAGAGATGAAGTTTGCTATCTTCTTC 255
2A11   AAAACCATTATGGCTGCCAAAAATTCAGAGATGAAGTTTGCTATCTTCTTC
                   METAlaAlaLysAsnSerGluMETLysPheAlaIlePhePhe

3H11   GTTGTTCTTTTGACGACCACTTTAGTTGATATGTCTGGAATTTCGAAAATG 306
2A11   GTTGTTCTTTTGACGACCACTTTAGTTGATATGTCTGGAATTTCGAAAATG
       ValValLeuLeuThrThrThrLeuValAspMETSerGlyIleSerLysMET

3H11   CAAGTGATGGCTCTTCGAGACATACCCCCACAAGAAACATTGCTGAAAATG 357
2A11   CAAGTGATGGCTCTTCGAGACATACCCCCACAAGAAACATTGCTGAAAATG
       GlnValMETAlaLeuArgAspIleProProGlnGluThrLeuLeuLysMET

3H11   AAGCTACTTCCCACAAATATTTTGGGACTTTGTAACGAACCTTGCAGCTCA 408
2A11   AAGCTACTTCCCACAAATATTTTGGGACTTTGTAACGAACCTTGCAGCTCA
       LysLeuLeuProThrAsnIleLeuGlyLeuCysAsnGluProCysSerSer

3H11   AACTCTGATTGCATCGGAATTACCCTTTGCCAATTTTGTAAGGAGAAGACG 459
2A11   AACTCTGATTGCATCGGAATTACCCTTTGCCAATTTTGTAAGGAGAAGACG
       AsnSerAspCysIleGlyIleThrLeuCysGlnPhyCysLysGluLysThr

3H11   GACCAGTATGGTTTAACATACCGTACATGCAACCTGTTGCCTTGAACAATA 510
2A11   GACCAGTATGGTTTAACATACCGTACATGCAACCTGTTGCCTTGAACAATA
       AspGlnTyrGlyLeuThrTyrArgThrCysAsnLeuLeuPro

3H11   TCAATGATCTATCGATCGATCTATCTATCTATTTATCTGTCTCTGCGCGTA 561
2A11   TCAATGATCTATCGATCGATCTATCTATCTATTTATCTGTCTCTGCGCGTA

3H11   TAGTGTTGTCTGTACCTTTGGTGTGAAGAATATGAATAAAGGGATACATAT 612
2A11   TAGTGTTGTCTGTACCTTTGGTGTGAAGAATGTGAATAAAGGGATACATAT

3H11   ATCTAGATATATTCTAGGTAATGTCCTATTGTATTTAAAATTTGTAGCAAT 663
2A11   ATCTAGATATATTCTAGGTAATGTCCTATTGTATTTAAAATTTGTAGCAAT

3H11   GATTGTTTGAATAAAAACATACCATGAGTGAAATAATTATTCCACATTAAT 714
2A11   GATTGTTTGAATAAAAACATACCATGAGTGAAATAATTATTCC

3H11   TCACGTATTTATTTCACTTATGATACGTATTTTTGTTCCTTTCGCGTAAAA 765
3H11   AAAAAAAA    774
```

| | | | | | | | | | | | | |
|---|---|---|---|---|---|---|---|---|---|---|---|---|
| 2A11 | | V | M | A | L | R | D | I P P | Q | E | T | L | L |
| PA1b | | V | C | S | P | F | D | I P P | C | G | S | P | L C R C I |
| Chick pea inhibitor | | V | C | T | - | K | S | I P P | - | - | - | - | Q C R C N |
| Lima bean inhibitor | | L | C | T | - | K | S | I P P | - | - | - | - | Q C R C T |
| α₁-antitrypsin | L | G | A | I | P | M | S | I P P | E | V | | |

(b)

| | | | | | | | | | | | | | | |
|---|---|---|---|---|---|---|---|---|---|---|---|---|---|---|
| 2A11 | T | N | I | L | G | L | C | N | E | P | C | S | S N S D | C | I |
| PA1b | G | S | P | L | C | R | C | I | P | A | G | L | V I G N | C | R |
| Barley chloroform/methanol-soluble protein d | T | N | L | L | G | N | C | R | - | F | Y | L | V Q Q T | C | A |
| Wheat α-amylase inhibitor 0.28 | V | S | A | L | T | G | C | R | - | A | M | V | K L Q - | C | V |
| Wheat albumin | V | P | A | L | P | A | C | R | P | L | - | L | R L Q - | C | N |
| Millet bi-functional inhibitor | N | N | P | L | D | S | C | R | W | Y | V | S | ATKRT A | C | G |
| Castor bean 2S small subunit | Q | Q | N | L | R | Q | C | Q | E | Y | I | K | Q Q V S G Q | | |
| Napin small subunit | A | Q | N | L | R | A | C | Q | Q | W | L | N | K Q A M Q S | | |

FIGURE 6

2A11 GENOMIC

| | | | | | |
|---|---|---|---|---|---|
| CTCGAGCCCT | TTAAAAAGTA | TAGTCAATAT | TTACGGTGAC | CGTGAATTTC | TTAATTATGA | 60
| TATATAATTT | AAAAGAAATC | ATGATCACAT | TCTACTGATG | AGAACATGTG | CTAATCAAGG | 120
| GAAAACATGG | ATGTGAAAAA | TACTTTTTGT | TAAAAGTAAA | AAAAAATGTG | AAATTTTGTT | 180
| AGTTATTTAC | TACCTATACA | TTATTGAGC | ATGTGCAAAC | TTTACAAATA | CCTAATAGAA | 240
| GATTTTCACC | TGCCTGTATA | TATGTAAATT | AATTATAATG | AACACTCTCA | CATAAAATAA | 300
| TTATCAGTAT | ATACATTAAT | ACTTGCCCTC | CACAATGAAT | TAAATAAAAT | GTAGAACATG | 360
| ATCTACACTT | CAATAAAACT | AAGACCATAA | AGAATAATTT | CAAAATATAC | ACATGTCAAC | 420
| AATAAATTAT | TTGCATATTA | TATTAACTTA | CTAAACAATC | TTTACTTTTG | AAATATAAAA | 480
| ATAATCAAGT | TATAAGTCTG | CTCAAAGTAA | AGCACTTGTT | AGACTCATCT | GATTTTGAGA | 540
| AGGTAAGCAA | ATTGATGGTG | CATAATAGTC | ACAAGTAAAA | TATAAAATAG | ATTTCATTAG | 600
| TAAAATTGTT | TTTTACTTTC | TTTATATATA | ATTATCAATA | TCCTTCAATG | GTAGGTTAAT | 660
| TATATTGTTA | ACTTCTTGTT | GAATTAAAGC | AATAAGACAA | GAATATTAAA | GATAAAAGAA | 720
| CAATAAAAAT | AGAAAGACTA | AGAGATAAGA | GTTTTCTTAT | TCTTCTTTCA | ATAAGTATCA | 780
| TCAAGTGTAT | ACAATATAAA | TTTTTGTATT | TTTGATCTAT | CTATTTATAA | TGTTATATAT | 840
| AAGCATACAA | AAGATCAGTC | ATAAATATGA | CTTTAATCAT | GAAAATAATG | AAAGAGATTA | 900

FIGURE 7A

```
TGAAGGCGTA AGGTTACTAG AATAATAGTC ATTAAAAAAA GGGGTTATCT TTATAATTGA    960
ATAATTGATG AAGTAATGGA GATAATTAGT GAGCATAAAT TTTTTAAAA AAATGGACAT    1020
TTACACTATA ATATTTATA ACACTTTCCC TTAAACATCT AGGTATAAAT AATGAGTCTT    1080
GTCAAAATCT TAGTAGGAAA AATTCTGTGA AATTTTTTA GTGAAAACAA ATGATATAAA    1140
TATCTTGAAT ACTCATTATT TGTTGTCTCA TTAAAAATCT TATCTGACCT ATAAAATAAA   1200
TTATTGCTC AACTCAAAAT AGTTTTTCAT TCTAAAATTA GTATAATTAT TAGTGAATAT    1260
TTAATTAACA TAATTGTATA CTAAGGGGCC TATAAATTGG ATTCTTCTCA AAGAAAAATA   1320
AAATCACCAC ACAACTTTCT TCTTCTGCTC ATCAATTAGC AATTAATCCA AAACCATT    1378

ATG GCT GCC AAA AAT TCA GAG ATG AAG TTT GCT ATC TTC TTC GTT GTT    1426
MET Ala Ala Lys Asn Ser Glu MET Lys Phe Ala Ile Phe Phe Val Val

CTT TTG ACG ACC ACT TTA GGTTCACAAC ACTTCTCCCT TATTTTGTTT           1474
Leu Leu Thr Thr Thr Leu

TCTTAATTTC TTGGAAGTCA TATGCATGTG TTTGGTATCA TGGTATATAT ATAAAGGAAA  1534
ATATTTTCT TAATTACTGG TTTTCTAATG TTTGGTAGGT AATCGGAAAT TATTATGAGA   1594
TAATGAACTT GCAAAGTCAT TATTATATAA CTTTTTTTTT ATACTTTGAT TTAAGAATTC  1654
ATTTTCTCA TTTTATATAA ACTTATTTTT CAACAGAAAA TATTTTTCGA ACTATTCAAA   1714
CACACCCTAA GACATTACAT ATATATATAT ATACACCCTC CGTTTTATAT TACTTAATGC  1774
```

FIGURE 7B

```
CTATTGAGTT GGCCCACCCT TTAAGAATGA TTCAATTAGA GATATGTTTT ACTAAATTAA    1834

CCTATGCTTT AAGACTCTAA ATTTGGCTAT TACTATTTTA CGTTGTAATT TAATGACAAA    1894

CATTTCATAA TGACTATAGT CTGAACTTAA TTAGACAGAC GTATCTATAG TTTGCTTACT    1954

AATGATTCAT AGCTATATAT TTGGAGAGGA GAGAGACAAA CGATATTAAG AAAGGGAGGA    2014

GAGAGGCGAG GTAAATCTGA AATAGAGAAG AGAAAGGCAA CCAATTTTGA TCATCTATCA    2074

TACTTTTGAT TATTATTTTT ATTATATGTA CGTTACATT ACAGTTTTCG AATTCTTACA     2134

TTAATCTTAA TCATAATATA TACA GTT GAT ATG TCT GGA ATT TCG AAA ATG CAA  2188
                           Val Asp MET Ser Gly Ile Ser Lys MET Gln

GTG ATG GCT CTT CGA GAC ATA CCC CCA CAA GAA ACA TTG CTG AAA ATG     2236
Val MET Ala Leu Arg Asp Ile Pro Pro Gln Glu Thr Leu Leu Lys MET

AAG CTA CTT CCC ACA AAT ATT TTG GGA CTT TGT AAC GAA CCT TGC AGC     2284
Lys Leu Leu Pro Thr Asn Ile Leu Gly Leu Cys Asn Glu Pro Cys Ser

TCA AAC TCT GAT TGC ATC GGA ATT ACC CTT TGC CAA TTT TGT AAG GAG     2332
Ser Asn Ser Asp Cys Ile Gly Ile Thr Leu Cys Gln Phe Cys Lys Glu

AAG ACG GAC CAG TAT GGT TTA ACA TAC CGT ACA TGC AAC CTG TTG CCT     2390
Lys Thr Asp Gln Tyr Gly Leu Thr Tyr Arg Thr Cys Asn Leu Leu Pro

TGA ACAATATCAA TGATCTATCG ATCGATCTAT CTATCTATTT ATCTGTCTCT          2433

GCGCCTATAG TGTTGTCTGT ACCTTTGGTG TGAAGAATAT GAATAAAGGG ATACATATAT   2493

CTAGATATAT TCTAGGTAAT GTCCTATTGT ATTTAAAATT TGTAGCAATG ATTGTTTGAA   2553
```

FIGURE 7C

```
TAAAAACATA CCATGAGTGA AATAATTATT CCACATTAAT TCACGTATTT ATTTCACTTA 2613
TGATACGTAT TTTTGTTCCT TTCGCGTAGA TTTTTGATCC TTTTCCCTTT TGAATATTAA 2673
ACATTAAACA CAAATAATGT TTATTAAATT AAGTTAATAT TTTTATTTAG CTATTTATAT 2733
TTTTATTTGA AATCAAACTT GATAAATATT TATAAAGATA ATTAACAAGT AATGTGACAC 2793
TAACACCATG TAATATTATC TTGTCGTTAT TTATGATAAT ATTTTAAAAT TATAATTTCA 2853
GTTAAAAAAT TATTAAAAAA ACATACTTTT AAAAAGTGAG TTAGCCTCCG CTACCCACAT 2913
ACTTATGAAT TGGACTAGTT GTTTTTTGAC CCACAAAAAG AATGGGCTAA TTAAACCTGA 2973
CCTATCAAAT TTCAGAATCT GCATAGATTA GTCCGAACGA AATGAGTCAG CCCGTATTGA 3033
ACAAAATATC AACAAGGACG TTATGTAAAG ATGTTTAAGA AGGAAAAAAG ATTTCTAATA 3093
CATATGGACT TTCAATATCC CAACTTTGTC TGGCGATCTG AACCCTGCTT AGTTTGTTGA 3153
TCATTAACTT GTCTTGCTAT GTATTTAAGA TTTAAACTTT ATATGTTTAA ACTTACAGAA 3213
AATACATATA AATCTCTCAA GACTTGGCAA CATAATTTAC TTTAGTACTT AAAACTACATG 3273
AAAATTTAAA TATCCTTTTA ACATCTTTGA AGTGAATTAA ATTATCACAA TCCGAGCCTA 3333
CACCTTGGAC GTGGCCGGCA CTCAAGAACC AGTGCTGGTC CCCAAGCTAA CCCTCATCCT 3393
GACTGACTAC AAGCGGAAGG CTAACTTAAG TATACAAAAG CTTAAAACTG AATAAAATAA 3453
ACTTTACAAG GTTTTAACAC AAATGAACAA CTTTGAAGAA AATAATATAT TCAACTAGCC 3513
```

FIGURE 7D

```
ATAAAATAGA  CAACTTTAGT  CTTTAAAACA  TTTAATAAAA  TAAATGCAAA  ATATAGACTC  3573
CTTAACTAAA  CTGACTATCT  ATGGAGCCTC  TAATTGATAA  AGATGGAAGT  CGGGACAAGA  3633
CCACGACATC  CTGACTAAAC  TGAGAAGTAA  ATAAAATCCC  CCGGAAAAAA  AGGAGCCTCA  3693
CCATGGCTAA  CTCGAACTCG  GGGATATATC  AATGAAGCTC  CTGTTGATGA  TCTTGAAGAC  3753
ATGTCTCTGC  ATCATCAAAA  AGATGCAGGC  CAAATGGCTC  AGTACGTAAA  ATGTACGAGT  3813
ATGTAAGGGA  AATTCTAAAG  TATAACATAA  GCTTGATACT  TGAATAAAAG  GAAACATACT  3873
TACCTCTTTT  CAACTCAACT  CAAATTAAGA  ATAAGATACT  CAACTCAAAG  ATTAGGTATT  3933
CAACGCAAAT  ATGGCACTCT  ACTCAATGAA  GTACAAATTA  ACTCAGGATA  CTCGACTTAA  3993
GATACTCAAC  TCCCGACACT  CAACTGAACT  CATTTCAATA  TAAAGCAGCT  TAAAACAAGT  4053
TCAGTATAAA  GTAAAGTTGT  TTAAAAACAT  GATGTCAACT  CTGTGTGTAT  AATAAGGGAT  4113
ACAACATAAC  TTTGAAATGT  ATATAAAAAT  ACAATTAACT  GATGTATATA  AAAATACATT  4173
AATCTATGGG  AGATTCTCTA  ACCGACAACC  ATCACTTAAG  GGCTAAGATG  ATGATATAGC  4233
GATCTACCGC  ACGCTGCCAT  CGCATCTTAT  ACCCGGCCAA  AGGTATAAGA  CCTGAACTGC  4293
CTAATGAATC  CACTAATAAA  CTGTTAAAAG  GAATCATCTA  AAAAGTATGA  CCCTTTTCTA  4353
CCCATAGTGG  CTAACATGGT  TTATGGGGGC  TGTGAGTTAT  CTGAACTCTC  CCCCATATCG  4413
```

FIGURE 7E

```
GTGCTCAATA CTACTCCAAA AAATATACTG CTCTTATGTT TAAAAACATA CTGATTCTGT    4473
GGTTTGAAAT TATTGCTTAA AGCTTAGATT TTTGAAAAGC TCTCTTTTGA AAATCGTAGT    4533
TTCCTTTTTC TTCTATTAAA GCTAGACATA GGCTATGTAG AACTCTAGCT TACCTTCCTT    4593
CTCAAAAGTT TGAAAACATT TGCTTAGATT CTTAGGGACT ACTTAGTTCC CTTGTTGGAA    4653
TTC                                                                  4656
```

FIGURE 7F

PG GENOMIC

```
          10         20         30         40         50         60
                                                                   *
AAGCTTCTTA AAAAGGCAAA TTGATTAATT TGAAGTCAAA ATAATTAATT ATAACAGTGG 70         80         90        100        110        120
                                                                   *
TAAAGCACCT TAAGAAACCA TAGTTTGAAA GGTTACCAAT GCGCTATATA TTAATCAACT 130        140        150        160        170        180
                                                                   *
TGATAATATA AAAAAAATTT CAATTCGAAA AGGGCCTAAA ATATTCTCAA AGTATTCGAA 190        200        210        220        230        240
                                                                   *
ATGGTACAAA ACTACCATCC GTCCACCTAT TGACTCCAAA ATAAAATTAT TATCCACCTT 250        260        270        280        290        300
                                                                   *
TGAGTTTAAA ATTGACTACT TATATAACAA TTCTAAATTT AAACTATTTT AATACTTTTA 310        320        330        340        350        360
                                                                   *
AAAATACATG GCGTTCAAAT ATTTAATATA ATTTAATTTA TGAATATCAT TTATAAACCA 370        380        390        400        410        420
                                                                   *
ACCAACTACC AACTCATTAA TCATTAAATC CCACCCAAAT TCTACTATCA AAATTGTCCT 430        440        450        460        470        480
                                                                   *
AAACACTACT AAAACAAGAC GAAATTGTTC GAGTCCGAAT CGAAGCACCA ATCTAATTTA 490        500        510        520        530        540
                                                                   *
GGTTGAGCCG CATATTTAGG AGGACACTTT CAATAGTATT TTTTTCAAGC ATGAATTTGA
         550        560        570        580        590        600
                                                                   *
AATTTAAGAT TAATGGTAAA GAAGTAGTAC ATCCCGAATT AATTCATGCC TTTTTTAAAT 610        620        630        640        650        660
                                                                   *
ATAATTATAT AAATATTTAT GATTTGTTTT AAATATTAAA ACTTGAATAT ATTATTTTTT 670        680        690        700        710        720
                                                                   *
TAAAAATTAT CTATTAAGTA CCATCACATA ATTGAGACGA AGGAATAATT AAGATGAACA
         730        740        750        760        770        780
                                                                   *
TAGTGTTTAA TTAGTAATGG ATGGGTAGTA AATTTATTTA TAAATTATAT CAATAAGTTA 790        800        810        820        830        840
                                                                   *
AATTATAACA AATATTTGAG CGCCATGTAT TTTAAAAAAT ATTAAATAGT TTGAATTTAA
```

FIGURE 8A

```
         850        860        870        880        890        900
                                                                  *
AACCGTTAGA TAAATGGTCA ATTTTGAACC CAAAAGTGGA TGAGAAGGGT ATTTTAGAGC 910        920        930        940        950        960
                                                                  *
CAATAGGRGG ATGAGAAGGA TATTTTGAAG CCAATATGTG ATGGATGAAG GATAATTTTG 970        980        990       1000       1010       1020
                                                                  *
TATCATTTCT AATACTTTAA AGATATTTTA GGTCATTTTC CCTTCTTTAG TTTATAGACT 1030       1040       1050       1060       1070       1080
                                                                  *
ATAGTGTTAG TTCATCGAAT ATCATCTATT ATTTCCGTCT TAAATTATTT TTTATTTTAT 1090       1100       1110       1120       1130       1140
                                                                  *
AAATTTTTTA AAAATAAATT ATTTTTTCCA TTTAACTTTG ATTGTAATTA ATTTTTAAAA 1150       1160       1170       1180       1190       1200
                                                                  *
ATTACCAACA TATAAATAAA ATTAATATTT AACAAAGAAT TGTAACATAA TATTTTTTTA 1210       1220       1230       1240       1250       1260
                                                                  *
ATTATTCAAA ATAAATATTT TTAAACATCA TATAAAGAA ATACGACAAA AAAATTGAGA 1270       1280       1290       1300       1310       1320
                                                                  *
CGGGAGAAGA CAAGCCAGAC AAAAATGTCC AAGAAACTCT TTCGTCTAAA TATCTCTCAT 1330       1340       1350       1360       1370       1380
                                                                  *
CCAAACTAAT ATAATACCCA TTATAATTAA CCATATTGAC CAACTCAAAC CCCTTAAAAT 1390       1400       1410       1420       1430       1440
                                                                  *
CTATAAATAG ACAAACCCTT CCCATACCTC TTATCATAAA AAAAATAATA ATCTTTTTCA 1450       1460       1470       1480       1490       1500
                                                                  *
ATAGACAAGT TTAAAAACCA TACCATATAA CAATATATCA TGGTTATCCA AAGGAATAGT 1510       1520       1530       1540       1550       1560
                                                                  *
ATTCTCCTTC TCATTATTAT TTTTGCTTCA TCAATTTCAA CTTGTAGAAG CAATGTTATT 1570       1580       1590       1600       1610       1620
                                                                  *
GATGACAATT TATTCAAACA AGTTTATGAT AATATTCTTG AACAAGAATT TGCTCATGAT 1630       1640       1650       1660       1670       1680
                                                                  *
TTTCAAGCTT ATCTTTCTTA TTTGAGCAAA AATATTGAAA GCAACAATAA TATTGACAAG
```

FIGURE 8B

```
      1690       1700       1710       1720       1730       1740
                                                                *
GTTGATAAAA ATGGGATTAA AGTGATTAAT GTACTTAGCT TTGGAGCTAA GGGTGATGGA 1750       1760       1770       1780       1790       1800
                                                                *
AAAACATATG ATAATATTGT AAGTATTTAA ATATTGGAAT ATATTTGTGG GGATGAAAAT 1810       1820       1830       1840       1850       1860
                                                                *
GATAGAGAAT ATAAGAATTA TTTGGAAGGA TGAAAAGTTA TATTTTATAA AGTAGAAAAT 1870       1880       1890       1900       1910       1920
                                                                *
TATTTTCTCG TTTTTAGTAA TTAAAGGTGA AAAATGAGTT TTCTCGTAAG CGAGGAAAGT 1930       1940       1950       1960       1970       1980
                                                                *
CATTTTCCAT GGAACTGTAT TTTTTTTTTA CTTTTAATAA CGTCATAGTA TTTGCTATAC 1990       2000       2010       2020       2030       2040
                                                                *
TCAAGAATAA GACACTATTA TTGATGTTTA GTGCTCGAAA AGAAATTGAT AGTAATTTTG 2050       2060       2070       2080       2090       2100
                                                                *
CTAATATAAC TATCAATTTC TTATATGTAT ATTTTTCAAC CAAAATAACA AAGCGTAATC 2110       2120       2130       2140       2150       2160
                                                                *
CAATAAGTGG GCCTCTAGAA TAAAGAGTAA GTTCTATTAA TTCTTAACCT TATTTAATTT 2170       2180       2190       2200
TATGGAAACC TCGACAAAAC GACAATGCTC AACTTATATT CGAATTC
```

FIGURE 8C

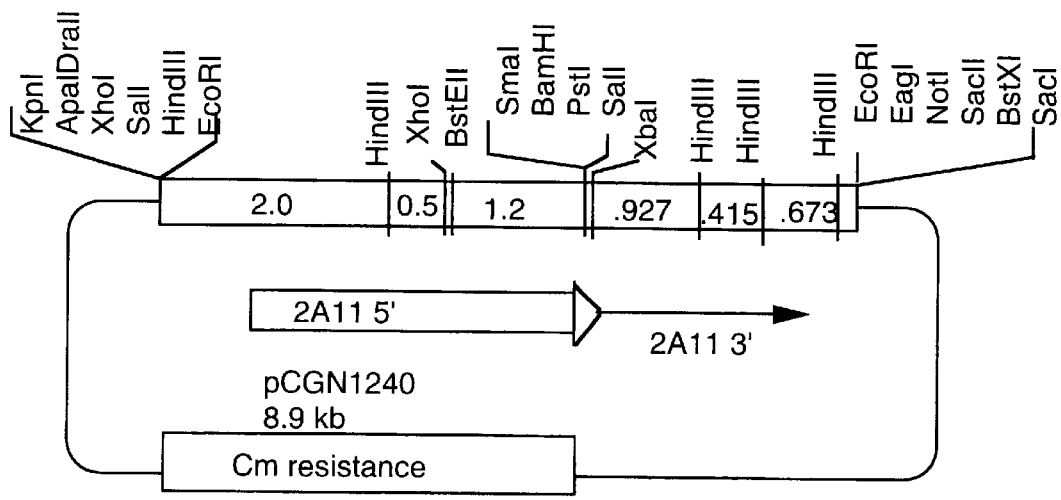
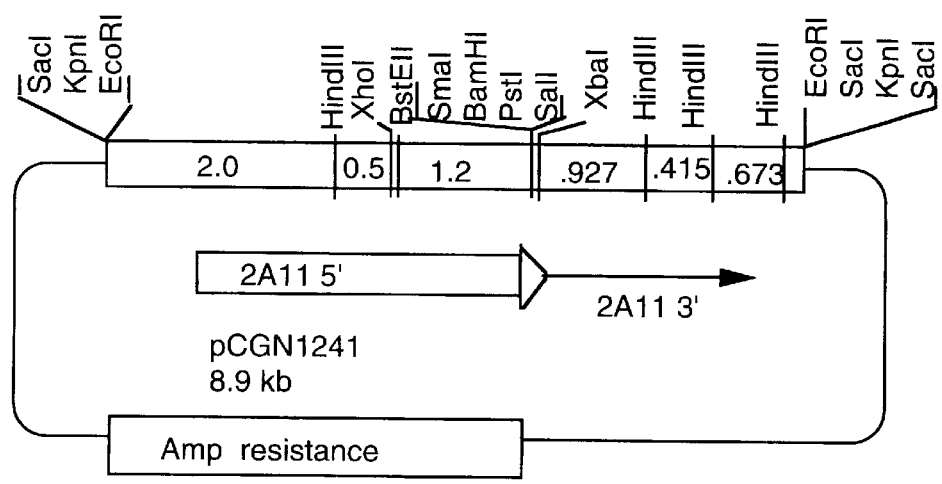
FIGURE 10A

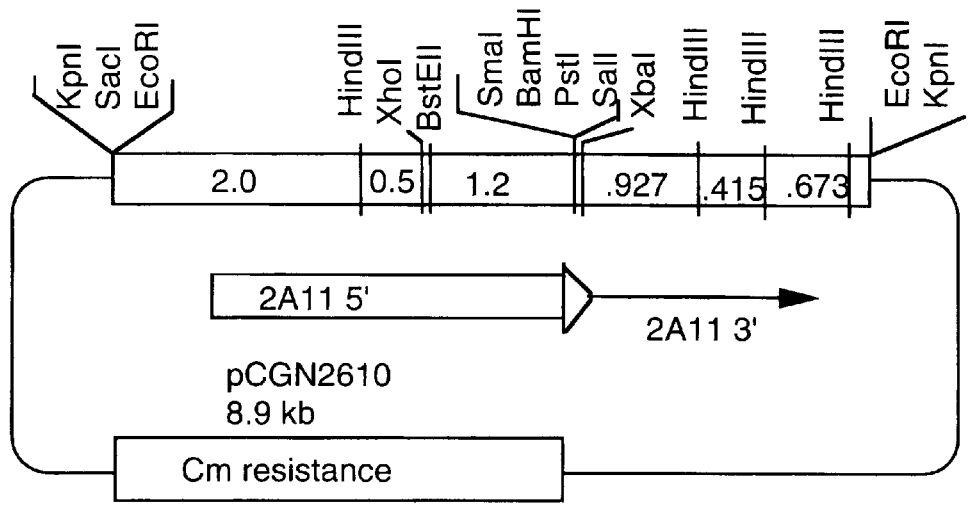
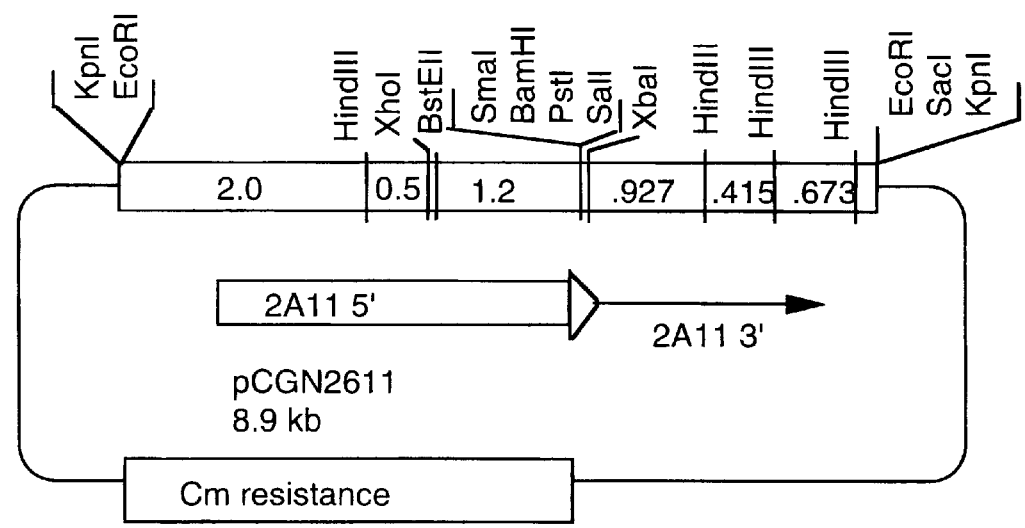
FIGURE 10B

METHODS AND COMPOSITIONS FOR REGULATED TRANSCRIPTION AND EXPRESSION OF HETEROLOGOUS GENES

This application is a continuation of U.S. Ser. No. 08/484,941, filed Jun. 7, 1995, now U.S. Pat. No. 5,750,385, which is a continuation of U.S. Ser. No. 08/105,852, filed Aug. 10, 1993, now U.S. Pat. No. 5,753,475; U.S. Ser. No. 08/105,852 is a continuation in part of Ser. No. 07/526,123, filed May 21, 1990, pending, which is a continuation of U.S. Ser. No. 07/267,865, filed Nov. 2, 1988, abandoned, which is a continuation of U.S. Ser. No. 06/692,605, filed Jan. 17, 1985, abandoned; U.S. Ser. No. 08/105,852, is also a continuation in part of U.S. Ser. No. 07/582,241, filed Sep. 14, 1990, abandoned, which is a continuation of U.S. Ser. No. 07/188,361, filed Apr. 29, 1988, abandoned, which is a continuation in part of U.S. Ser. No. 07/168,190, filed Mar. 15, 1988, abandoned, which is a continuation in part of U.S. Ser. No. 07/054,369, filed May 26, 1987, which issued on Jul. 24, 1990 as U.S. Pat. No. 4,943,674; U.S. Ser. No. 08/105,852 is also a continuation in part of U.S. Ser. No. 07/742,834, filed Aug. 8, 1991, which issued as U.S. Pat. No. 5,420,034 on May 30, 1995, which is a continuation of U.S. Ser. No. 07/550,804, filed Jul. 9, 1990, abandoned, which is a continuation of U.S. Ser. No. 07/147,781, filed Jan. 25, 1988, abandoned, which is a continuation in part of U.S. Ser. No. 07/078,538, filed Jul. 28, 1987, abandoned, which is a continuation in part of U.S. Ser. No. 06/891,529, filed Jul. 31, 1986, abandoned.

TECHNICAL FIELD

This invention relates to regulated genetic modification of plant material, particularly for tissue and/or developmental specific trascription and expression. Heterologous constructs are provided whereby production of endogenous products can be modulated or new capabilities provided.

BACKGROUND

While the ability to manipulate bacterial and mammalian cells by hybrid DNA technology has been available for almost a decade, only in 1983 was it first reported that successful expression of an exogenous gene was achieved in a plant cell. Plants have a highly complex genome and differ in numerous ways from both bacterial and mammalian genes. Therefore, while as a first approximation, one may extrapolate from the experience with other species, the relevance of such experience must be determined by experimentation. In general, genetic engineering techniques have been directed to modifying the phenotype of individual prokaryotic and eukaryotic cells, especially in culture. Plant cells have proven more intransigent than other eukaryotic cells due not only to the lack of suitable vector systems but also a result of the different goals involved. Plant genetic engineering has for the most part been directed to modifying the entire plant or a particular tissue rather than modifying a single cell in culture.

In order to be able to successfully modify plant cells, it will be necessary to develop a large number of different systems for introducing the exogenous DNA into the plant cell, for directing, as appropriate, the introduced DNA either randomly or to particular genomic sites, to provide for constitutive or regulated expression and, as appropriate, to provide for transport of the product to an appropriate site. Toward this end, it will be necessary to develop a wide variety of regulatory signals involved with replication, transcription, translation, integration, and the like. To varying degrees these regulatory signals will have general application across species or be speciesspecific, will be associated with specific stages of plant growth, or be subject to external control. To that extent, it will be necessary to develop a wide spectrum of regulatory sequences to allow for expression under predetermined conditions.

For many applications, it will be desirable to provide for transcription in a particular plant tissue and/or at a particular time in the growth cycle of the plant or maturation cycle of the tissue. Toward this end, there is substantial interest in identifying endogenous plant products transcription or expression of which is regulated in a manner of interest. In identifying such products, one must first look for a product which appears at a particular time in the cell growth cycle or in a particular plant tissue, demonstrate its absence at other times or in other tissue, identify nucleic acid sequences associated with the product and then identify the sequence in the genome of the plant in order to obtain the 5'-untranslated sequence associated with transcription. Identifying the particular sequence, followed by establishing that it is the correct sequence and isolating the desired transcriptional regulatory region requires an enormous outlay in time and effort. One must then prepare appropriate constructs, and demonstrate that the constructs are efficacious in the desired manner.

There has been substantial interest in modifying the seed with transcriptional initiation regions to afford transcription and expression of the gene introduced into the seed, rather than constitutive expression which would result in expression throughout the plant. Also of interest is the ability to change the phenotype of fruit, so as to provide fruit which will have improved aspects for storage, handling, cooking, organoleptic properties, freezing, nutritional value, and the like.

In addition, different systems may be required for the introduction of nucleic acid into plant cells to obtain reasonable efficiencies of transformation and functioning of the nucleic acid. In many instances, such as the tumor inducing plasmids and viruses, the vectors have found limited utilization in their range of hosts. Therefore, different transformation and replication systems may be required for different plant species.

RELEVANT LITERATURE

Lack of transformation by Agrobacterium of soybean is reported by DeCleene and DeLey, *The Botanical Review* (1976) 42:389–446. Encouraging results in the transformation (Pederson et al., *Plant Cell Repts.* (1983) 2:201–204 and Hood et al., *Bio/Technology* (1984) 2:702–708) and regeneration (Christianson et al., *Science* (1983) 222: 632–634) of soybean have recently been reported. A light inducible soybean SSU gene (small subunit SSU) of ribulose-1,5-bisphosphate-carboxylase (RuBP-carboxylase) is reported by Berry-Lowe et al., *J. Mol. Appln. Gen.* (1982) 1:483–498. Sequences 5' to the pSSU gene were recently shown to direct foreign gene expression in a light-inducible manner when transferred into tobacco callus (Herrera-Estrella et al., *Nature* (1984) 310:115–120).

Crouch et al., In: *Molecular Form and Function of the Plant Genome*, eds. van Vloten-Doting, Groot and Hall, Plenum Publishing Corp. 1985, pp 555–566; Crouch and Sussex, Planta (1981) 153:64–74; Crouch et al., *J. Mol. Appl. Genet.* (1983) 2:273–283; Simon et al., *Plant Molecular Biology* (1985) 5:191–201; and Scofield and Crouch, *J. Biol. Chem.* (1987) 262:12202–12208, describe various aspects of Brassica napus storage proteins. Rose et al., *Nucl.*

Acids Res. (1987) 15:7197 and Scherer and Knauf, *Plant Mol. Biol.* (1987) 9:127–134 describe ACP genes. Beachy et al., *EMBO J.* (1985) 4:3047–3053; Sengupta-Gopalan et al., *Proc. Natl. Acad. Sci. USA* (1985) 82:3320–3324; Greenwood and Chrispeels, *Plant Physiol.* (1985) 79:65–71 and Chen et al., *Proc. Natl. Acad. Sci. USA* (1986) 83:8560–8564 describe studies concerned with seed storage proteins and genetic manipulation. Eckes et al., *Mol. Gen. Genet.* (1986) 205:14–22 and Fluhr et al., *Science* (1986) 232:1106–1112 describe the genetic manipulation of light inducible plant genes.

cDNA clones from tomato displaying differential expression during fruit development have been isolated and characterized (Mansson et al., *Mol. Gen. Genet.* (1985) 200:356–361; Slater et al., *Plant Mol. Biol.* (1985) 5:137–147). The studies have focused primarily on mRNAS which accumulate during fruit ripening. One of the proteins encoded by the ripening-specific cDNAs has been identified as polygalacturonase (Slater et al., *Plant Mol. Biol.* (1985) 5:137–147). A cDNA clone which encodes tomato polygalacturonase has been sequenced. Grierson et al., *Nucleic Acids Research* (1986) 14:8395–8603. The concentration of polygalacturonase mRNA increases 2000-fold between the immature-green and red-ripe stages of fruit development. This suggests that expression of the enzyme is regulated by the specific mRNA concentration which in turn is regulated by an increase in transcription. Della Penna et al., *Proc. Natl. Acad. Sci. USA* (1986) 83:6420–6424. Mature plastid mRNA for psbA (one of the components of photosystem II) reaches its highest level late in fruit development, whereas after the onset of ripening, plastid mRNAS for other components of photosystem I and II decline to nondetectable levels in chromoplasts. Piechulla et al., *Plant Mol. Biol.* (1986) 7:367–376.

SUMMARY OF THE INVENTION

Novel methods and DNA constructs are provided for transforming plants employing T-DNA and a Ti- or Ri-plasmid for heterologous DNA introduction and integration into the plant genome. Transformation without gall formation of plant cells which have historically not been Agrobacterium hosts is achieved with successful expression of the heterologous DNA. Additionally, DNA constructs are provided which are employed in manipulating plant cells to provide for regulated transcription, such as light inducible transcription, in a plant tissue or plant part of interest at particular stages of plant growth or in response to external control. Particularly, transcriptional regions from seed storage proteins, seed coat proteins or acyl carrier protein are joined to other than the homologous gene and introduced into a plant cell host for integration into the genome to provide for seed-specific transcription. The constructs provide for modulation of expression of endogenous products as well as production of exogenous products in the seed. Novel DNA constructions also are provided employing a fruit-specific promoter, particularly a promoter from a gene active beginning at or shortly after anthesis or beginning at the breaker stage, joined to a DNA sequence of interest and a transcriptional termination region. A DNA construct may be introduced into a plant cell host for integration into the genome and transcription regulated at a time at or subsequent to anthesis. In this manner, high levels of RNA and, as appropriate, polypeptides, may be achieved during formation and/or ripening of fruit.

BRIEF DESCRIPTION OF THE DRAWINGS

FIGS. 1A–1F are a partial sequence of the promoter region of the λBnNa napin gene. The start (ATG) of the open reading frame is underlined.

FIGS. 2A–2L are a restriction map of cloned λCGN1-2 showing the entire coding region sequence as well as extensive 5' upstream and 3' downstream sequences.

FIGS. 3A–3G are a partial nucleotide sequence of genomic ACP clone Bcg4-4. The coding region is indicated by the three-letter amino acid codes. Breaks in the coding region sequence represent introns. The underlined nucleotide at position 310 is ambiguous without further sequence analysis for confirmation.

FIGS. 4A–4E are the complete nucleotide sequence of B. campestris cDNA EA9. The longest open reading frame is designated by the three letter amino acid code. PolyA tails are evident at the end of the sequence and a potential polyadenylation signal is underlined.

FIGS. 5 shows the nucleotide sequence of the cDNA clones PCGN1299 (2A11) and PCGN1298 (3H11). The amino acid sequence of the polypeptide encoded by the open reading frame is also indicated.

FIG. 6 is a comparison of 2A11 to pea storage proteins and other abundant storage proteins:

(a) 2A11 (residues 33–46) is compared to PA1b and the reactive site sequences of some protease inhibitors, Pa1b (residues 6–23), chick pea inhibitor (residues 11–23), lima bean inhibitor (residues 23–35), human α1-antitrypsin reactive site peptide. The arrow indicates the reactive site.

(b) is a comparison of the amino terminal sequence of 2A11 with the amino termini of a range of seed proteins. The data have been modified or deletions introduced to maximize homology; conserved residues are shown boxed. The sequences are from the following sources: PA1b; barley chloroform/methanol-soluble protein d; wheat albumin; wheat α-amylase inhibitor 0.28; millet bi-functional inhibitor; castor bean 2S small subunit; and napin small subunit.

FIGS. 7A–7F show the complete sequence of the 2A11 genomic DNA cloned into PCGN1273 from the XhoI site (position 1 at the 5' end) to the EcoRI site (position 4654).

FIGS. 8A–8C show the nucleotide sequence of a polygalacturonase (PG) genomic clone.

Figure 9:
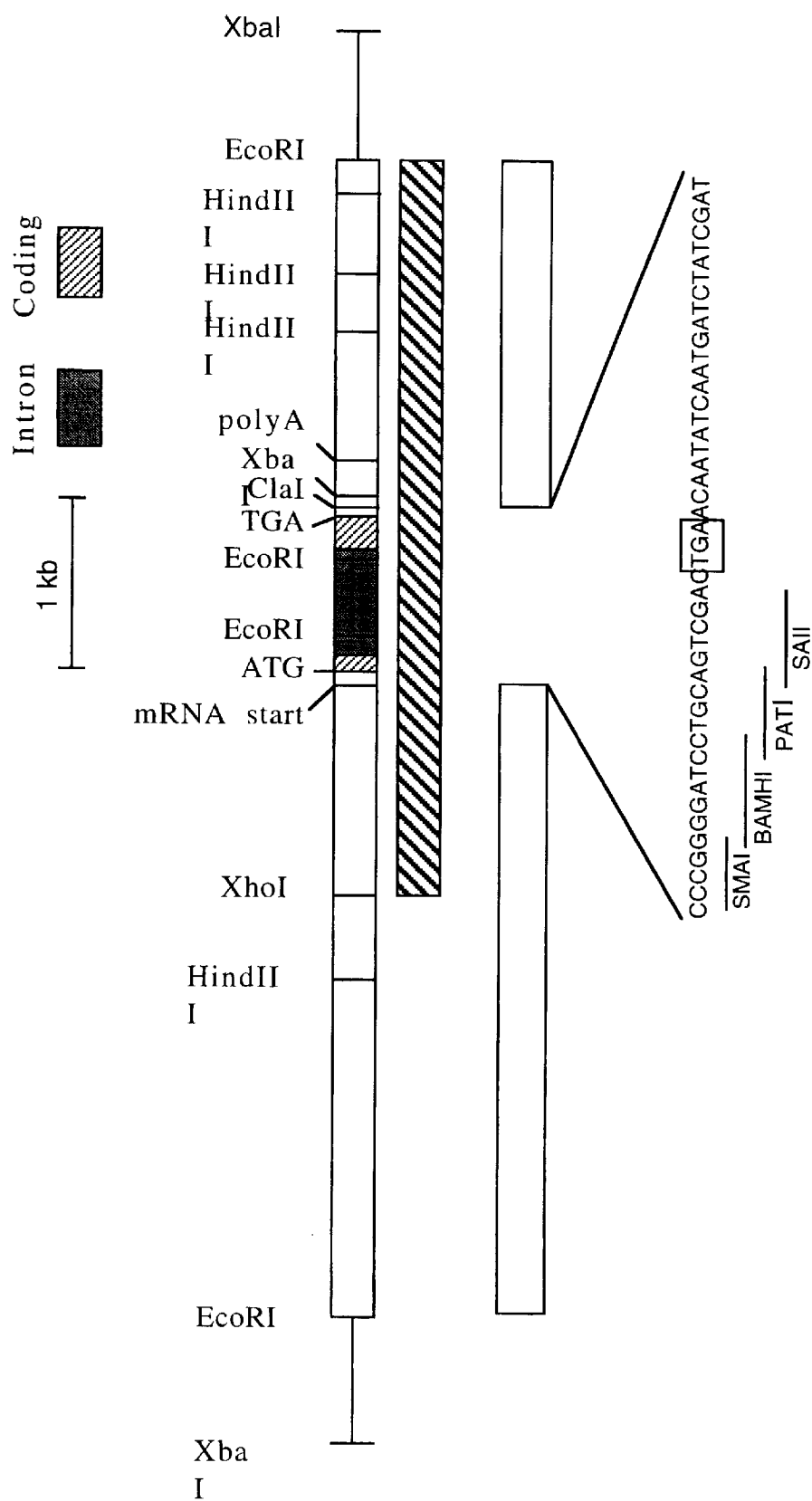

FIG. 9 shows 2A11 genomic constructs. The upper line shows a map of the 2A11 genomic clone. The transcriptional start site, the polyadenylation site, the start (ATG) and stop (TGA) sites and the position of the intron are indicated. The hatched region indicates the portion of the genomic clone that was used to make the tagged 2A11 constructions. The bottom portion shows the regions used to construct the 2A11 cassettes including the synthetic oligonucleotide used to insert restriction sites and reconstruct the 3' end.

FIG. 10 shows examples of 2A11 cassettes. Four versions of the 2A11 cassette are shown. They differ only in the flanking poly-linker regions and in the antibiotic resistance marker on the plasmid.

DESCRIPTION OF THE PREFERRED EMBODIMENTS

In accordance with the subject invention, DNA constructs are provided which allow for regulated modification of plant phenotype for example during fruit development and ripening, in specific plant structures derived from the ovum, and in chloroplast containing plant tissues such as leaves. The DNA constructs comprise a regulated transcriptional initiation region. Downstream from the regulated transcriptional initiation region will be a sequence of interest which will provide for regulated modification of plant phenotype, by modulating the production of an endogenous product, as to amount, relative distribution, or the like, or production of an exogenous expression product to provide for a novel function or product. Thus genes of interest as a source of regulated transcriptional initiation regions include those genes associated with seed formation, preferably in association with embryogenesis and seed maturation and those associated with fruit maturation and ripening, fruit rotting and light-induced processes in chloroplasts. The transcriptional cassette will include in the 5'- 3' direction of transcription, a regulated transcriptional and translational initiation region, a sequence of interest, and a transcriptional and translational termination region functional in plants. One or more introns may be also present.

In addition to the transcription construct, depending upon the manner of introduction of the transcription construct into the plant, other DNA sequences may be required. The subject invention includes a novel method provided for the introduction of foreign DNA employing T-DNA from an Agrobacterium plasmid, where efficient functional introduction of heterologous DNA is achieved in plants normally considered outside the Agrobacterium range, e.g., monocotyledons and leguminous dicotyledons, without gall formation. The method can also be used with the known dicotyledon hosts of Agrobacterium. DNA constructs are made which can be inserted into an Agrobacterium plasmid for transfer to a plant host. Plant hosts of particular interest are the grains and legumes.

When using the Ti- or Ri-plasmid for transformation of plant cells, as described below, at least the right border and frequently both the right and left borders of the T-DNA of the Ti- or Ri-plasmids will be joined as flanking regions to the transcription construct. The use of T-DNA as a flanking region in a construct for integration into a Ti- or Ri-plasmid has been described in EPO Application No. 116,718 and PCT Application Nos. WO84/02913, 02919 and 02920. See also Herrera-Estrella, Nature (1983) 303:209–213; Fraley et al., Proc. Natl. Acad. Sci, USA (1983) 80:4803–4807; Horsch et al., Science (1984) 223:496–498; and DeBlock et al., EMBO J. (1984) 3:1681–1689. Various fragments may be employed in the constructions to provide for homology with the T-DNA of the tumor plasmids. The homology may involve structural genes, promoter regions, other untranslated regions such as border regions, or the like.

Downstream from and under the transcriptional initiation regulation of the regulatable initiation region will be a sequence of interest which will provide for modification of the phenotype of the specific plant tissue or part. Desirably, integration constructs may be prepared which allow for integration of the transcriptional cassette into the genome of a plant host. Conveniently, the vector may include a multiple cloning site downstream from the regulated transcriptional initiation region, so that the integration construct may be employed for a variety of sequences in an efficient manner. The DNA construct will also provide for a termination region, so as to provide an expression cassette into which a gene may be introduced. Conveniently, transcriptional initiation and termination regions may be provided separated in the direction of transcription by a linker or polylinker having one or a plurality of restriction sites for insertion of the gene to be under the transcriptional regulation of the regulatory regions. Usually, the linker will have from 1 to 10, more usually from about 1 to 8, preferably from about 2 to 6 restriction sites. Generally, the linker will be fewer than 100 bp, frequently fewer than 60 bp and generally at least about 5 bp. In conjunction with the subject method these constructs may be used for the introduction of the structural gene into plant cells in culture, where the cells may be regenerated into whole plants.

The DNA constructs which are provided employ T-DNA flanking regions, flanking a structural gene including transcriptional and translational regulatory sequences. Thus, the construct which includes the structural gene, its transcriptional and translational regulatory controls, and the T-DNA flanking regions will for the most part have the following formula:

$$(T^1)_a\text{-}P\text{-}S.G.\text{-}Te\text{-}(T^2)_b$$

wherein:

$T^1$ and $T^2$ are the same or different and are T-DNA from a Ti- plasmid or an Ri- plasmid, where a and b and 0 or 1, at least 1 of a and b being 1;

P is a promoter region recognized by a plant host, which promoter region may include promoters derived from Ti- or Ri- plasmids, such as the octopine synthase or nopaline synthase promoters, viral promoters, plant promoters, particularly leguminous and monocotyledonous plant host promoters of various structural genes, e.g., RuBP-carboxylase, more particularly SSU. The promoter region will normally include a region for binding of RNA polymerase, as well as a cap site. In addition, there may be present enhancers, operators, activators, or other regions involved with transcriptional regulation. The transcriptional initiation region may be native or homologous to the host or foreign or heterologous to the host. By foreign is intended that the transcriptional initiation region is not found in the wild-type host into which the transcriptional initiation region is introduced.

S.G. intends a structural gene having an open reading frame and having at its 5'-end an initiation codon and at its 3'-end one or more nonsense codons. The DNA sequence may have any open reading frame encoding a peptide of interest, e.g. an enzyme, or a sequence complementary to a genomic sequence, where the genomic sequence may be an open reading frame, an intron, a non-coding leader sequence, or any other sequence where the complementary sequence will inhibit transcription, messenger RNA processing, e.g. splicing, or translation. The DNA sequence of interest may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest.

Te intends a termination region functional in the plant host cell. The termination region, besides including at least one terminating sequence, may also include a polyA signal. The termination region which is employed will be primarily one of convenience, since the termination regions appear to be relatively interchangeable. The termination region may be native with the transcriptional initiation region, may be native with the DNA sequence of interest, or may be derived from another source. Convenient termination regions are available from the Ti-plasmid of A. tumefaciens, such as the octopine synthase and nopaline synthase termination regions.

Identifying useful regulated transcriptional initiation regions may be achieved in a number of ways. For example, where a fruit or seed protein has been or is isolated, it is partially sequenced, so that a probe can be designed for identifying messenger RNA specific for fruit or seed. To further enhance the concentration of the messenger RNA specifically associated with fruit or seed, cDNA can be prepared and the cDNA subtracted with messenger RNA or cDNA from non-seed or non-fruit associated cells. The residual cDNA can then be used for probing the genome for complementary sequences, using an appropriate library prepared from plant cells. Sequences which hybridize to the cDNA then can be isolated, manipulated, and the 5'-untranslated region associated with the coding region isolated and used in expression constructs to identify the transcriptional activity of the 5'-untranslated region. In some instances, a probe may be employed directly for screening a genomic library and identifying sequences which hybridize to the probe. The sequences will be manipulated as described above to identify the 5'-untranslated regions.

As an example, a promoter of particular interest for the subject invention, the fruit-specific transcriptional initiation region (promoter) from a DNA sequence which encodes a protein described as 2A11 in the experimental section was identified as follows. cDNA clones made from ripe fruit were screened using cDNA probes made from ripe fruit, green fruit, and leaf mRNA. Clones were selected having more intense hybridization with the fruit DNAs as contrasted with the leaf cDNAs. The screening was repeated to identify a particular cDNA referred to as 2A11. The 2A11 cDNA was then used for screening RNA from root, stem, leaf, and seven stages of fruit development after the mRNA was sized on gels. The screening demonstrated that the particular message was present throughout the seven stages of fruit development. The mRNA complementary to the specific cDNA was absent in other tissues which were tested. The cDNA was then used for screening a genomic library and a fragment selected which hybridized to the subject cDNA. The 5' and 3' non-coding regions were isolated and manipulated for insertion of a foreign sequence to be transcribed under the regulation of the 2A11 promoter.

The expression constructs which are prepared employing the regulated 5'-untranslated regions may be transformed into plant cells as described previously for evaluation of their ability to function with a heterologous structural gene (i.e., a gene other than the open reading frame associated with the 5'-untranslated region) and specificity of expression for example in a particular plant tissue or plant part such as leaves, seed or fruit. In this manner, specific sequences may be identified for use with sequences for fruit or seed-specific transcription and light-induced transcription.

Several promoters are of particular interest. These include the soybean SSU promoter, promoters from genes encoding storage proteins and seed embryo genes and those from genes that are activated at or shortly after anthesis. The transcriptional initiation region may be native or homologous to the host or foreign or heterologous to the host. By foreign relative to a particular host is intended that the transcriptional initiation region is not found in the wild-type host into which the transcriptional initiation region is introduced. Other fruit-specific promoters may be activated at times subsequent to anthesis, such as prior to or during the green fruit stage, during pre-ripe (e.g., breaker) or even into the red fruit stage.

By use of the soybean SSU promoter, it is found that the expression of the gene under the SSU promoter can be light-induced. Thus, the expression of the gene is regulatable, where enhanced expression occurs during irradiation with light, while substantially reduced expression or no expression occurs in the absence of light. The nucleotide sequence of the small subunit gene is described by Berry-Lowe, *J. Mol. Appl. Gen.* (1982) 1:483–498. A DdeI digest of a plasmid containing a genomic fragment which includes the SSU soybean gene yields a 1.1 kd 5' piece that can be used as a promoter fragment.

Transcriptional initiation regions from genes encoding storage proteins, such as those from genes encoding napin, cruciferin, β-conglycinin, phaseolin, or the like, and proteins involved in fatty acid biosynthesis, such as acyl carrier protein (ACP) are also of interest. The transcriptional initiation regions may be obtained from any convenient host, particularly plant hosts such as Brassica, e.g. napus or campestris, soybean (Glycine max), bean (*Phaseolus vulgaris*), corn (*Zea mays*), cotton (*Gossypium sp.*), safflower (*Carthamus tinctorius*), tomato (*Lycopersicon esculentum*), and Cuphea species.

Other transcriptional initiation regions of particular interest are those associated with seed embryo genes that are expressed in the period from about day 7 to day 40, particularly those having maximum expression in the period from about day 10 to about day 30, postanthesis, and seed coat genes which are expressed in the period from about day 11 to day 30. Usually the period of expression will be at least 3 days, more usually about 7 days and may be substantially over the entire period.

Also of interest is a transcriptional initiation region which is activated at or shortly after anthesis, so that in the early development of the fruit, it provides the desired level of transcription of the sequence of interest. Normally, the sequence of interest will be involved in affecting the process in the early formation of the fruit or providing a property which is desirable during the growing (expansion) period of the fruit, or at or after harvesting.

The ripening stages of the tomato may be broken down into mature green, breaker, turning, pink, light red and red. Desirably, the transcriptional initiation region maintains its activity during the expansion and maturation of the green fruit, more desirably continues active through the ripening or red fruit period. Comparable periods for other fruit are referred to as stages of ripening. The invention is not limited to those transcriptional initiation regions which are activated at or shortly after anthesis but also includes transcriptional initiation regions which are activated at any of the ripening stages of the fruit. An example of a fruit-specific transcriptional initiation region is the one referred to as 2A11 which regulates the expression of a 2A11 cDNA sequence described in the Experimental section. The 2A11 transcriptional initiation region provides for an abundant messenger, being activated at or shortly after anthesis and remaining active until the red fruit stage. The expressed protein is a sulfur-rich protein similar to other plant storage proteins in sulfur content and size.

Also of interest is a transcriptional initiation region which regulates expression of the enzyme polygalacturonase, an enzyme which plays an important role in fruit softening and/or rotting. The polygalacturonase promoter is active in at least the breaker through red fruit stage in tomato fruit.

Any structural gene of interest may be employed for use in the construct. In many instances, it will be desirable to have another structural gene to serve as a marker associated with the construct, so that one can detect those plant cells in which the foreign gene has been stably introduced. For the most part, these constructs will have the following formula:

$$(T^1)_a\text{-}P^1\text{-}(S.G.)^1\text{-}Te^1) - (P^2\text{-}(S.G.)^2\text{-}Te^2)\text{-} (T^2)_b$$

wherein:
all of the symbols have the same functional definition except that the superscripts for P and Te intend that the promoter and terminator regions may be the same or different, where one is a marker and the other is a structural gene of interest. Of course, one may provide for a string of expression constructs having a plurality of the same or different genes in the construct. Thus, the presence of only two genes flanked by the T-DNA is merely illustrative.

As markers for structural genes, one can employ antibiotic resistance genes, e.g., a kanamycin resistance gene or methotrexate resistance gene (DHFR). These genes are described in Haas and Dowding, supra. Other markers include resistance to a biocide, particularly an antibiotic, such as G418, bleomycin, hygromycin, chloramphenicol, or the like. The particular market employed will be one which will allow for selection of transformed cells as compared to cells lacking the DNA which has been introduced.

The structural gene of interest may be any gene, either native, mutant native, or foreign to the plant host, and may be provided in a sense or antisense orientation. For native and mutant genes, the gene may provide for increased capability of protein storage, improved nutrient source, enhanced response to light, enhanced dehydration resistance, e.g., to heat, salinity or osmotic pressure, herbicide resistance, e.g., glyphosate, or the like. Foreign genes may include enhancement of native capabilities, herbicide resistance, resistance to various pests, such as viruses, insects, bacteria or fungi, production of foreign products, as a result of expression of one or more foreign genes, or the like.

In preparing the cassette construct, the various DNA sequences may normally be inserted or substituted into a bacterial plasmid. Any convenient plasmid may be employed, which will be characterized by having a bacterial replication system, a marker which allows for selection in the bacterium and generally one or more unique, conveniently located restriction sites. These plasmids, referred to as vectors, may include such vestors as pACYC184, pACYC177, pBR322, pUC9, the particular plasmid being chosen based on the nature of the markers, the availability of convenient restriction sites, copy number, and the like. Thus, the sequence may be inserted into the vector at an appropriate restriction site(s), the resulting plasmid used to transform the E. coli host, the E. coli grown in an appropriate nutrient medium and the cells harvested and lysed and the plasmid recovered. One then defines a strategy which allows for the stepwise combination of the different fragments.

As necessary, the fragments may be modified by employing synthetic adapters, adding linkers, employing in vitro mutagenesis or primer repair to introduce specific changes in the sequence, which may allow for the introduction of a desired restriction site, for removing superfluous base pairs, or the like. By appropriate strategies, one desires to minimize the number of manipulations required as well as the degree of selection required at each stage of manipulation. After each manipulation, the vector containing the manipulated DNA may be cloned, the clones containing the desired sequence isolated, and the vector isolated and purified. As appropriate, hybridization, restriction mapping or sequencing may be employed at each stage to ensure the integrity and correctness of the sequence.

The cassette constructs may be introduced into the plant host cell in a variety of ways, such as an insertion into a tumor- or gall-producing plasmid, as bare DNA, as an insertion in a plant DNA virus such as *A. tumefaciens* or *A. rhizogenes* as the transforming agent, protoplast fusion, injection, electroporation, etc. For transformation with Agrobacterium, plasmids can be prepared in *E. coli* which plasmids contain DNA homologous with the Ti-plasmid, particularly T-DNA. The plasmid may or may not be capable of replication in Agrobacterium, that is, it may or may not have a broad spectrum prokaryotic replication system, e.g., RK290, depending in part upon whether the transcription construct is to be integrated into the Ti-plasmid or be retained on an independent plasmid. By means of a helper plasmid, the transcription construct may be transferred to the *A. tumefaciens* and the resulting transformed organism used for transforming plant cells.

Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated and avoid hopping.

Conveniently, explants may be cultivated with *A. tumefaciens* or *A. rhizogenes* to allow for transfer of the expression cassette to the plant cells, the plant cells dispersed in an appropriate selective medium for selection, grown to callus, shoots grown and plantlets regenerated from the shoots by growing in rooting medium. The Agrobacterium host will contain a plasmid having the vir genes necessary for transfer of the T-DNA to the plant cells and may or may not have T-DNA. For injection and electroporation, disarmed Ti-plasmids (lacking the tumor genes, particularly the T-DNA region) may be used to introduce genes into the plant cell.

In accordance with the subject invention, an efficient procedure is provided for introduction of foreign DNA into plant cells with integration of the DNA and without gall formation, particularly as to plants which previously have been reported to be outside the host range of Agrobacterium. For a list of plant genera and species which are hosts and non-hosts for Agrobacterium, see De Cleene and Le Ley, *The Botanical Review* (1976) 42:389–466. Of particular interest in the subject invention are dicotyledon legumes, such as soybean, and monocotyledon grains, such as corn, rice, wheat, barley and oats.

Where a tumor- or gall-producing plasmid, e.g., the Ri-or Ti-plasmid, is to be used to introduce the cassette into the plant cell, a binary plasmid, which includes an Agrobacterium functional replication system, or bacterial mating may be employed, whereby the cassette-carrying plasmid is transferred from a compatible bacterium to *A. rhizogenes* or *A. tumefaciens* and the transconjugant isolated and analyzed for integration of the cassette into the Ri- or Ti-plasmid. This can be readily determined by various techniques, such as Southern analysis.

The Ti- or Ri-plasmid which is employed should be capable of providing for integration of T-DNA in the host without observable symptoms of tumor or gall formation. Thus, the plasmid which is selected may be tumor-producing in a conventional host, but will not produce tumors in plants normally considered not to be hosts. An illustrative plasmid is pTiA6, a wild-type plasmid. The *A. rhizogenes* or *A. tumefaciens* bacteria containing the cassette and the Ri- or Ti-plasmid may now be used for transformation of a plant host cell.

For transformation particularly of monocotyledenous or leguminous plants, the subject method employs in vitro grown seedlings between green V-E and V-1 (Fehr and Caviness, 1977, Stages of Soybean Development. Iowa State Coop. Ext. Serv., Agric. and Home Econ. Expt. Stn. Special Report 80). Thus, young plants, the hypocotyl or next leaf are employed. The Agrobacterium cells are injected into the plant tissue. Generally about 1–5 $\mu$l of $1 \times 10^6$ to $1 \times 10^8$ cells/ml will be injected. Injection of Agrobacterium into cotyledons, nodes and internodes causes a visible necrosis around the wound site. No tumor formation is observed.

After about one to three weeks, the explants are excised from the tissue surrounding the site of injection and subcultured in a hormone lacking medium. Callus is observed to grow from some of the explants. Opine is present in these tissues, while none is detected in non-transformed callus.

Transformation of seed crops such as Brassica can be by any of a variety of methods known to those skilled in the art. See, for example, Radke et al. (1988) Theor. Appl. Genet. 75:685–694 and Radke et al. (1992) *Plant Cell Reports* 11:499–505.

The cells which have been transformed may be grown into plants in accordance with conventional ways. See, for example, McCormick et al., *Plant Cell Reports* (1986) 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then fruits or seeds harvested to ensure the desired phenotype or other property has been achieved.

As a host cell, any plant variety may be employed which provides a plant part or tissue of interest. For example, where the plant tissue of interest is seed, for the most part, plants will be chosen where the seed is produced in high amounts or a seed-specific product of interest is involved. Seeds of interest include the oil seeds, such as the Brassica seeds, cotton seeds, soybean, safflower, sunflower, or the like; grain seeds, e.g., wheat, barley, rice, clover, corn, or the like.

Where the plant part is a fruit, any of a number of fruit bearing plants may be employed in which the plant parts of interest are derived from the ovary wall. These include true berries such as tomato, grape, blueberry, cranberry, currant, and eggplant; stone fruits (drupes) such as cherry, plum, apricot, peach, nectarine and avocado; compound fruits (droplets) such as raspberry and blackberry. In hesperidium (oranges, citrus), the expression cassette might be expected to be expressed in the "juicy" portion of the fruit. In pepos (such as watermelon, cantaloupe, honeydew, cucumber and squash) the equivalent tissue for expression is most likely the inner edible portions, whereas in legumes (such as peas, green beans, soybeans) the equivalent tissue is the seed pod.

By use of transcription initiation regions from regulated genes, it is found that expression of a structural gene of interest, either sense or antisense, can be regulated in a manner similar to the regulation of the gene native to the transcription initiation region. For example, by use the soybean SSU promoter, the expression of a gene under the control of this promoter is induced by light. Thus, the expression of the gene is regulatable, where enhanced expression occurs during irradiation with light, while substantially reduced expression or no expression occurs in the absence of light. Similarly, transcription initiation regions from genes expressed preferentially in seed or fruit tissues may be used to control of expression of desired DNA sequences in these plant tissues.

By virtue of having a regulatable promoter in the soybean plant, one can provide for protection against herbicides, by providing a herbicide-resistant gene to be under the regulatable control of the SSU promoter. For example, by employing a mutated aroA gene, the enzyme 5-enolpyruvyl-3-phosphoshikimate synthase which is glyphosateresistant can be produced under light induction. Thus, the soybean plant may be protected from glyphosate, allowing for the killing of weeds employing the glyphosate herbicide. While glyphosate may be used by itself, particularly for pre-emergent spraying and post-emergent control of weeds, the glyphosate may also be used with other post-emergent broadleaf herbicides, such as Basagran (bentazan), Tackle/Blazer (aciflurofen). Normally, applications will vary from about 1.25 to 1.5 lbs/acre, where the herbicides may be formulated as dry or wet formulations, by themselves or in combination with other additives, such as sticking agents, spreading agents, stabilizers, or the like. Inert powders may be used with dry formulations.

A transcriptional initiation region may be used for varying the phenotype of the seeds. Various changes in phenotype are of interest. These include modifying the fatty acid composition in seeds, that is changing the ratio and/or amounts of the various fatty acids, as to length, unsaturation, or the like. Thus, the fatty acid composition may be varied by enhancing the fatty acids of from 10 to 14 carbon atoms as compared to the fatty acids of from 16 to 18 carbon atoms, increasing or decreasing fatty acids of from 20 to 24 carbon atoms, providing for an enhanced proportion of fatty acids which are saturated or unsaturated, or the like. These results can be achieved by providing for reduction of expression of one or more endogenous products, particularly enzymes or cofactors, by producing a transcription product which is complementary to the transcription product of a native gene, so as to inhibit the maturation and/or expression of the transcription product, or providing for expression of a gene, either endogenous or exogenous, associated with fatty acid synthesis. Expression products associated with fatty acid synthesis include acyl carrier protein, acyl-ACP thioesterase, acetyl-CoA ACP transacylase, acetyl-CoA carboxylase, ketoacyl-ACP synthases, malonyl-CoA ACP transacylase, stearoyl-ACP desaturase, and other desaturase enzymes.

A transcriptional initiation region may be employed for varying the phenotype of the fruit. Various changes in phenotype are of interest. These changes may include up- or down-regulation of formation of a particular saccharide, involving mono- or polysaccharides, involving such enzymes as polygalacturonase, levansucrase, dextransucrase, invertase, etc.; enhance lycopene biosynthesis; cytokinin and monellin synthesis. Other properties of interest for modification include response to stress, organisms, herbicides, bruising, mechanical agitation, etc., change in growth regulators, organoleptic properties, etc. For antisense or complementary sequence transcription, the sequence will usually be at least 12, more usually at least 16 nt. Antisense sequences of interest include those of polygalacturonase, sucrase synthase and invertase.

Alternatively, one may provide various products from other sources including mammals, such as blood factors, lymphokines, colony stimulating factors, interferons, plasminogen activators, enzymes, e.g. superoxide dismutase, chymosin, etc., hormones, rat mammary thioesterase 2, phospholipid acyl desaturases involved in the synthesis of eicosapentaenoic acid, and human serum albumin. The level of seed proteins, particularly mutated seed proteins, having an improved amino acid distribution which would be better suited to the nutrient value of the seed can also be increased. This can be achieved, for example, by inhibition of the native seed protein by producing a complementary DNA sequence to the native coding region or non-coding region, where the complementary sequence does not hybridize efficiently to the mutated sequence, or inactivates the native transcriptional capability.

A protein is provided having the sequence described in the Experimental section designated as 2A11. This protein could be a storage protein and be useful in enhancing sulfur containing amino acids (cysteine and methionine) in the diet. It can be obtained in substantially pure form by providing for expression in prokaryotes or eukaryotes, e.g., yeast by inserting the open reading frame into an expression cassette containing a transcriptional initiation region. A variety of expression cassettes are commercially available or have been described in the literature. See, for example, U.S. Pat. Nos. 4,532,207; 4,546,082; 4,551,433; and 4,559,302. The product, if intracellular, may be isolated by lysing of the cells and purification of the protein using electrophoresis, affinity chromatography, HPLC extraction, or the like. The product may be isolated in substantially pure form free of other plant products, generally having at least about 95% purity, usually at least about 99% purity.

The following examples are offered by way of illustration and not by limitation.

The following examples are offered by way of illustration and not by way of limitation.

EXAMPLES

Cloning Vectors

Cloning vectors used include the pUC vectors, pUC8 and pUC9 (Vieira and Messing, *Gene* (1982) 19:259–268); pUC18 and pUC19 (Norrander et al., *Gene* (1983) 26:101–106; Yanisch-Perron et al., *Gene* (1985) 33:103–119), and analogous vectors exchanging chloramphenicol resistance (CAM) as a marker for the ampicillin resistance of the pUC plasmids described above (pUC-CAM [pUC12-Cm, pUC13-Cm] Buckley, K., Ph.D. Thesis, U.C.S.D., CA 1985). The multiple cloning sites of pUC18 and pUC19 vectors were exchanged with those of PUC-CAM to create pCGN565 and pCGN566 which are CAM resistant. Also used were pUC118 and pUC119, which are respectively, pUC18 and pUC19 with the intergenic region of M13, from an HgiAI site at 5465 to the AhaIII site at 5941, inserted at the NdeI site of pUC (available from Vieira J. and Messing, J. Waksman Institute, Rutgers University, Rutgers, N.J.)

Materials

Terminal deoxynucleotide transferase (TDT), RNaseH, *E. coli* DNA polymerase, T4 kinase, and restriction enzymes were obtained from Bethesda Research Laboratories; *E. coli* DNA ligase was obtained from New England Biolabs; reverse transcriptase was obtained from Life Sciences, Inc.; isotopes were obtained from Amersham; X-gal was obtained from Bachem, Inc., Torrance, Calif.

Bacterial strains, plasmids, and media

*E. coli* strains MM294 (F endA1 hsdR17 supE44 thi⁻1) (Meselson and Yuan, *Nature* (1968) 217:1110–1114) and 71-18 (Δlac-proAB) supE thi F'lacI$^q$ Z M15 proA$^+$B$^+$) (Messing et al., *Proc. Natl. Acad. Sci. USA* (1977) 74:3642–3646) were routinely used for transformations. *A. tumefaciens* A348 contains the octopine Ti-plasmid pTiA6 in A114 (Garfinkel and Nester, *J. Bacteriol.* (1980) 144:732–743). pRK2073 was maintained in HB101 (F hsd$^3$20 (r$_B$-r$_m$-) recA13 proA2 lacY1 leuB6 rpsL20 thi 1 supE44) (Boyer and Rouland-Dussiox, *J. Mol. Biol.* (1969) 41:459).

Plasmid pRK2073 was generated by insertion of Tn7 into the Kan$^r$ gene of pRK2013. (Ditta et al., *Proc. Natl. Acad. Sci. USA* (1980) 76:1648–1652) pSR2.1 (Berry-Lowe et al., 1982, supra.) contains a 2.1 EcoRI fragment of a soybean small subunit gene (SSU) in pBR325. The Bam19 fragment of pTiA6 was maintained as a 4.6 kb subclone in pBR325 (pNM33C-19-1) (Thomashow et al., *Cell* (1980) 19:729–739). pCGN464 contained the 1.5 kb HindIII-SalI fragment of Tn5 cloned into the sp6 transcription vector pSP65 (Melton et al., *Nucl. Acids Res.* (1984) 12:7035–7056). The pUC7 recombinant vector containing the 1.0 kb BglII-SmaI fragment of Tn5(pCGN546) is designated pCGN546.

*E. coli* were grown on LB media (Miller, 1972, *Experiments in Molecular Genetics*, CSH Laboratory, Cold Spring Harbor, N.Y.). *A. tumefaciens* were grown in either minimal AB medium (Chilton et al., *Proc. Natl. Acad. Sci. USA* (1974) 71:3672–3676) or in MG/L (50% LB: 50% mannitolglutamate medium (Roberts and Kerr, *Physiol. Plant Pathol.* (1974) 4:81–91.

*E. coli* strain pCGN1299×7118 was deposited with the American Type Culture Collection (A.T.C.C.), 12301 Parklawn Drive, Rockville, Md., 20852 on May 21, 1987 and given Accession No. 67408.

Example 1

Preparation of Transformed Soybean Plants

Soybean (glycine max cv "forrest") seeds were surface sterilized (12 min, 5% sodium hypochlorite, 0.1% Tween 80), washed 3 times in distilled water and germinated aseptically (1/10 MS-Gibco, 0.6% phytagar (Gibco) medium without hormones, 25° C. red light (Grolux 40W).). Agrobacterium containing strains pTiCGN327 and pTiCGN609 were grown overnight (MG/L medium 30° C.) were injected into hypocotyl, cotyledons, node and internode of two to three week old seedlings. Three weeks after injection, tissues surrounding the injection site were excised and placed on 0.6% phytagar MS medium deprived of hormones and containing 0.5 g/L carbenicillin. Hormone independent, octopine positive tissues were then transferred to liquid MS medium and analyzed for the presence of octopine (Otten and Schilperoot, *Biochem. et Biophys.* Acta 1978) 527:497–500). To determine kanamycin resistance, growing calli were then placed in light or complete darkness. Friable calli of light grown or dark grown 327 and 609 were disaggregated by filtering through a 105 μ nylon mesh. Samples (0.1 ml packed cell volume (p.c.v.)) of fine suspensions (1–15 cells/clump were placed in the same medium containing 0 to 300 mg/L kanamycin. Pigmented cells were kept in the light while the non-pigmented cells were kept in total darkness. The effects of kanamycin on growth were measured as packed cell volume six weeks later.

DNA Isolation

The alkali-lysis procedure of Ish-Horowitz (Maniatis et al., 21982 *Molecular Cloning*, A Laboratory Manual, CSH Laboratory, Cold Spring Harbor, N.Y.) was used for both large-scale plasmid isolation and for mini-prep analysis. Total DNA from A. tumefaciens was prepared as described (Currier and Nester, *J. Bacteriol.* (1976) 126:157–165.

DNA fragments were isolated from low melt agarose gels (Sea Plaque) run in TAE buffer (0.04M Tris-acetate, 0.002M EDTA (Maniatis, supra.) without ethidium bromide. The desired fragment was extracted from the excised agarose band by melting at 65° C. for 30 min followed by phenol extraction and ethanol precipitation.

Cloning Procedures

Restriction enzyme digestions and ligations were performed according to manufacturer's instructions. Klenow fill-in reactions and transformation were as described (Maniatis, supra.) When pUC9 was being transformed into *E. coli* strain 71-18, X-Gal and IPTG were added to the plates as described (Miller, 1972, supra). Correct insertion and orientation of recombinants were verified by 2 to 3 restriction digests.

The verification of the SmaI-DdeI junction in pCGN606 was done by cloning the 1.1 kb BamHi-EcoRI fragment into M13mp9 (Maniatis, supra). Sequence analysis was then performed in accordance with conventional ways.

Agrobacterium matings

The pCGN609 construct was integrated into the Tiplasmid pTiA6 in a three-way mating (Comai et al., 1983, supra). Overnight E. Coli strains containing cultures of pCGN609 and pRK2073, respectively, were mixed with A. tumefaciens strain A722 and spread on AB plates containing 150 μg/ml kanamycin and 250 μg/ml streptomycin. Single colonies were restreaked twice. Correct integration was verified by Southern analysis of total Agrobacterium DNA. BamHI digested DNA was probed with a nick-translated 2.5 PstI-EcoRI 3' ocs fragment from pCGN607. Southern analysis and nick translation were performed in accordance with conventional ways.

RNA preparation and Northern blot analysis

RNA was prepared from soybean callus by a modification of the guanidine thiocyanate procedure of Colbert et al. (*Proc. Natl. Acad. Sci. USA* (1983) 80:2248–2252) in which the extraction buffer contain 4M guanidine thiocyanate, 2% lauryl sarcosine, 1% β-mercaptoethanol, 50 mM Tris, pH 7.5 20 mM EDTA, 1 mM aurintricarboxylic acid, 0.4% antifoam A (Sigma). PolyA$^+$ RNA was purified over oligo-dT cellulose (Maniatis, supra.) and Northern gels run as previously described (Shewmaker et al., 1984, supra). $^{32}$p-RNA bacterial amioglycoside phosphotransferase mRNA complementary to (APH(3')II-mRNA) (Herrera-Estrella et al., *EMBO J.* (1983) 2:987–995; Bevan et al., *Nature* (1983) 304:184–187) was synthesized from BglII cut pCGN464 using a riboprobe kit (ProMega Biotech) according to the manufacturer's instructions. The hybridization buffers were as suggested by the riboprobe manufacturer's with hybridization at 55° C. and washes at 60° C.

Kanamycin activity blots

The kanamycin activity blots (Reiss et al., *Gene* (1984) 30:211) were performed as modified for plants (Schreier et al., *EMBO J.* (1985)4(1):25–32). For each sample, 0.2 g of fresh soybean callus was used.

Construction of soybean ssu-Kan$^r$ chimera

A soybean SSU gene (Berry-Lowe), 1982, supra) was chosen as the source of the 5'-promoter region. In this gene there is a DdeI site, 9 pb upstream of the AUG. A DdeI digest of pSRS2.1 (Berry-Lowe, 1982, supra.) yielded a 1.1 kd 5' fragment isolated out of a low melt agarose gel. The 5' 1.1 kb DdeI fragment was filled in with Klenow polymerase and ligated into SmaI digested pUC9 (Vieira and Messing, *Gene* (1982) 19:259). A clone, pCGN606 was obtained that had the SSU promoter facing the adjacent EcoRI site of pUC9.

A cassette containing the soybean 5' region and an appropriate 3' region was then constructed. For this cassette, the octopine synthetase (ocs) 3' region was chosen as a 2.5 kb EcoRI-PstI fragment from a Bam19 subclone of pTiA6 (Thomashow, 1980, supra). Since it contained regions homologous to T-DNA, it would facilitate transfer to the Tiplasmid of Agrobacterium. The cassette pCGN607 was obtained in a 3-way ligation with this fragment, the 1.1 kb BamHI-EcoRI 5' soybean SSU fragment from pCGN606, and the 2.7 kb BamHI-PstI fragment of pACYC177 (Chang and Cohen, *J. Bacteriol.* (1978) 134:1141).

The APH(3')-II gene employed was from Tn5, which confers resistance to kanamycin both in bacteria (Haas and Dowding, Meth. *Enzymology* (1975) 43:611–628) and plants (Herrera-Estrella, 1983, supra). A 1.0 kb BglII-SmaI fragment containing the gene was cloned into pUC7 resulting in adjacent flanking EcoRI restriction sites. The plasmid was digested to provide a 1.0 kb EcoRI fragment and this fragment ligated into EcoRI digested pCGN607. Clones were screened for those carrying the Kan$^r$ gene of Tn5 in the correction orientation. One of the clones which had the correct orientation was designated pCGN609. The plasmid also carried the kanamycin resistance gene from pACYC177 (APH(3')-I as a bacterial marker. These two kanamycin resistance genes (APH(3')-I and -II) do not cross-hybridize at the nucleic acid level.

Following Klenow polymerase fill-in, only 9 bp which are present upstream of the AUG in native soybean SSU are lacking in pCGN609. These 9 bp are replaced with 46 bp that arise from the fusion manipulations. The rest of the 1.1 kb soybean SSU 5' region is the same in pCGN609 as in native soybean.

The integration of pCGN609 into the Ti-plasmid pTiA6 was accomplished in a three-way (Comai et al., 1983) mating with pRK2073. Correct integration was verified by Southern analysis of the resulting Agrobacterium, designated pTiCGN609. In the integration an intact octopine synthetase region is maintained as evidenced by the detection of octopine. Octopine was detected by fluorescence of its phenanthroquinone adduct following paper electrophoresis of tissue extracts (10 mg).

Transformation of soybean

Transformation of soybean was performed on in vitro grown seedlings from the time their cotyledons turned green up to the time of the appearance of the second internode. In every case, the injection of Agrobacterium caused a clearly visible necrosis around the wound site. Occasionally, after 1 to 3 weeks, roots would appear at the inoculation site. Splitting also occurred, revealing swollen tissue, but in no case was tumor noted with the Agrobacterium strains used. Explants excised from the tissue surrounding the site of injection were subcultured in MS medium deprived of hormones, 0.6% phytagar, 0.5 g/L carbenicillin. Hormone-independent callus grew from some of the explants. Hormone-independent growing tissue for the presence of octopine was positive, while no octopine was detected in non-transformed soybean tissue. All aerial parts of the soybean seedlings, cotyledons, internodes, and nodes, were able to produce transformed tissue although no systematic study was done to determine which of these areas is most susceptible to Agrobacterium.

Analysis of polyA$^+$ RNA in light and dark grown tissue

The increase in SSU protein seen in a number of light grown plants was shown to correlate with an increase in the level of SSU polyA$^+$ RNA. Northern analysis of light and dark grown 609 soybean callus was performed to determine if an increase in APH(3')-II polyA$^+$ RNA occurred with growth in light. The results were determined with a $^{32}$P-RNA probe specific for APH(3')-II transcript in the sense orientation. An RNA of the expected size of approximately 1.6 kb was seen in both cases of light and dark. Approximately 5–10 times as much transcript was seen in the light grown tissue as the dark grown tissue.

Presence of protein with kanamycin phosphotransferase activity

APH(3')-II (aminoglycoside phosphotransferase) inactivates kanamycin by phosphorylation. The presence of this activity can be demonstrated by a number of assays which measure the phosphorylation of kanamycin in vitro. In the assay employed (Reiss et al., *Gene* (1984) 30:211) extracts are run on an acrylamide gel, reacted in situ with kanamycin and γ-$^{32}$P-ATP and then blotted to P81 (phosphocellulose) paper. For green (light grown) and white (dark grown) 609 soybean callus, activity was seen in the green soybean at the same mobility as that observed for purified APH(3')-II, while no detectable activity was seen in white 609 tissue or in soybean transformed with an Agrobacterium lacking the APH(3')-II gene.

Demonstration of kanamycin resistance in the transformed tissue

Greening of the soybean callus occurred spontaneously after exposure to light. Some of the green 609 callus selected for its friability was disaggregated as described previously and used to analyze its resistance to kanamycin. It was compared to similar non-pigmented tissue grown in complete darkness. Dark grown 609 as well as control 327 tissue died in the presence of 50 mg/L kanamycin, while the light grown tissue could survive up to 300 mg/L kanamycin although its growth was slightly inhibited at this concentration.

Example 2

Construction of a Napin Promoter

There are 298 nucleotides upstream of the ATG start codon of the napin gene on the pgN1 clone, a 3.3 kb EcoRI fragment of *B. napus* genomic DNA containing a napin gene cloned into pUC8 (available from Marti Crouch, University of Indiana). pgN1 DNA was digested with EcoRI and SstI and ligated to EcoRI/SstI digested pCGN706. (pCGN706 is an XhoI/PstI fragment containing 3' and polyadenylation sequences of another napin cDNA clone pN2 (Crouch et al., 1983 supra) cloned in pCGN566 at the SalI and PstI sites.) The resulting clone pCGN707 was digested with SalI and treated with the enzyme Bal31 to remove some of the coding region of the napin gene. The resulting resected DNA was digested with SmaI after the Bal31 treatment and religated. One of the clones, pCGN713, selected by size, was subcloned by EcoRI and BamHI digestion into both EcoRI-BamHI digested pEMBL18 (Dente et al., *Nucleic Acids Res.* (1983) 11:1645–1655) and pUC118 to give E418 and E4118 respectively. The extent of Bal31 digestion was confirmed by Sanger dideoxy sequencing of E418 template. The Bal31 deletion of the promoter region extended only to 57 nucleotides downstream of the start codon, thus containing the 5' end of the napin coding sequence and about 300 bp of the 5' non-coding region. E4118 was tailored to delete all of the coding region of napin including the ATG start codon by in vitro mutagenesis by the method of Zoller and Smith (*Nucleic Acids Res.* (1982) 10:6487–6500) using an oligonucleotide primer 5'-GATGTTTTGTATGTGGGCCCCTAGGAGATC-3'. Screening for the appropriate mutant was done by two transformations into *E. coli* strain JM83 (Messing J., In: Recombinant DNA Technical Bulletin, NIH Publication No. 79–99, 2 No. 2, 1979, pp 43–48) and SmaI digestion of putative transformants. The resulting napin promoter clone is pCGN778 and contains 298 nucleotides from the EcoRI site of pgN1 to the A nucleotide just before the ATG start codon of napin. The promoter region was subcloned into a chloramphenicol resistant background by digestion with EcoRI and BamHI and ligation to EcoRI-BamHI digested pCGN565 to give pCGN779c.

Extension of the Napin Promoter Clone pCGN779c contains only 298 nucleotides of potential 5'-regulatory sequence. The napin promoter was extended with a 1.8 kb fragment found upstream of the 5'-EcoRI site on the original λBnNa clone. The ~3.5 kb XhoI fragment of λBnNa (available from M. Crouch), which includes the napin region, was subcloned into SalI-digested pUC119 to give pCGN930. A HindIII site close to a 5' XhoI site was used to subclone the HindIII-EcoRI fragment of pCGN930 into HindIII-EcoRI digested Bluescript+(Vector Cloning Systems, San Diego, Calif.) to give pCGN942. An extended napin promoter was made by ligating pCGN779c digested with EcoRI and PstI and pCGN942 digested with EcoRI and PstI to make pCGN943. This promoter contains ~2.1 kb of sequence upstream of the original ATG of the napin gene contained on λBnNa. A partial sequence of the promoter region is shown in FIG. 1.

Napin Cassettes

The extended napin promoter and a napin 3' regulatory region are combined to make a napin cassette for expressing genes seed-specifically. The napin 3'-region used is from the plasmid pCGN1924 containing the XhoI-EcoRI fragment from pgN1 (XhoI site is located 18 nucleotides from the stop codon of the napin gene) subcloned into EcoRi-SalI digested pCGN565. HindIII-PstI digested pCGN943 and pCGN1924 are ligated to make the napin cassette pCGN944, with unique cloning sites SmaI, SalI, and PstI for inserting genes Construction of cDNA Library from Spinach Leaves Total RNA was extracted from young spinach leaves in 4M guanidine thiocyanate buffer as described by Facciotti et al. (*Biotechnology* (1985) 3:241–246). Total RNA was subjected to oligo(dT)-cellulose column chromatography two times to yield poly(A)$^+$ RNA as described by Maniatis et al., (1982) Molecular Cloning: A Laboratory Manual, Cold Spring Harbor Laboratory, New York. A cDNA library was constructed in pUC13-Cm according to the method of Gubler and Hoffman, (*Gene* (1983) 25:263–269) with slight modifications. RNasin was omitted in the synthesis of first strand cDNA as it interfered with second strand synthesis if not completely removed, and dCTP was used to tail the vector DNA and dGTP to tail double-stranded cDNA instead of the reverse as described in the paper. The annealed cDNA was transformed to competent *E. coli* JM83 (Messing (1979) supra) cells according to Hanahan (*J. Mol. Biol.* (1983) 166:557–580) and spread onto LB agar plates (Miller (1972) Experiments in Molecular Genetics. Cold Spring Harbor Laboratory, Cold Spring Harbor, N.Y.) containing 50 μg/ml chloramphenicol and 0.005 % X-Gal.

Identification of Spinach ACP-I cDNA

A total of approximately 8000 cDNA clones were screened by performing Southern blots (Southern, *J. Mol. Biol.* (1975) 98:503) and dot blot (described below) hybridizations with clone analysis DNA from 40 pools representing 200 cDNA clones each (see below). A 5' end-labeled synthetic oligonucleotide (ACPP4) that is at least 66% homologous with a 16 amino acid region of spinach ACP-I (5'-GATGTCTTGAGCCTTGTCCTCATCCACATTGAT ACCAAACTCCTCCTC-3') is the complement to a DNA sequence that could encode the 16 amino acid peptide glu-glu-glu-phe-gly-ile-asn-val-asp-glu-asp-lys-ala-gln-asp-ile, residues 49–64 of spinach ACP-I (Kuo and Ohlrogge, *Arch. Biochem. Biophys.* (1984) 234:290–296) and eas used for an ACP probe.

Clone analysis DNA for Southern and dot blot hybridizations was prepared as follows. Transformants were transferred from agar plates to LB containing 50 μg/ml chloramphenicol in groups of ten clones per 10 ml media. Cultures were incubated overnight in a 37° C. shaking incubator and then diluted with an equal volume of media and allowed to grow for 5 more hours. Pools of 200 cDNA clones each were obtained by mixing contents of 20 samples. DNA was extracted from these cells as described by Birnboim and Doly (*Nucleic Acids Res.* (1979) 7:1513–1523). DNA was purified to enable digestion with restriction enzymes by extractions with phenol and chloroform followed by ethanol precipitation. DNA was resuspended in sterile, distilled water and 1 μg of each of the 40 pooled DNA samples was digested with EcoRI and HindIII and electrophoresed through 0.7% agarose gels. DNA was transferred to nitrocellulose filters following the blot hybridization technique of Southern.

ACPP4 was 5' end-labeled using γ³²P dATP and T4 kinase according to the manufacturer's specifications. Nitrocellulose filters from Southern blot transfer of clone analysis DNA were hybridized (24 hours, 42° C.) and washed according to Berent et al. (*BioTechniques* (1985) 3:208–220). Dot blots of the same set of DNA pools were prepared by applying 1 μg of each DNA pool to nylon membrane filters in 0.5 M NaOH. These blots were hybridized with the probe for 24 hours at 42° C. in 50% formamide/1% SDS/1 M NaCl, and washed at room temperature in 2× SSC/0.1% SDS (1× SSC=0.15M NaCl; 0.015M Na citrate; SDS-sodium dodecylsulfate). DNA from the pool which was hybridized by the ACPP4 oligoprobe was transformed to JM83 cells and plated as above to yield individual transformants. Dot blots of these individual cDNA clones were prepared by applying DNA to nitrocellulose filters which were hybridized with the ACPP4 oligonucleotide probe and analyzed using the same conditions as for the Southern blots of pooled DNA samples.

Nucleotide Sequence Analysis

The positive clone, pCGN1SOL, was analyzed by digestion with restriction enzymes and the following partial map was obtained.

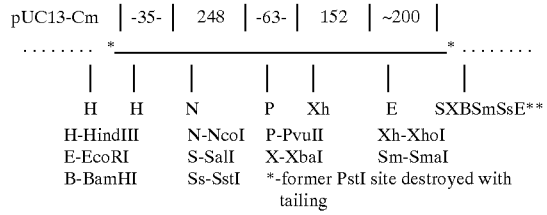

```
pUC13-Cm | -35- |  248  | -63- |  152  | ~200 |
........*_____*........
  |   |         |        |        |        |
  H   H         N        P       Xh        E      SXBSmSsE**
H-HindIII    N-NcoI   P-PvuII  Xh-XhoI
E-EcoRI      S-SalI   X-XbaI   Sm-SmaI
B-BamHI      Ss-SstI  *-former PstI site destroyed with
                       tailing
```

**polylinker with available restriction sites indicated

The cDNA clone was subcloned into pUC118 and pUC119 using standard laboratory techniques of restriction, ligation, transformation, and analysis (Maniatis et al., (1982) supra). Single-stranded DNA template was prepared and DNA sequence was determined using the Sanger dideoxy technique (Sanger et al., *Proc. Nat. Acad. Sci. USA* (1977) 74:5463–5467). Sequence analysis was performed using a software package from IntelliGenetics, Inc.

pCGN1SOL contains an (approximately) 700 bp cDNA insert including a stretch of A residues at the 3' terminus which represents the poly(A) tail of the mRNA. An ATG codon at position 61 is presumed to encode the MET translation initiation codon. This codon is the start of a 411 nucleotide open reading frame, of which, nucleotides 229–471 encode a protein whose amino acid sequence corresponds almost perfectly with the published amino acid sequence of ACP-I of Kuo and Ohlrogge supra as described previously. In addition to mature protein, the pCGN1SOL also encodes a 56 residue transit peptide sequence, as might be expected for a nuclear-encoded chloroplast protein.

Navin-ACP Construct pCGN796 was constructed by ligating pCGN1SOL digested with HindIII-BamHI, pUC8-CM digested with HindIII and BamHI and pUC118 digested with BamHI. The ACP gene from pCGN796 was transferred into a chloramphenicol background by digestion with BamHI and ligation with BamHI digested pCGN565. The resulting pcGN1902 was digested with EcoRI and SmaI and ligated to EcoRI-SmaI digested pUC118 to give pCGN1920. The ACP gene in pCGN1920 was digested at the NcoI site, filled in by treatment with the Klenow fragment, digested with SmaI and religated to form pCGN1919. This eliminated the 5'-coding sequences from the ACP gene and regenerated the ATG. This ACP gene was flanked with PstI sites by digesting pCGN1919 with EcoRI, filling in the site with the Klenow fragment and ligating a PstI linker. This clone is called pCGN945.

The ACP gene of pCGN945 was moved as BamHI-PstI fragment to pUC118 digested with BamHI and PstI to create pCGN945a so that a SmaI site (provided by the pUC118) would be at the 5'-end of the ACP sequences to facilitate cloning into the napin cassette pCGN944. pCGN945a digested with SmaI and PstI was ligated to pCGN944 digested with SmaI and PstI to produce the napin ACP cassette pCGN946. The napin ACP cassette was then transferred into the binary vector pCGN783 by cloning from the HindIII site to produce pCGN948.

Construction of the Binary Vector pCGN783 pCGN783 is a binary plasmid containing the left and right T-DNA borders of A. tumefaciens (Barker et al., *Plant Mol. Biol.* (1983) 2:335–350); the gentamicin resistance gene of pPH1JI (Hirsch et al., *Plasmid* (1984), 12:139–141) the 35S promoter of cauliflower mosaic virus (CaMV) (Gardner et al., *Nucleic Acids Res.* (1981) 9:2871–2890), the kanamycin resistance gene of Tn5 (Jorgenson et al., infra and Wolff et al., *Nucleic Acids Res.* (1985) 13:355–367) and the 3' region from transcript 7 of pTiA6 (Barker et al., (1983) supra).

To obtain the gentamicin resistance marker, the gentamicin resistance gene was isolated as a 3.1 kb EcoRI-PstI fragment of pPHIJl cloned into pUC9 yielding pCGN549. The HindIII-BamHI fragment containing the gentamicin resistance gene was substituted for the HindIII-BglII fragment of pCGN587 creating pCGN594.

pCGN587 was prepared as follows: The HindIII-SmaI fragment of Tn5 containing the entire structural gene for APHII (Jorgenson et al., *Mol. Gen. Genet.* (1979) 177:65) was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment containing the 3'-portion of the APHII gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a Sau3A-PstI fragment from the 5'-end of APHII, which fragment lacks the superfluous ATG, into the BamHI-PstI site of pCGN546W to provide plasmid pCGN550.

The EcoRI fragment containing the APHII gene was then cloned into the unique EcoRI site of pCGN451, which contains an octopine synthase cassette for expression, to provide pCGN552 (1ATG).

pCGN451 includes an octopine cassette which contains about 1556 bp of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows. A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-translated region, the mRNA cap site and 16 bp of the 5' non-translated region (to a BamHI site) intact. This small fragment was obtained by size fractionation on a 7% acrylamide gel and fragments approximately 130 bp long eluted.

This size fractionated DNA was ligated into M13mp9 and several clones sequenced and the sequence compared to the known sequence of the octopine synthase gene. The M13 construct was designated p14, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences.

The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence). pCGN451 also provides the right T-DNA border.

The resulting plasmid pCGN451 having the ocs 5' and the ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation.

This ocs/KAN gene was used to provide a selectable marker for the trans type binary vector pCGN587.

The 5' portion of the engineered octopine synthase promoter cassette consists of pTiA6 DNA from the XhoI at bp 15208-13644 (Barker's numbering), which also contains the T-DNA boundary sequence (border) implicated in T-DNA transfer. In the plasmid pCGN587, the ocs/KAN gene from pCGN552 provides a selectable marker as well as the right border. The left boundary region was first cloned in M13mp9 as a HindIII-SmaI piece (pCGN502) (base pairs 602-2213) and recloned as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglII fragment of pVCK102 (Knauf and Nester, *Plasmid* (1982) 8:45), creating pCGN585. By replacing the smaller SalI fragment of pCGN585 with the XhoI fragment from pCGN552 containing the ocs/KAN gene, pCGN587 was obtained.

The pCGN594 HindIII-BamHI region, which contains an 5'-ocs-kanamycin-ocs- 3' (ocs is octopine synthase with 5' designating the promoter region and 3' the terminator region, see U.S. application Ser. No. 775,923, filed Sep. 13, 1985) fragment was replaced with the HindIII-BamHI polylinker region from pUC18.

pCGN566 contains the EcoRI-HindIII linker of pUC18 inserted into the EcoRI-HindIII sites of pUC13-Cm. The HindIII-BglII fragment of pNW31C-8,29-1 (Thomashow et al., *Cell* (1980) 19:729) containing ORF1 and −2 of pTiA6 was subcloned into the HindIII-BamHI sites of pCGN566 producing pCGN703.

The Sau3A fragment of pCGN703 containing the 3' region of transcript 7 (corresponding to bases 2396–2920 of pTiA6 (Barker et al., (1983) supra) was subcloned into the BamHI site of pUC18 producing pCGN709. The EcoRI-SmaI polylinker region of pCGN709 was substituted with the EcoRI-SmaI fragment of pCGN587, which contains the kanamycin resistance gene (APH3-II) producing pCGN726.

The EcoRI-SalI fragment of pCGN726 plus the BglII-EcoRI fragment of pCGN734 were inserted into the BamHI-SalI site of pUC8-Cm producing pCGN738. pCGN726c is derived from pCGN738 by deleting the 900 bp EcoRI-EcoRI fragment.

To construct pCGN167, the AluI fragment of CaMV (bp 7144–7735) (Gardner et al., *Nucl. Acid Res.* (1981) 9:2871–2888) was obtained by digestion with AluI and cloned into the HincII site of M13mp7 (Messing et al., *Nucl. Acids Res.* (1981) 9:309–321) to create C614. An EcoRI digest of C614 produced the EcoRI fragment from C614 containing the 35S promoter which was cloned into the EcoRI site-of pUC8 (Vieira and Messing, *Gene* (1982) 19:259) to produce pCGN146.

To trim the promoter region, the BglII site (bp 7670) was treated with BglII and resected with Bal31 and subsequently a BglII linker was attached to the Bal31 treated DNA to produce pCGN147.

pCGN148a containing a promoter region, selectable marker (KAN with 2 ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141–1156). pCGN526 was made by inserting the BamHI fragment 19 of pTiA6 (Thomashow et al., *Cell* (1980) 19:729–739), modified with XhoI linkers inserted into the SmaI site, into the BamHI site of pCGN525. pCGN528 was obtained by deleting the small XhoI fragment from pCGN526 by digesting with XhoI and religating.

pCGN149a was made by cloning the BamHI-kanamycin gene fragment from pMB9KanXXI into the BamHI site of pCGN148a.

pMB9KanXXI is a pUC4K variant (Vieira and Messing, *Gene* (1982) 19:259–268) which has the XhoI site missing but contains a functional kanamycin gene from Tn903 to allow for efficient selection in Agrobacterium.

pCGN149a was digested with BglII and SphI. This small BglII-SphI fragment of pCGN149a was replaced with the BamHI-SphI fragment from MI (see below) isolated by digestion with BamHI and SphI. This produces pCGN167, a construct containing a full length CaMV promoter, 1ATG-kanamycin gene, 3' end and the bacterial Tn903-type kanamycin gene. MI is an EcoRI fragment from pCGN546X (see construction of pCGN587) and was cloned into the EcoRI cloning site of M13mp9 in such a way that the PstI site in the 1ATG-kanamycin gene was proximal to the polylinker region of M13mp9.

The HindIII-BamHI fragment in the pCGN167 containing the CaMV-35S promoter, 1ATG-kanamycin gene and the BamHI-fragment 19 of pTiA6 was cloned into the BamHI-HindIII sites of pUC19 creating pCGN976. The 35S promoter and 3' region from transcript 7 was developed by inserting a 0.7 kb HindIII-EcoRI fragment of pCGN976 (35S promoter) and the 0.5 kb EcoRI-SalI fragment of pCGN709 (transcript 7:3') into the HindIII-SalI sites of pCGN566 creating pCGN766c.

The 0.7 kb HindIII-EcoRI fragment of pCGN766c (CaMV35S promoter) was ligated to the 1.5 kb EcoRI-SalI fragment in pCGN726c (1ATG-KAN 3' region) followed by insertion into the HindIII-SalI sites of pUC119 to produce pCGN778The. 2.2 kb region of pCGN778, HindIII-SalI fragment containing the CaMV-35S promoter and 1ATG-KAN- 3' region was used to replace the HindIII-SalI linker region of pCGN739 to produce pCGN783.

Transfer of the Binary Vector pCGN948 into Agrobacterium pCGN948 was introduced into *Agrobacterium tumefaciens* EHA101 (Hood et al., *J. Bacteriol.* (1986) 168:1291–1301) by transformation. An overnight 2 ml culture of EHA101 was grown in MG/L broth at 30° C. 0.5 ml was inoculated into 100 ml of MG/L broth (Garfinkel and Nester, *J. Bacteriol.* (1980) 144:732–743) and grown in a shaking incubator for 5 h at 30° C. The cells were pelleted by centrifugation at 7K, resuspended in 1 ml of MG/L broth and placed on ice. Approximately, 1 µg of pCGN948 DNA was placed in 100 µl of MG/L broth to which 200 µl of the EHA101 suspension was added; the tube containing the DNA-cell mix was immediately placed into a dry ice/ethanol bath for 5 minutes. The tube was quick thawed by 5 minutes in 37° C. water bath followed by 2 h of shaking at 30° C. after adding 1 ml of fresh MG/L medium. The cells were pelleted and spread onto MG/L plates (1.5% agar) containing 100 mg/l gentamicin. Plasmid DNA was isolated from individual gentamicin-resistant colonies, transformed back into *E. coli*, and characterized by restriction enzyme analysis to verify that the gentamicin-resistant EHA101 contained intact copies of pCGN948. Single colonies are picked and purified by two more streakings on MG/L plates containing 100 mg/l gentamicin.

Transformation and Regeneration of *B. Napus*

Seeds of *Brassica napus* cv Westar were soaked in 95% ethanol for 4 minutes. They were sterilized in 1% solution of sodium hypochlorite with 50 µl of "Tween 20" surfactant per 100 ml sterile solution. After soaking for 45 minutes, seeds were rinsed 4 times with sterile distilled water. They were planted in sterile plastic boxes 7 cm wide, 7 cm long, and 10 cm high (Magenta) containing 50 ml of 1/10th concentration of MS (Murashige minimal organics medium, Gibco) with added pyridoxine (50 µg/l), nicotinic acid (50 µg/l), glycine (200 µg/l) and solidified with 0.6% agar. The seeds germinated and were grown at 22° C. in a 16h-8h light-dark cycle with the light intensity approximately 65 µEm$^{-2}$s$^{-1}$. After 5 days the seedlings were taken under sterile conditions and the hypocotyls excised and cut into pieces of about 4 mm in length. The hypocotyl segments were placed on a feeder plate or without the feeder layer on top of a filter paper on the solidified B5 0/1/1 or B5 0/1/0 medium. B5 0/1/0 medium contains B5 salts and vitamins (Gamborg, Miller and Ojima, *Experimental Cell Res.* (1968) 50:151–158), 3% sucrose, 2,4-dichlorophenoxyacetic acid (1.0 mg/l), pH adjusted to 5.8, and the medium is solidified with 0.6% Phytagar; B5 0/1/1 is the same with the addition of 1.0 mg/l kinetin. Feeder plates were prepared 24 hours in advance by pipetting 1.0 ml of a stationary phase tobacco suspension culture (maintained as described in Fillatti et al., *Molecular General Genetics* (1987) 206:192–199) onto B5 0/1/0 or B5 0/1/1 medium. Hypocotyl segments were cut and placed on feeder plates 24 hours prior to Agrobacterium treatment.

*Agrobacterium tumefaciens* (strain EHA101x948) was prepared by incubating a single colony of Agrobacterium in MG/L broth at 30° C. Bacteria were harvested 16 hours later and dilutions of 10$^8$ bacteria per ml were prepared in MG/L broth. Hypocotyl segments were inoculated with bacteria by placing the segments in an Agrobacterium suspension and allowing them to set for 30–60 minutes, then removing and transferring to Petri plates containing B5 0/1/1 or 0/1/0 medium (0/1/1 intends 1 mg/l 2,4-D and 1 mg/l kinetin and 0/1/0 intends no kinetin). The plates were incubated in low light at 22° C. The co-incubation of bacteria with the hypocotyl segments took place for 24–48 hours. The hypocotyl segments were removed and placed on B5 0/1/1 or 0/1/0 containing 500 mg/l carbenicillin (kanamycin sulfate at 10, 25, or 50 mg/l was sometimes added at this time) for 7 days in continuous light (approximately 65 µEm$^{-2}$S$^{-1}$) at 22° C. The segments were transferred to B5 salts medium containing 1% sucrose, 3 mg/l benzylamino purine (BAP) and 1 mg/l zeatin. This was supplemented with 500 mg/l carbenicillin, 10, 25, or 50 mg/l kanamycin sulfate, and solidified with 0.6% Phytagar (Gibco). Thereafter, explants were transferred to fresh medium every two weeks.

After one month green shoots developed from green calli which were selected on media containing kanamycin. Shoots continued to develop for three months. The shoots were cut from the calli when they were at least 1 cm high and placed on B5 medium with 1% sucrose, no added growth substances, 300 mg/l carbenicillin, and solidified with 0.6% phytagar. The shoots continued to grow and several leaves were removed to test for neomycin phosphotransferase II (NPTII) activity. Shoots which were positive for NPTII activity were placed in Magenta boxes containing B5 0/1/1 medium with 1% sucrose, 2 mg/l indolebutyric acid, 200 mg/l carbenicillin, and solidified with 0.6% Phytagar. After a few weeks the shoots developed roots and were transferred to soil. The plant were grown in a growth chamber at 22° C. in a 16–8 hours light-dark cycle with light intensity 220 µEm$^{-2}$s$^{-1}$ and after several weeks were transferred to the greenhouse.

Southern Data

Regenerated *B. napus* plants from cocultivations of *Agrobacterium tumefaciens* EHA101 containing pCGN948 and *B. napus* hypocotyls were examined for proper integration and embryo-specific expression of the spinach leaf ACP gene. Southern analysis was performed using DNA isolated from leaves of regenerated plants by the method of Dellaporta et al. (*Plant Mol. Biol. Rep.* (1983) 1:19–21) and purified once by banding in CsCl. DNA (10 µg) was digested with the restriction enzyme EcoRI, electrophoresed on a 0.7% agarose gel and blotted to nitrocellulose (see Maniatis et al., (1982) supra.). Blots were probed with pCGN945 DNA containing 1.8 kb of the spinach ACP sequence or with the EcoRI-HindIII fragment isolated from pCGN936c (made by transferring the HindIII-EcoRI fragment of pCGN930 into pCGN566) containing the napin 5' sequences labeled with $^{32}$p-dCTP by nick translation (described by the manufacturer, BRL Nick Translation Reagent Kit, Bethesda Research Laboratories, Gaithersburg, Md.). Blots were prehybridized and hybridized in 50% formamide, 10× Denhardt's, 5×SSC, 0.1% SDS, 5 mM EDTA, 100 µg/ml calf thymus DNA and 10% dextran sulfate (hybridization only) at 42° C. (Reagents described in Maniatis et al., (1982) supra.) Washes were in 1×SSC, 0.1% SDS, 30 min and twice in 0.1×SSC, 0.1% SDS 15 min each at 55° C.

Autoradiograms showed two bands of approximately 3.3 and 3.2 kb hybridized in the EcoRI digests of DNA from four plants when probed with the ACP gene (pCGN945)

indicating proper integration of the spinach leaf ACP construct in the plant genome since 3.3 and 3.2 kb EcoRI fragments are present in the T-DNA region of pCGN948. The gene construct was present in single or multiple loci in the different plants as judged by the number of plant DNA-construct DNA border fragments detected when probed with the napin 5' sequences.

Northern Data

Expression of the integrated spinach leaf ACP gene from the napin promoter was detected by Northern analysis in seeds but not leaves of one of the transformed plants shown to contain the construct DNA. Developing seeds were collected from the transformed plant 21 days postanthesis. Embryos were dissected from the seeds and frozen in liquid nitrogen. Total RNA was isolated from the seed embryos and from leaves of the transformed plant by the method of Crouch et al., (1983) supra, electrophoresed on formaldehyde-containing 1.5% agarose gels as described (Shewmaker et al., *Virology* (1985) 140:281–288) and blotted to nitrocellulose (*Thomas, Proc. Natl. Acad. Sci. USA* (1980) 77:5201–5205). Blots were prehybridized, hybridized, and washed as described above. The probe was an isolated PstI-BamHI fragment from pCGN945 containing only spinach leaf ACP sequences labeled by nick translation.

An RNA band of ~0.8 kb was detected in embryos but not leaves of the transformed plant indicating seed-specific expression of the spinach leaf ACP gene.

Example 3

Construction of *B. campestris* Napin Promoter Cassette

A BglII partial genomic library of *B. campestris* DNA was made in the lambda vector Charon 35 using established protocols (Maniatis et al., (1982) supra). The titer of the amplified library was ~1.2×10$^9$ phage/ml. Four hundred thousand recombinant bacteriophage were plated at a density of 10$^5$ pre 9×9 in. NZY plate (NZYM as described in Maniatis et al., (1982) supra) in NZY+10 MM MgSO$_4$+ 0.9% agarose after adsorption to DH1 *E. coli* cells (Hanahan, *Mol. Biol.* (1983) 166:557) for 20 min at 37° C. Plates were incubated at 37° C. for ~13 hours, cooled at 4° C. for 2.5 hours and the phage were lifted onto Gene Screen Plus (New England Nuclear) by laying precut filters over the plates for approximately 1 min and peeling them off. The adsorbed phage DNA was immobilized by floating the filter on 1.5 M NaCl, 0.5 M NaOH for 1 min., neutralizing in 1.5 M NaCl, 0.5 M Tris-HCl, pH 8.0 for 2 min and 2×SSC for 3 min. Filters were air dried until just damp, prehybridized and hybridized at 42° C. as described for Southern analysis. Filters were probed for napin-containing clones using an XhoI-SalI fragment of the cDNA clone BE5 which was isolated from the *B. campestris* seed cDNA library described using the probe pN1 (Crouch et al., (1983) supra). Three plaques were hybridized strongly on duplicate filters and were plaque purified as described (Maniatis et al., (1982) supra).

One of the clones named lambda CGN1-2 was restriction mapped and the napin gene was localized to overlapping 2.7 kb XhoI and 2.1 kb SalI restriction fragments. The two fragments were subcloned from lambda CGN1-2 DNA into pCGN789 (a pUC based vector the same as pUC119 with the normal polylinker replaced by the synthetic linker - 5' GGAATTCGTCGACAGATCTCTGCAGCTC-GAGGGATCCAAGCTT 3' (which represents the polylinker EcoRI, SalI, BglII, PstI, XhoI, BamHI, HindIII). The identity of the subclones as napin was confirmed by sequencing. The entire coding region sequence as well as extensive 5' upstream and 3' downstream sequences were determined (FIG. 2). The lambda CGN1-2 napin gene is that encoding the mRNA corresponding to the BE5 cDNA as determined by the exact match of their nucleotide sequence.

An expression cassette was constructed from the 5'-end and the 3'-end of the lambda CGN1-2 napin gene as follows in an analogous manner to the construction of pCGN944. The majority of the napin coding region of pCGN940 was deleted by digestion with SalI and religation to form pCGN1800. Single-stranded DNA from pCGN1800 was used in an in vitro mutagenesis reaction (Adelman et al., *DNA* (1983) 2:183–193) using the synthetic oligonucleotide 5' GCTTGTTCGCCATGGATATCTTCTGTATGTTC 3'. This oligonucleotide inserted an EcoRV and an NcoI restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with the synthetic linker described above in place of the normal polylinker) cut with EcoRI and blunted by filling in with DNA Polymerase I Klenow fragment to create pCGN1802. 3' sequences from the lambda CGN1-2 napin gene were added to XhoI-HindIII digested pCGN1802 from pCGN941 digested with XhoI and HindIII. The resulting clone, pCGN1803, contains approximately 1.6 kb of napin 3'-sequences as well as promoter sequences, but a 326 nucleotide HindIII fragment normally found at the 3'-end of lambda CGN1-2 is inserted opposite to its natural orientation. As a result, there are two HindIII sites in pCGN1803. This reversed fragment was removed by digestion of pCGN1803 with HindIII. Following religation, a clone was selected which now contained only approximately 1.25 kb of the original 1.6 napin 3'-sequence. This clone, pCGN1808, is the lambda CGN1-2 expression cassette and contains 1.725 kb of napin promoter sequence, and 1.265 kb of napin 3' sequences with the unique cloning sites SalI, BglI, PstI, and XhoI in between. Any sequence that requires seed-specific transcription or expression in Brassica, for example, a fatty acid gene, can be inserted in this cassette in a manner analogous to that described for spinach leaf ACP and the B. napus napin cassette (see Example 2).

pCGN3223 Napin Expression Cassette pCGN1808 is modified to contain flanking restriction sites to allow movement of only the expression sequences and not the antibiotic resistance marker to binary vectors such as pCGN1557 (McBride and Summerfelt (1990) *J. Mol. Biol.* 14:269–276). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and RpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using in a Perkin Elmer/Cetus thermocycler according to manufacturer's specifications. The PCR fragment is subcloned as a blunt-ended fragment into pUC8 (Vieira and Messing (1982) *Gene* 19:259–268) digested with HindII to give pCGN3217. Sequence of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and RpnI restriction sites and unique SalI, BglIII, PstI, and XhoI cloning sites are located between the 5' and 3' noncoding regions.

Example 4
Isolation of Other Seed Specific Promoters

Other seed-specific promoters may be isolated from genes encoding proteins involved in seed triacylglycerol synthesis, such as acyl carrier protein from Brassica seeds. Immature seeds were collected from Brassica campestris cv. "R-500," a self-compatible variety of turnip rape. Whole seeds were collected at stages corresponding approximately to 14 to 28 days after flowering. RNA isolation and preparation of a cDNA bank was as described above for the isolation of a spinach ACP cDNA clone except the vector used was pCGN565. To probe the cDNA bank, the oligonucleotide (5')-ACTTTCTCAACTGTCTCTGGTTTAGCAGC- (3') was synthesized using an Applied Biosystems DNA Synthesizer, model 380A, according to manufacturer's recommendations. This synthetic DNA molecule will hybridize at low stringencies to DNA or RNA sequences coding for the amino acid sequence (ala-ala-lys-pro-glu-thr-val-glulys-val). This amino acid sequence has been reported for ACP isolated from seeds of *Brassica napus* (Slabas et al., 7th International Symposium of the Structure and Function of Plant Lipids, University of California, Davis, Calif., 1986); ACP from *B. campestris* seed is highly homologous. Approximately 2200 different cDNA clones were analyzed using a colony hybridization technique (Taub and Thompson, *Anal. Biochem.* (1982) 126:222–230) and hybridization conditions corresponding to Wood et al. (*Proc. Natl. Acad. Sci.* (1985) 82:1585–1588). DNA sequence analysis of two cDNA clones showing obvious hybridization to the oligonucleotide probe indicated that one, designated pCGN1Bcs, indeed coded for an ACP-precursor protein by the considerable homology of the encoded amino acid sequence with ACP proteins described from *Brassica napus* (Slabas et al., 1980 supra). Similarly to Example 3, the ACP cDNA clone, pCGN1BCS, was used to isolate ACP genomic clones containing the regulatory information for expression of ACP during triacylglyceride synthesis in the seeds. DNA was isolated from *B. campestris* cv. R500 young leaves by the procedure of Scofield and Crouch (*J. Biol. Chem.* (1987) 262:12202–12208). A Sau3A partial genomic library of the *B. campestris* DNA was made in the lambda vector Embl 3 (Stratagene, San Diego, Calif.) using established protocols (Maniatis et al., (1982) supra) and manufacturer's instructions. The titer of the library was ~1.0×10⁸ phage/ml. Six hundred thousand recombinant bacteriophage were plated and screened as described in Example 3 with the exception that the *E. coli* host cells used were strain P2392 (Stratagene, San Diego, Calif.). Filters were prehybridized and hybridized at 42° C. in 25 ml each of hybridization buffer containing 50% formamide, 10× Denhardt's, 5× SSC, 5 Mm EDTA, 0.1% SDS, and 100 μg/ml denatured salmon sperm DNA (reagents described in Maniatis et al., (1982) supra). The probe used in these hybridizations was 0.2 μg of a nick-translated 530 base pair BglII-DraI fragment of pCGN1Bcs, the *B. campestris* ACP cDNA clone described above. Six plaques were hybridized strongly on duplicate filters after washing the filters at 55° C. in 0.1× SSC/0.2% SDS, and were plaque-purified as described (Maniatis et al., (1982) supra).

Figure 1B:
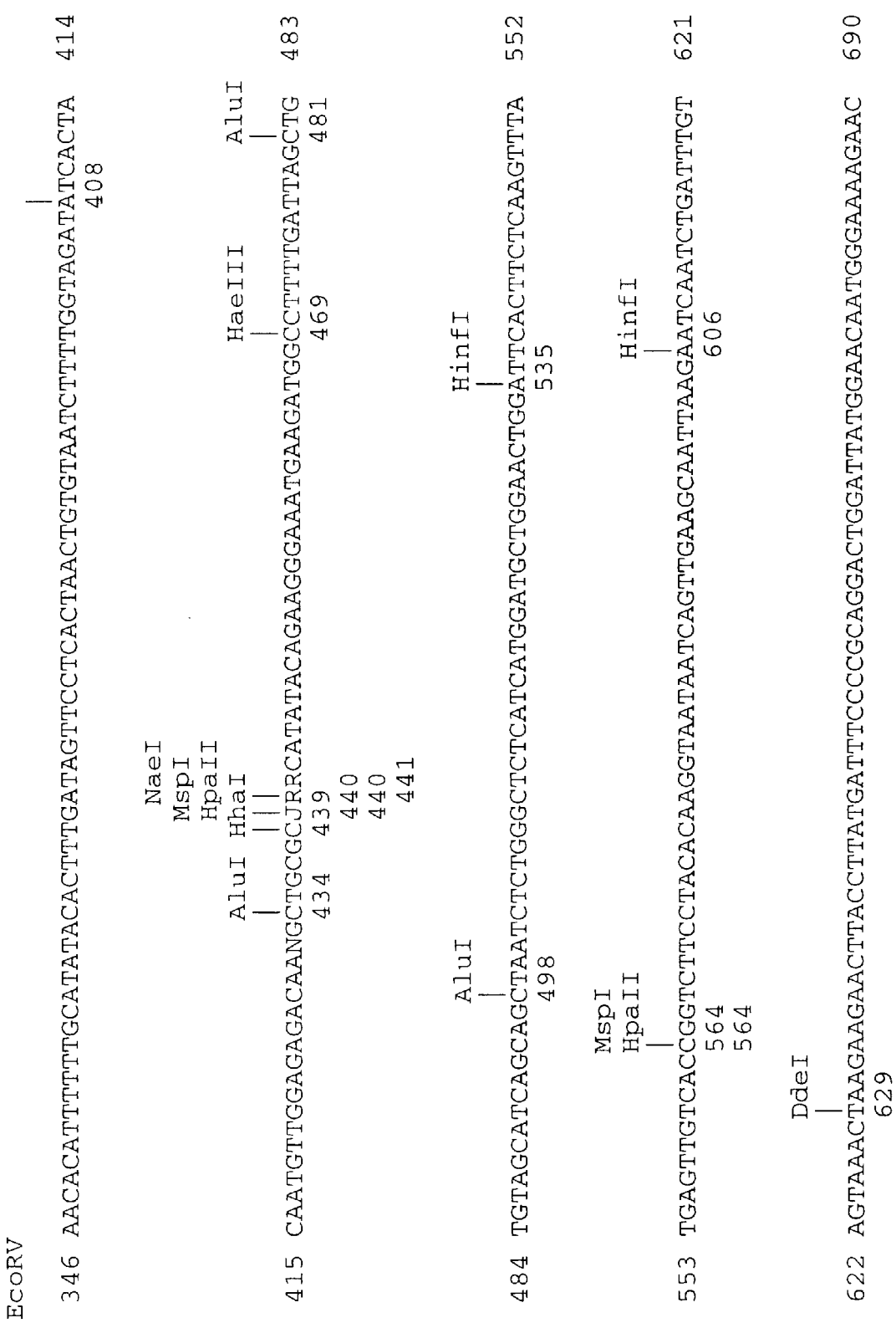
Figure 1D:
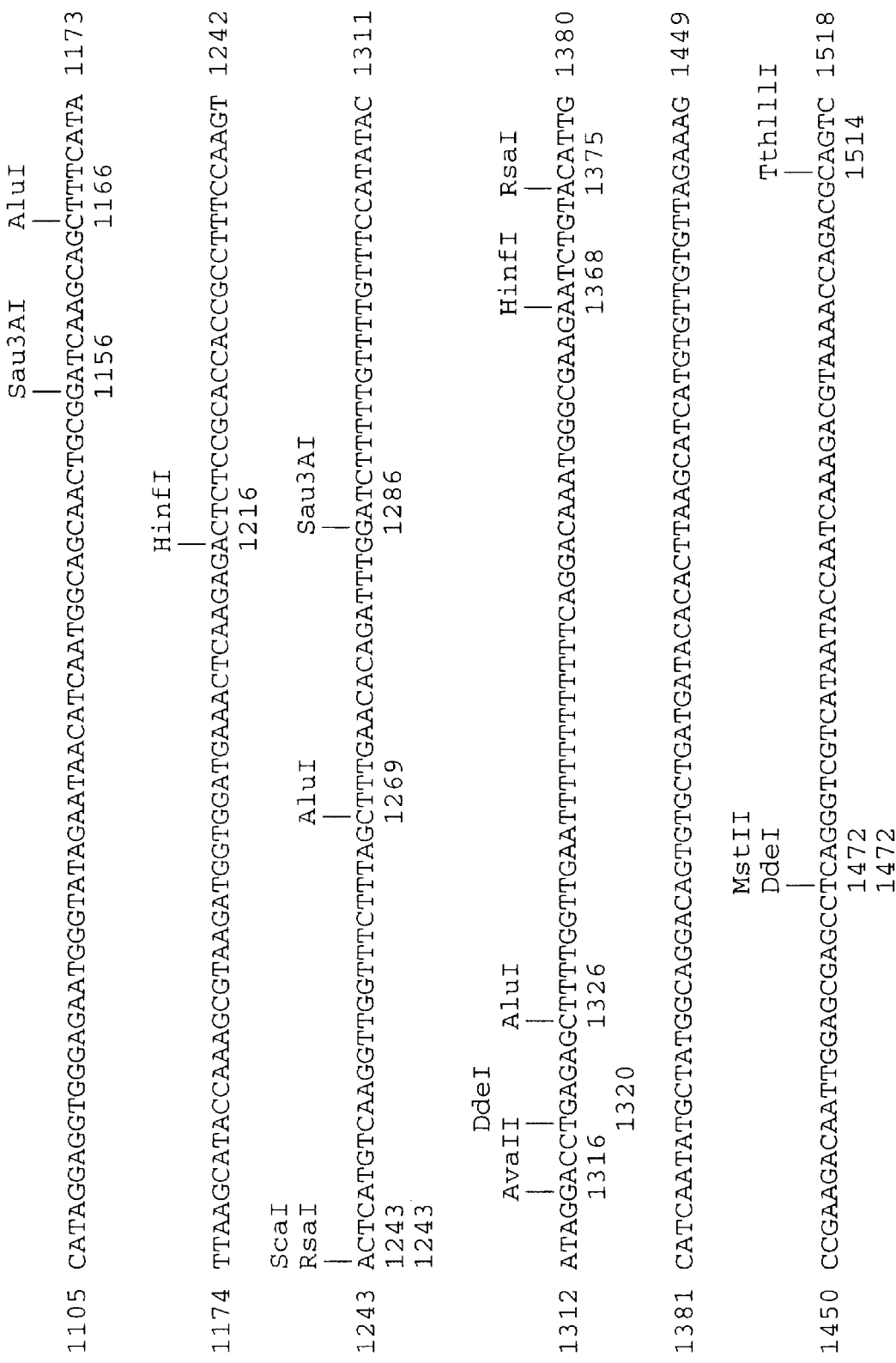
Figure 1E:
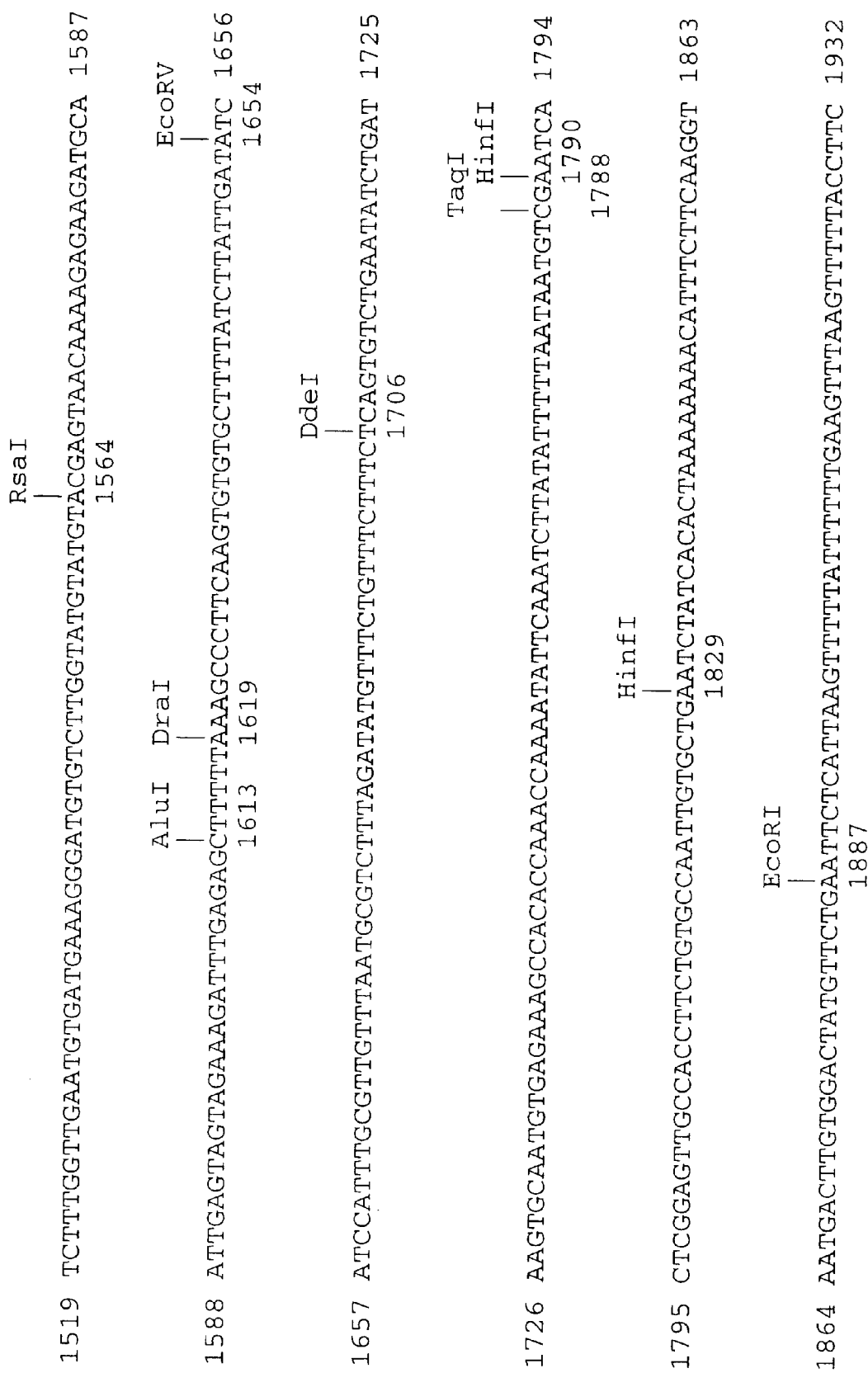
Figure 1F:
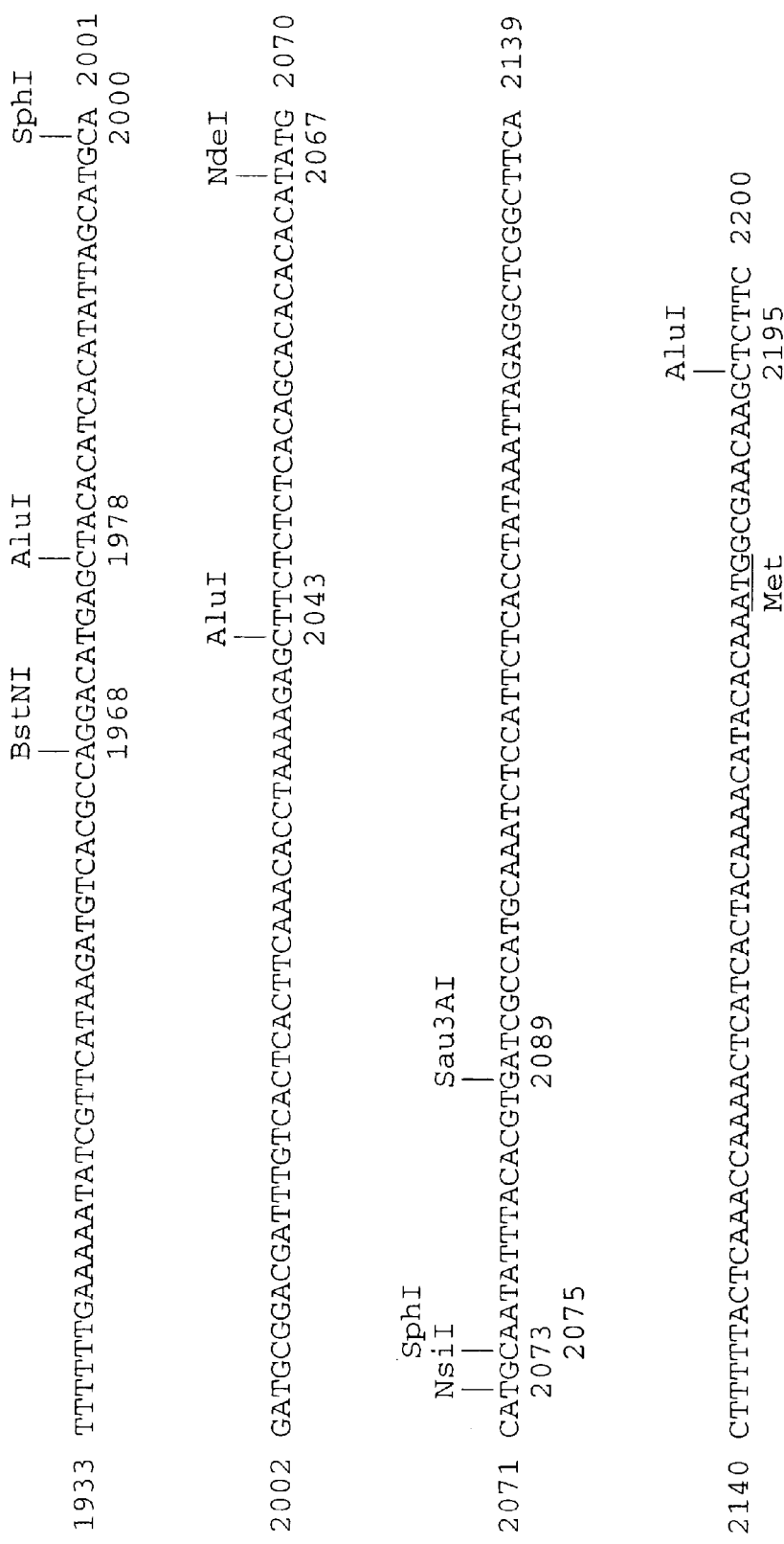
Figure 2B:
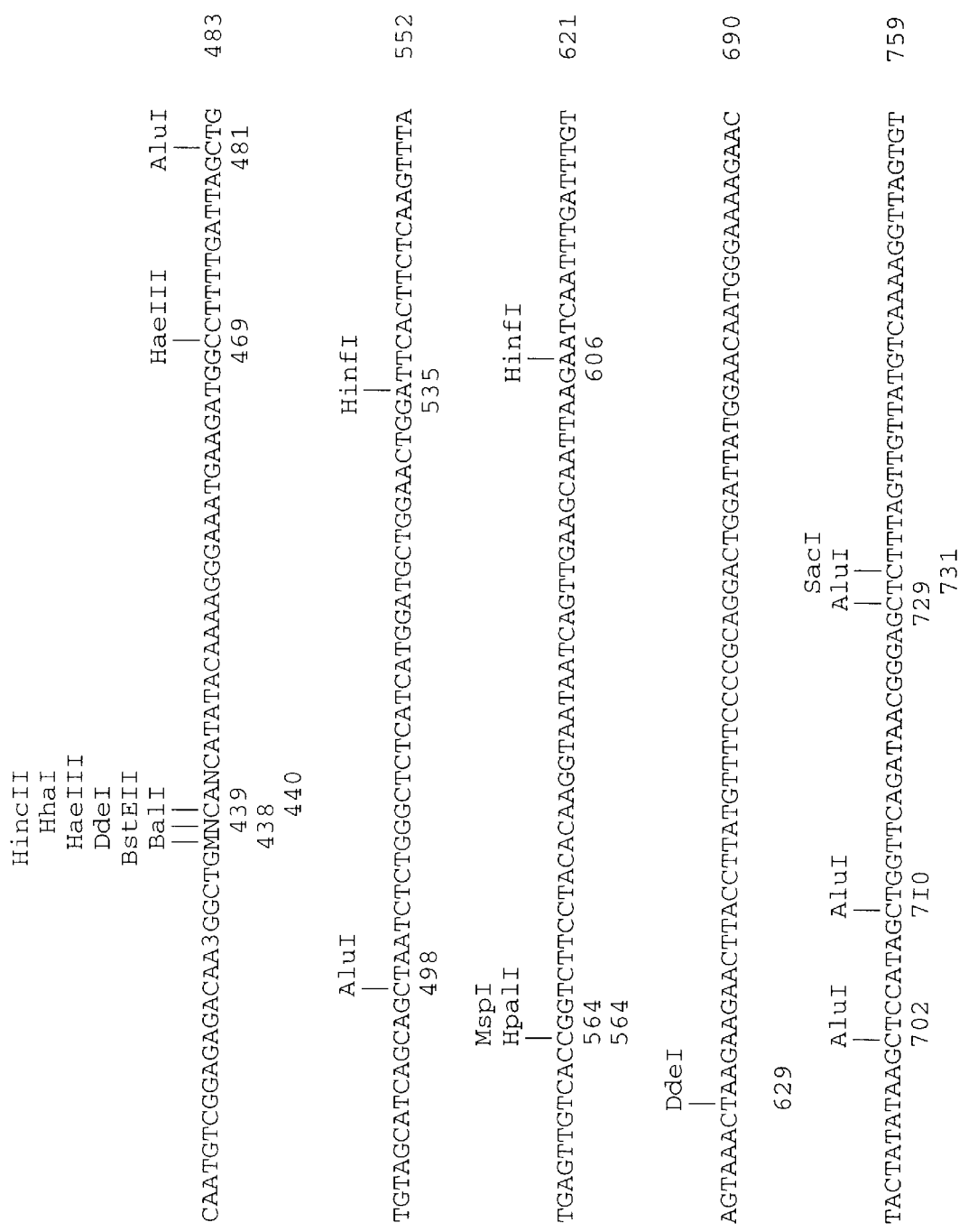
Figure 2C:
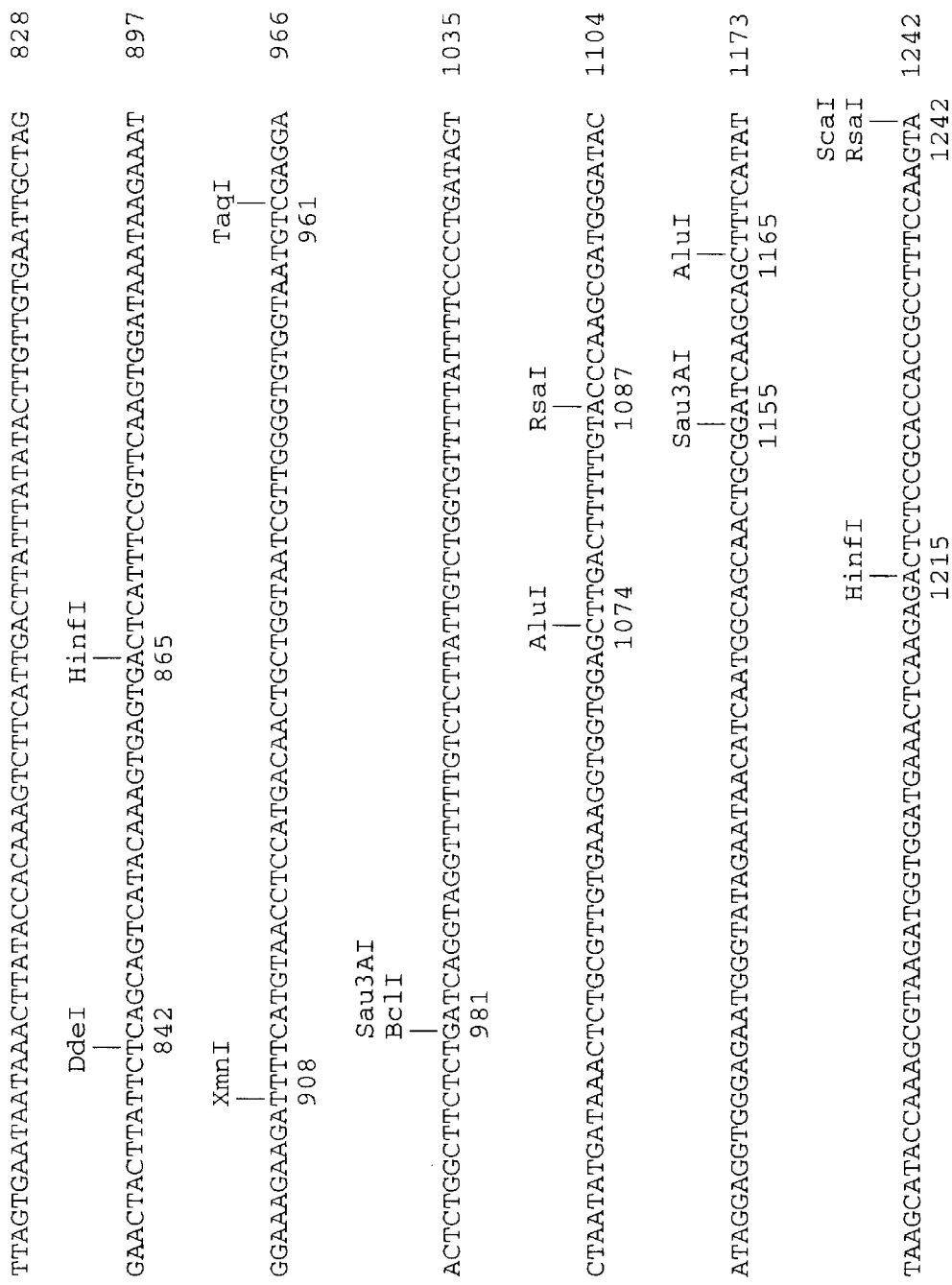
Figure 2E:
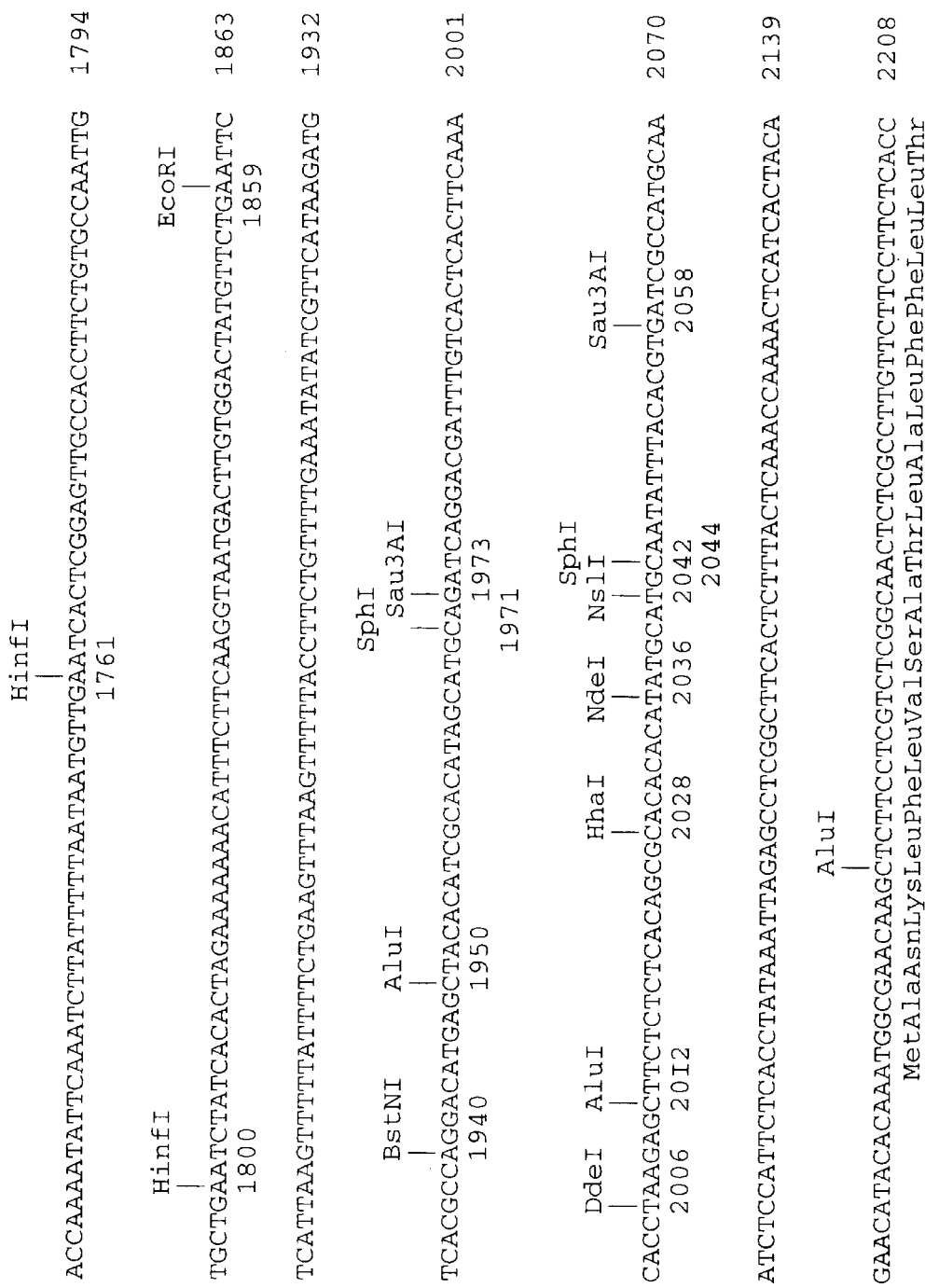
Figure 2F:
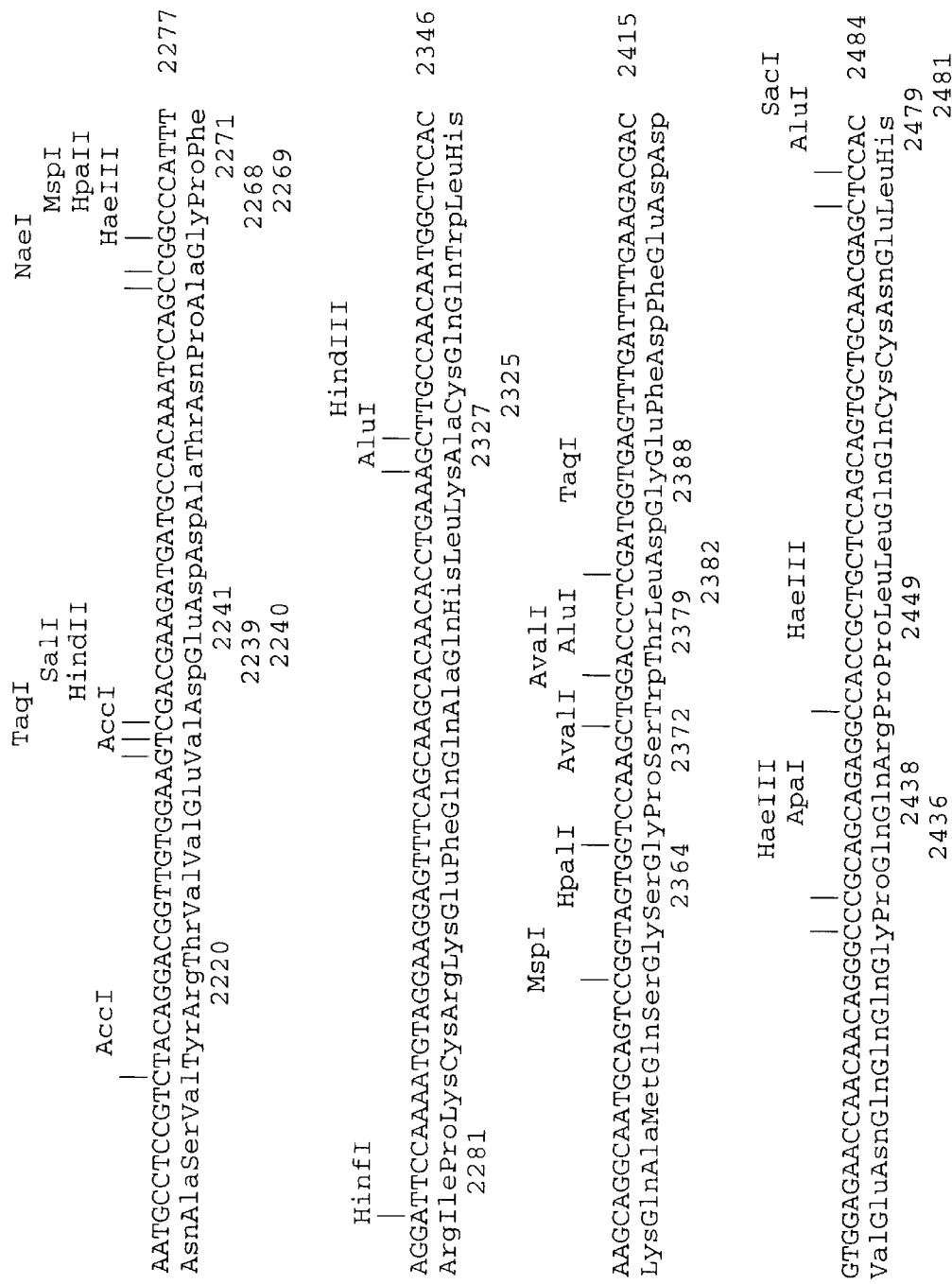
Figure 2G:
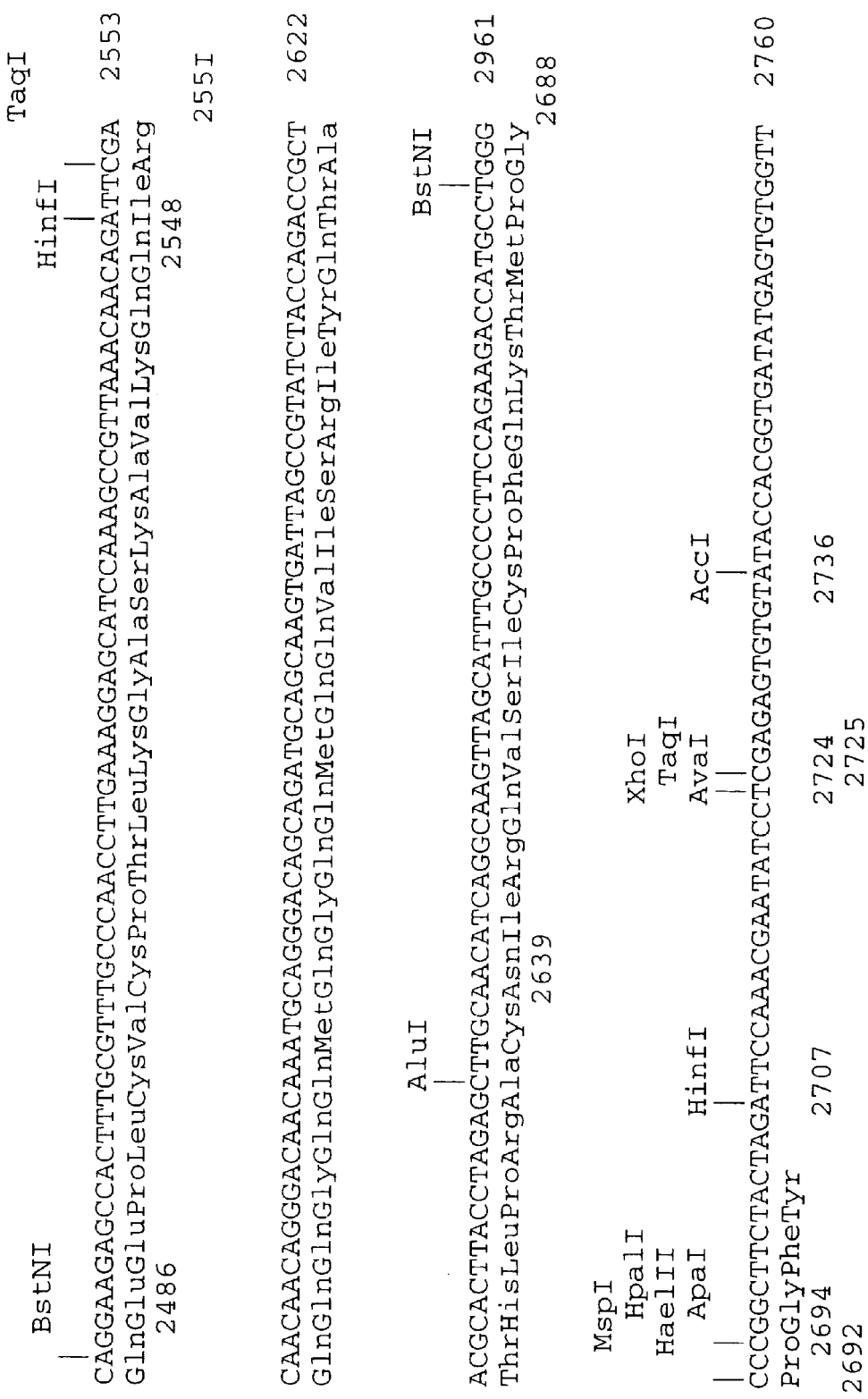
Figure 2H:
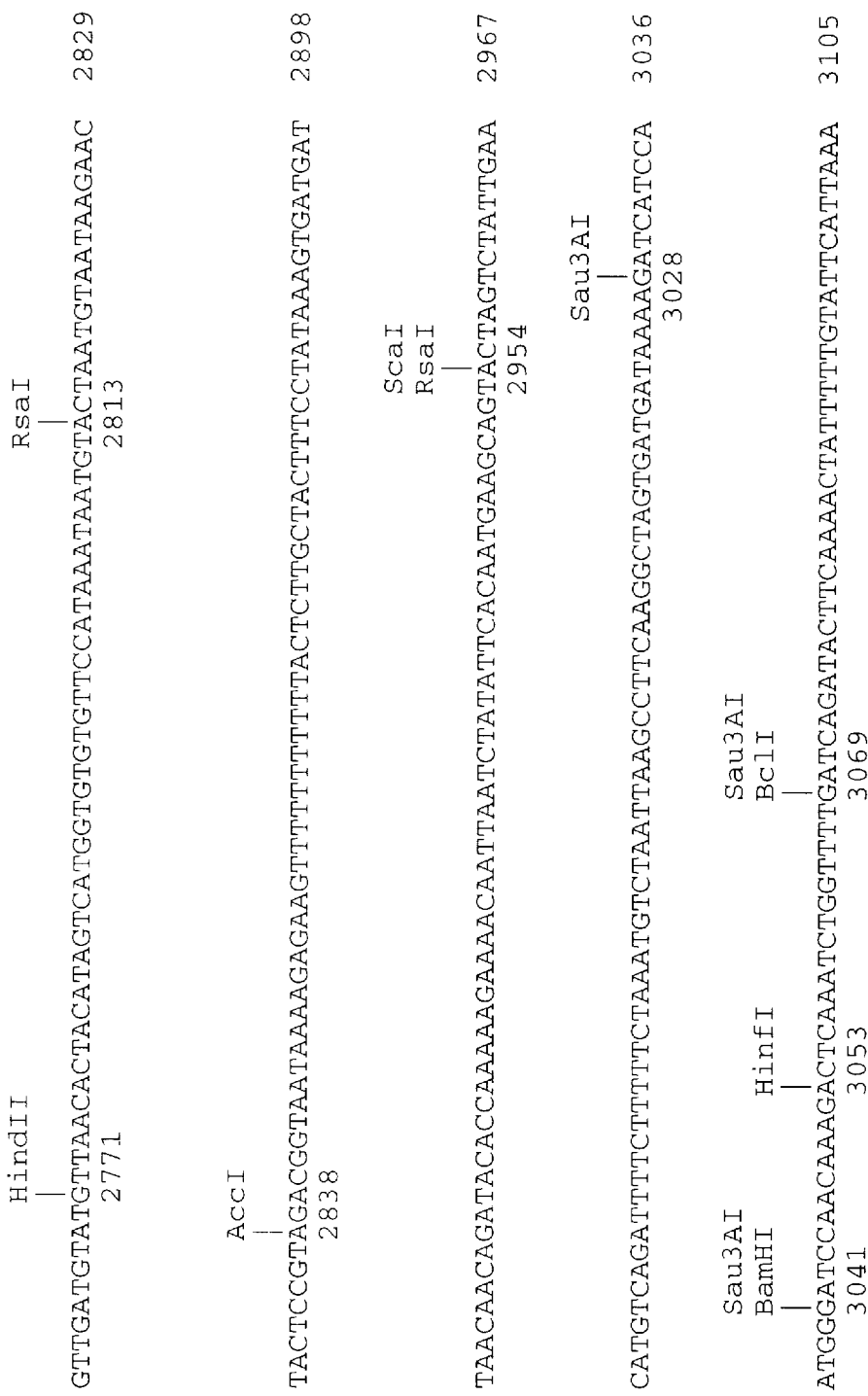
Figure 2I:
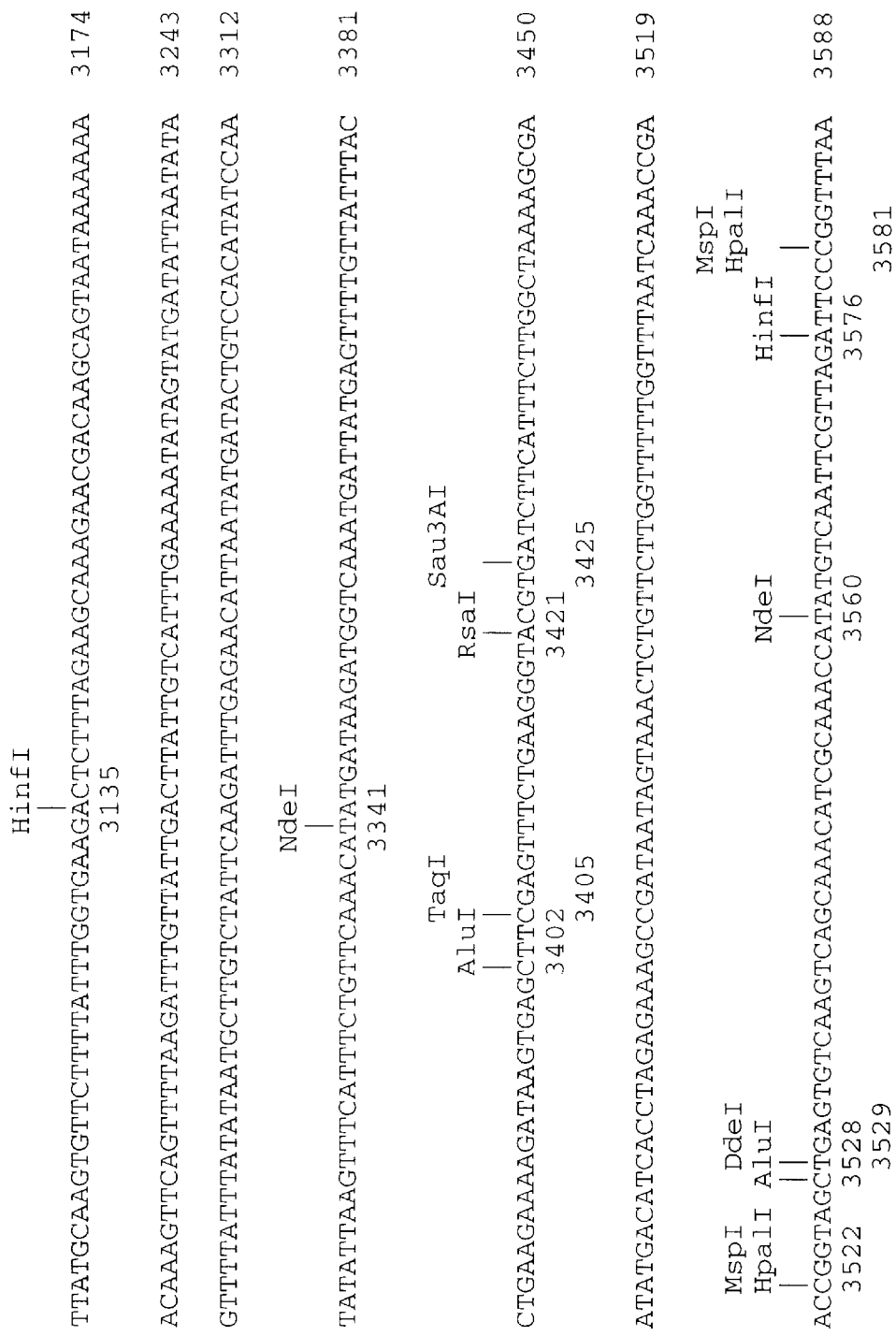
Figure 2J:
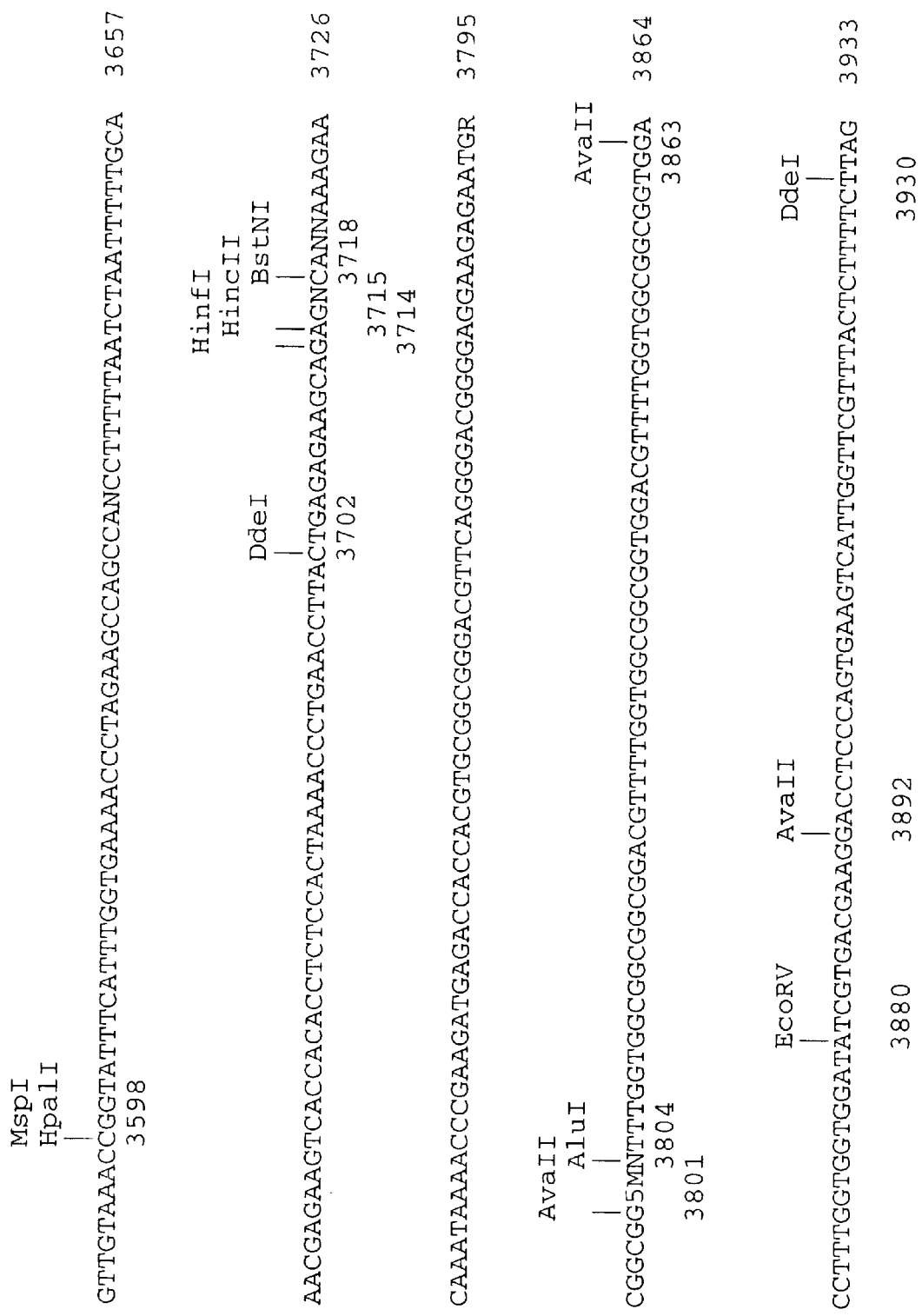
Figure 2K:
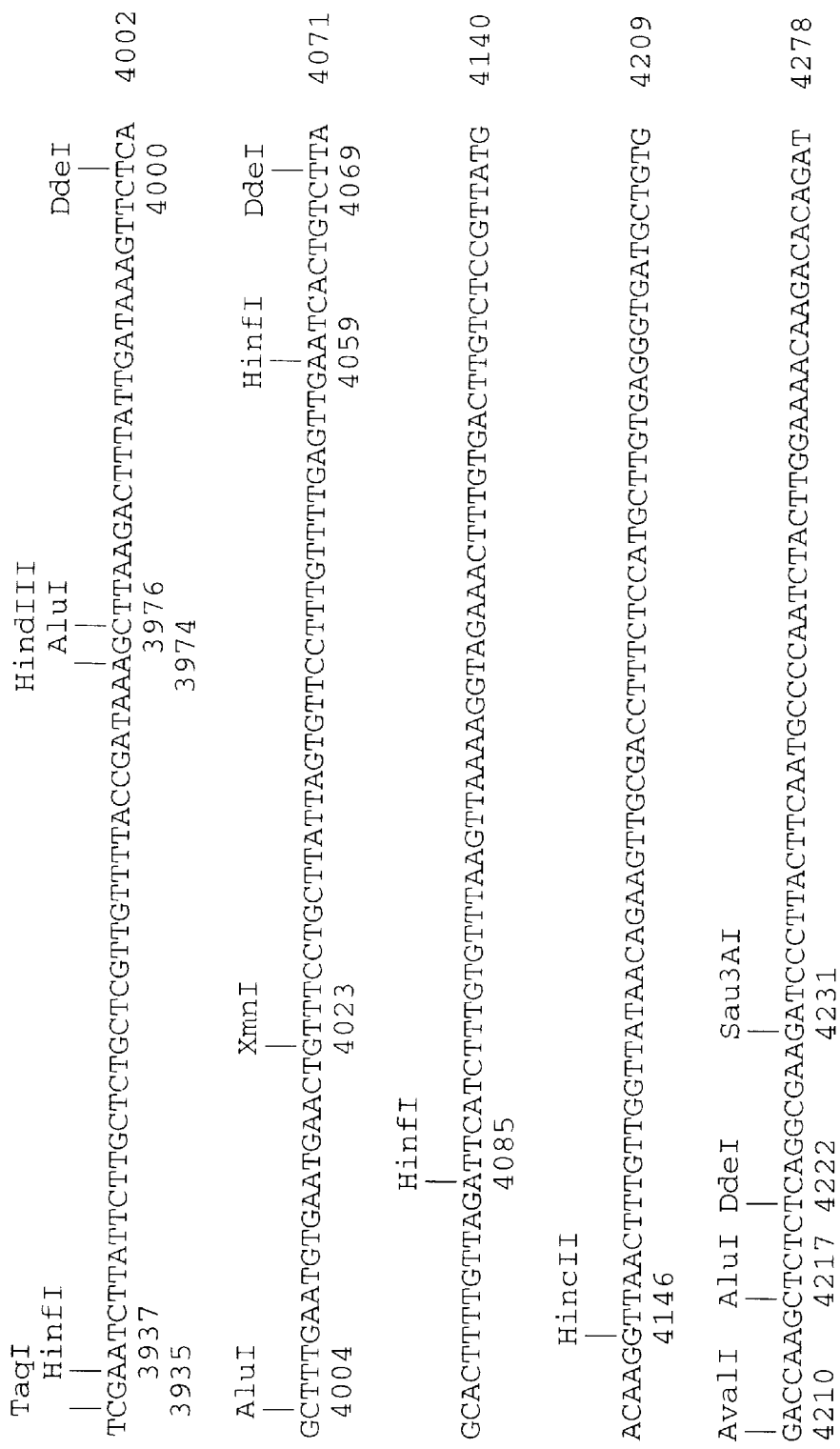
Figure 2L:
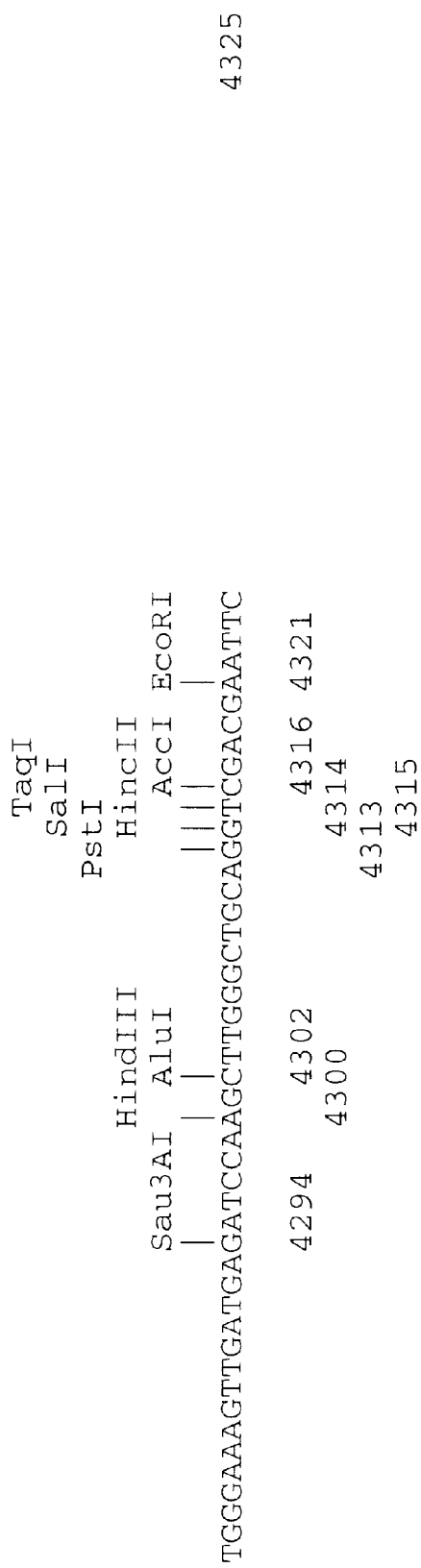
Figure 3C:
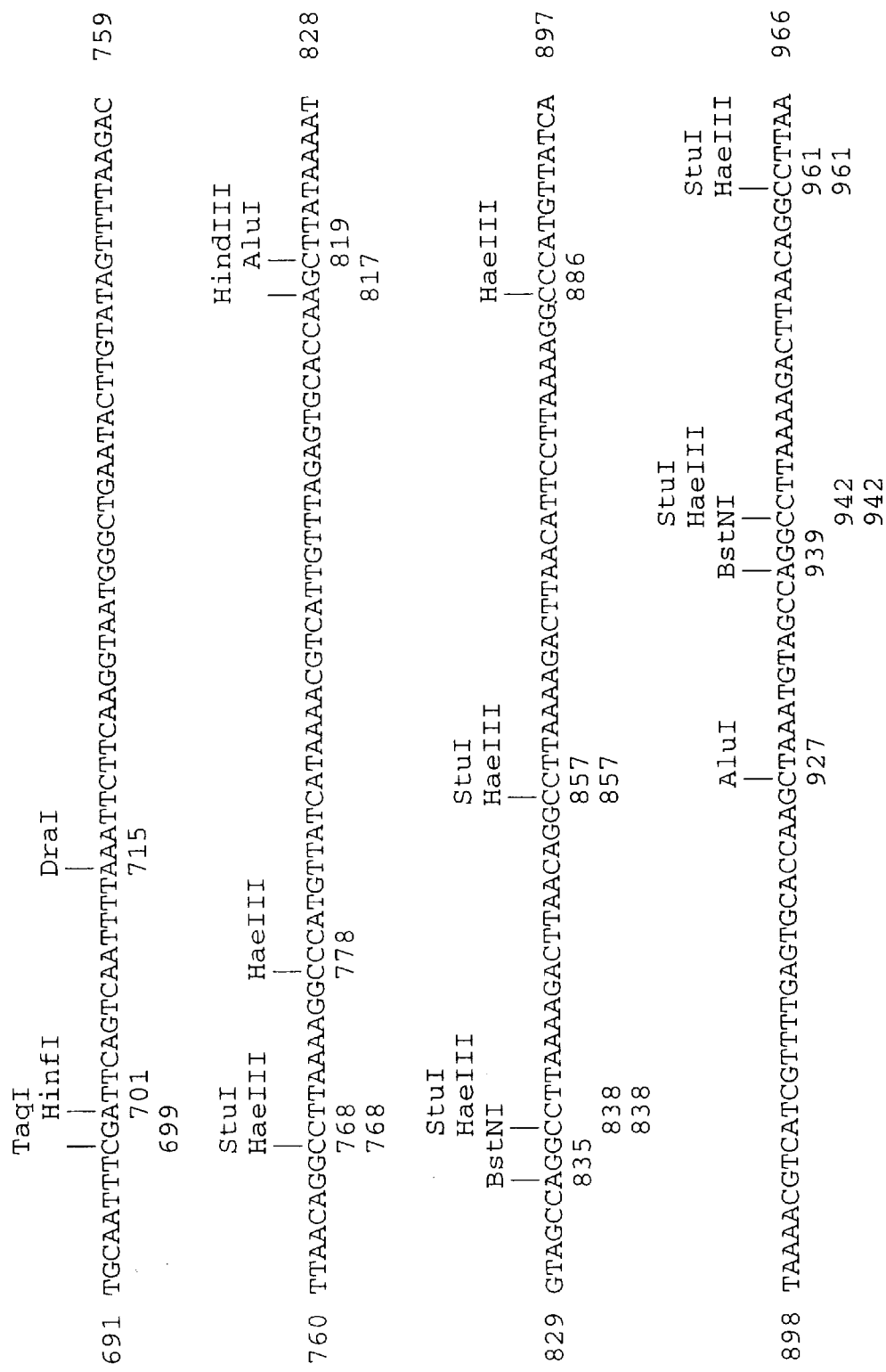
Figure 3E:
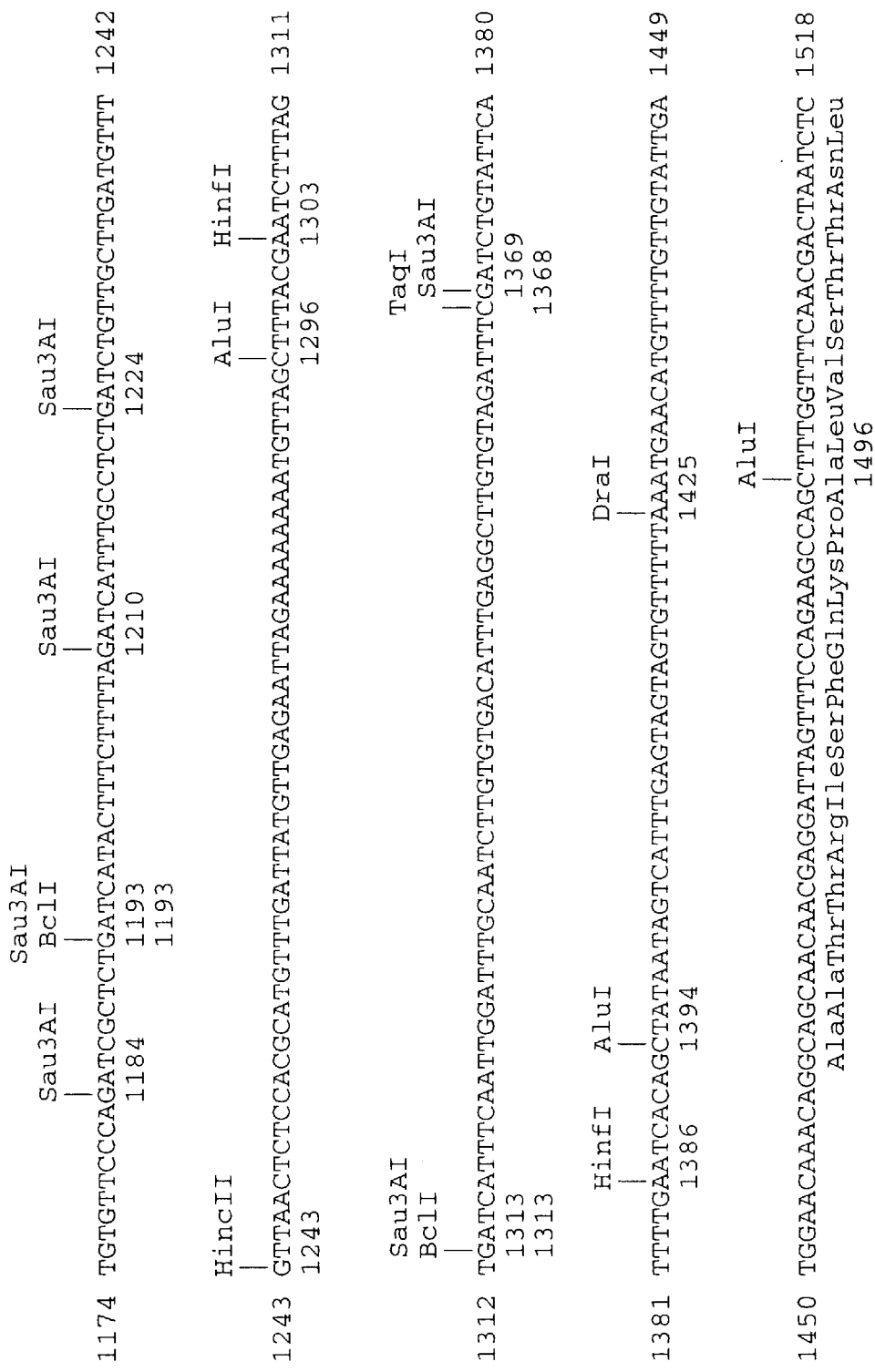
Figure 3G:
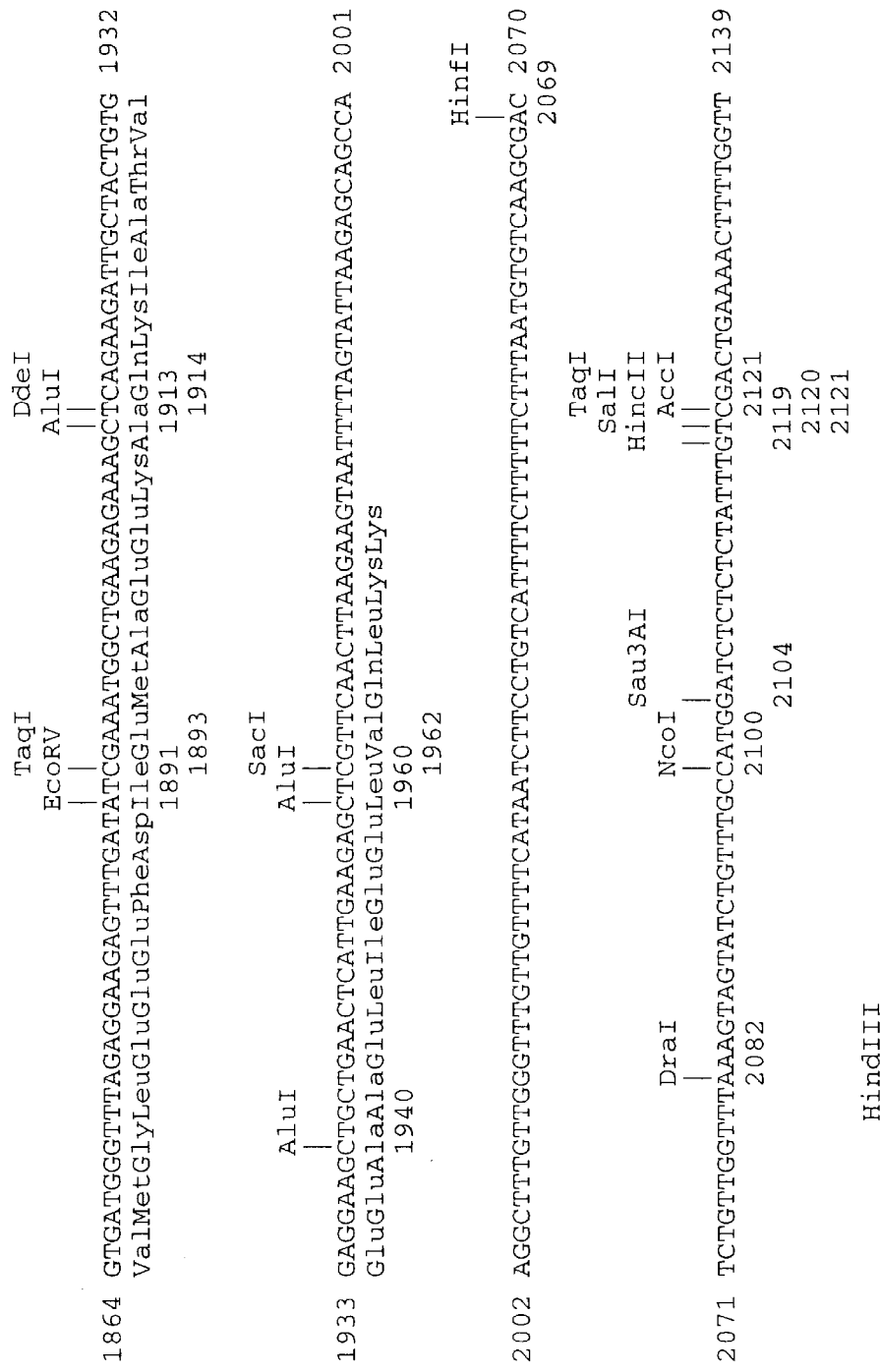

Restriction analysis followed by Southern hybridization was performed on some of the clones using the hybridization conditions and radiolabeled probe described above. One clone, Bcg4-4, contains the ACP gene on two overlapping restriction fragments, an ~5.1 kb SstI fragment and an ~1.2 kb HindIII fragment. These restriction fragments were subcloned into the cloning vector pCGN565. The DNA sequence of some regions of the subclones verified by homology that Bcg4-4 is an ACP gene. The sequence also shows that this particular ACP gene is expressed in plants, as the sequence in the coding region matches exactly the sequence of the PCGNLBcs ACP cDNA except for three regions. These regions are believed to be intervening sequences, a common element of eukaryotic genes that is spliced out during processing of mRNA (Padgett et al., *Ann. Rev. Biochem.* (1986) 55:1119–1150). Further restriction mapping of the SstI subclone identified an XhoI fragment containing ~1.5 kb of 5' sequence upstream from the XhoI site near the 5' end of the PCGNLBCS cDNA clone. This XhoI fragment was subcloned in opposite orientations in the cloning/sequencing vector Bluescript+(Stratagene, San Diego, Calif.) and the clones were designated pCGN1941 and pCGN1941'. DNA sequencing of 1 kb of the DNA upstream of the coding region was completed. Also, the complete sequence of the 1.2 kb HindIII subclone described above was determined. The DNA sequence derived from the clones described above is shown in FIG. 3. Additional sequences at the 3' end of the ACP gene were subcloned on an ~1.6 kb SstI-BglII fragment into Bluescript+and Bluescript–(clones are designated pCGN1940 and pCGN19401'). The SstI site in these clones is the one found at the 3' end of the ACP coding region of PCGN1Bcs.

An expression cassette can be constructed from the 5' upstream sequences and 3' downstream sequences of Bcg4-4 as follows. The PCGN1941 XhoI subclone is used for the 5' regulatory region. This clone contains the XhoI insert in the opposite orientation of the lacZ gene. The 3' regulatory region is altered to allow cloning as a PstI-BglII fragment into PCGN565 by oligonucleotide site-directed mutagenesis. Single-stranded DNA is made from pCGN1940 and altered by mutagenesis as described (Adelman et al., supra) with the synthetic oligonucleotide 5' CTTAAGAAGTAAC-CCGGGCTGCAGTTTTAGTATTAAGAG 3'. This oligonucleotide provides SmaI and PstI restriction sites just after the TAA stop codon of the pCGN1Bcs cDNA. The PstI-BglII 3' fragment is then cloned into the PstI and BamHI sites (the BamHI restriction site is destroyed in this process) of PCGN565. The resulting clone is digested with PstI and SmaI, and the fragment inserted into the corresponding sites in PCGN1941 (described above) in the same orientation as the 5' region. The resulting clone comprises the ACP expression cassette with PstI, EcoRI, and EcoRV sites available between the 5' and 3' regulatory regions for the cloning of genes to be expressed under the regulation of these ACP gene regions.

Example 5
Isolation of Seed-specific cDNA Clone, EA9

Ninety-six clones from the 14–28 day postanthesis *B. campestris* seed cDNA library (described in the previous example) were screened by dot blot hybridization of miniprep DNA on Gene Screen Plus nylon filters (NEN Research Products, Boston, Ma.). The probes used were radioactively labeled first-strand synthesis cDNAs made from the day 14–28 postanthesis seed nRNA or from *B. campestris* leaf MRNA. Clones which hybridized strongly to seed cDNA and little or not at all to leaf cDNA were catalogued. A number of clones were identified as representing the seed storage protein napin by cross-hybridization with an XhoI-SalI fragment of pNI (Crouch et al., (1983) supra), a *B. napus* napin cDNA. One of these napin clones, BE5, was used in Example 3 to identify a *B. campestris* genomic clone as a source of an embryo-specific promoter.

Another abundant class of cDNA clones were those represented by a clone designated EA9. EA9 cross-hybridized to seven other cDNA clones of 600 cDNAs screened by dot blot hybridization and was highly expressed in seeds and not in leaves. Northern blot analysis of mRNA isolated from day 14 postanthesis whole seed, and day 21 and 28 postanthesis embryos using a 700 bp EcoRI fragment of EA9 (see below) as a probe shows that EA9 is highly expressed at day 14 and expressed at a much lower level at day 21 and day 28 postanthesis. Because the embryo is so small at day 14, it was suspected that the predominant expression of EA9 might be in a tissue other than the embryo. Total RNA was isolated (Crouch et al., (1983) supra) from whole seed (14, 15, 17 and 19 days postanthesis), seed coats (day 14 and day 21 postanthesis) and embryos (day 21 postanthesis). Twenty-five μg of each sample were analyzed by Northern blot analysis as described in Example 2. The probe used was a 0.7 kb EcoRI DNA fragment isolated from the EA9 cDNA and labeled by nick-translation. The results of the Northern analysis showed the EA9 RNA was detected in whole seed at all times tested and in seed coats, but not in the embryo. A separate Northern analysis of whole seed RNA from days 13 through day 31 postanthesis (in two day intervals) indicated that EA9 was highly expressed between days 13 to 21 but was barely detectable by day 27 postanthesis.

In Situ Hybridization

Seed-coat specific expression of EA9 was confirmed by in situ hybridization analysis. Day 14 and 21 postanthesis whole seeds of *B. campestris* were fixed in a 4% paraformaldehyde phosphate buffered saline (PBS) solution. The tissue was then dehydrated through a graded tertiary-butyl alcohol (TBA) series, infiltrated with paraplast and cast into paraffin blocks for sectioning (Berlyn and Miksche, *Botanical Microtechnique and Cytochemistry* (1976), Iowa State University Press). Five μm longitudinal sections of the embedded seeds (one cell-layer thickness) were generated on a Reichert Histostat rotary microtome. The paraffin ribbons containing the seed sections were then affixed to gelatin-chrome alum subbed slides (Berlyn Miksche, (1976) supra).

Single-stranded radiolabeled RNA probes were made using the Riboprobe reaction system (Promega, Madison, Wis.). This system utilizes a vector which is derived from pUC12 and contains a bacteriophage SP6 promoter which lies immediately upstream from an M13 polylinker. First, the 700 bp EcoRI fragment was isolated from EA9 and subcloned into the polylinker region of the riboprobe vector in both orientations (sense and anti-sense). To generate a template for the transcription run-off transcription reactions, the recombinant plasmids were propagated, purified, and linearized with HindIII. The templates were then incubated in a reaction mixture containing the SP6 RNA polymerase, triphosphates and $^{35}$S-UTP (as described by the manufacturer). After adding RQ DNase (Promega), the labeled RNAs were run over Boehringer pre-packed Sephadex spin columns to remove unincorporated triphosphates.

The slides containing the sectioned seeds were hybridized with the radiolabeled sense and anti-sense RNA transcripts of EA9 according to the methods of Singer et al. (*Biotechniques* (1986) 4:230–241) and Taylor and Martineau (*Plant. Physiol.* (1986) 82:613–618). The hybridized slides were then treated with nuclear track emulsion NTB-3, (Eastman Kodak Company, Kodak Materials for Light Microscope Autoradiography, 1986) sealed in a light-tight box and exposed for 4 weeks at 5–10° C. After bringing the slides to room temperature they were developed in D-19 developer (Eastman Kodak Company), rinsed, fixed and dehydrated through a graded alcohol series. Cover slips were mounted with cytoseal (VWR Scientific).

Hybridization of the radiolabeled anti-sense EA9 riboprobe was seen only in the seed coat tissue of both day 14 and 21 seeds. No hybridization of the radiolabeled sense EA9 riboprobe was seen in any seed tissues.

DNA Sequence and Gene Copy Number

Figure 4B:
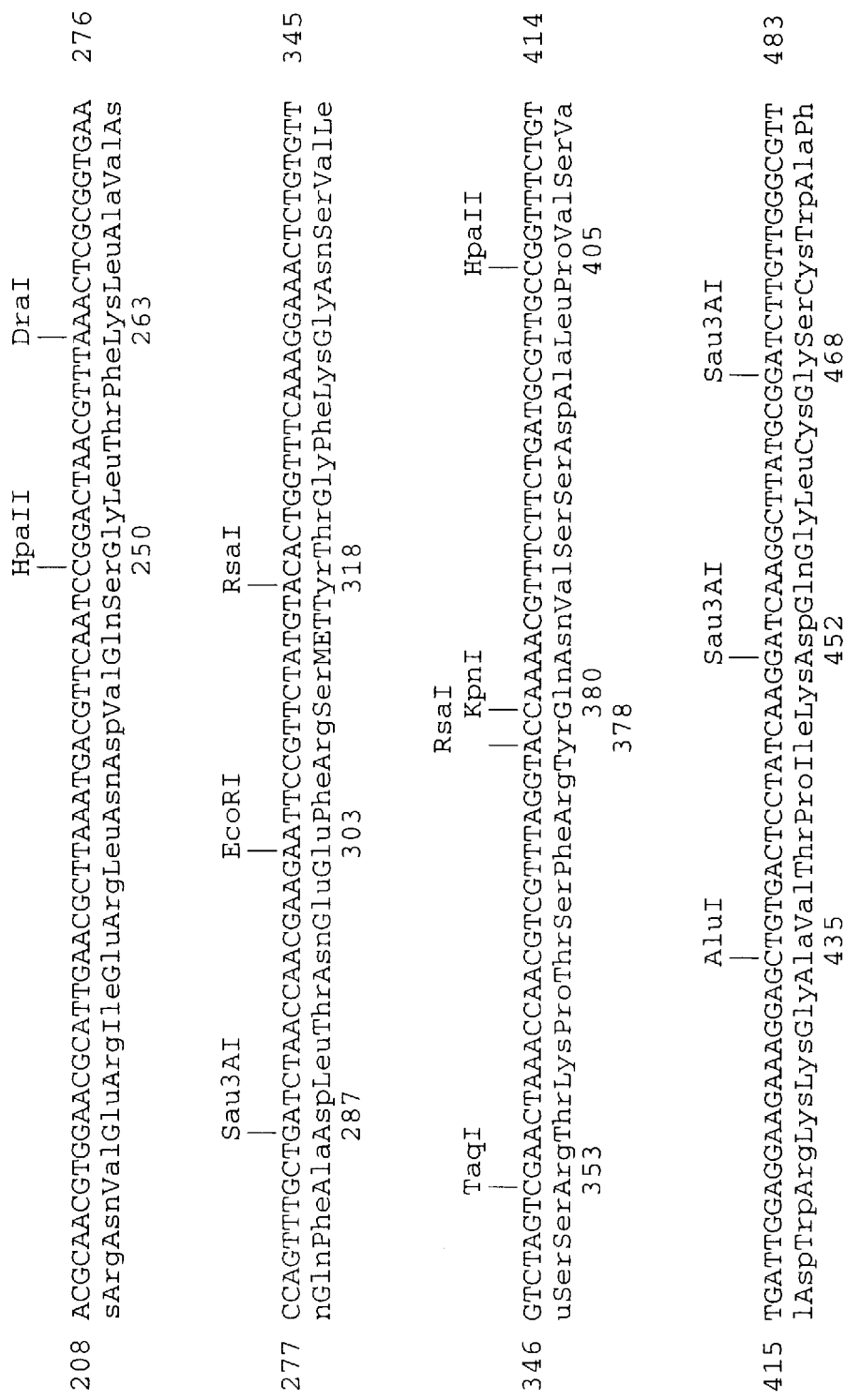
Figure 4D:
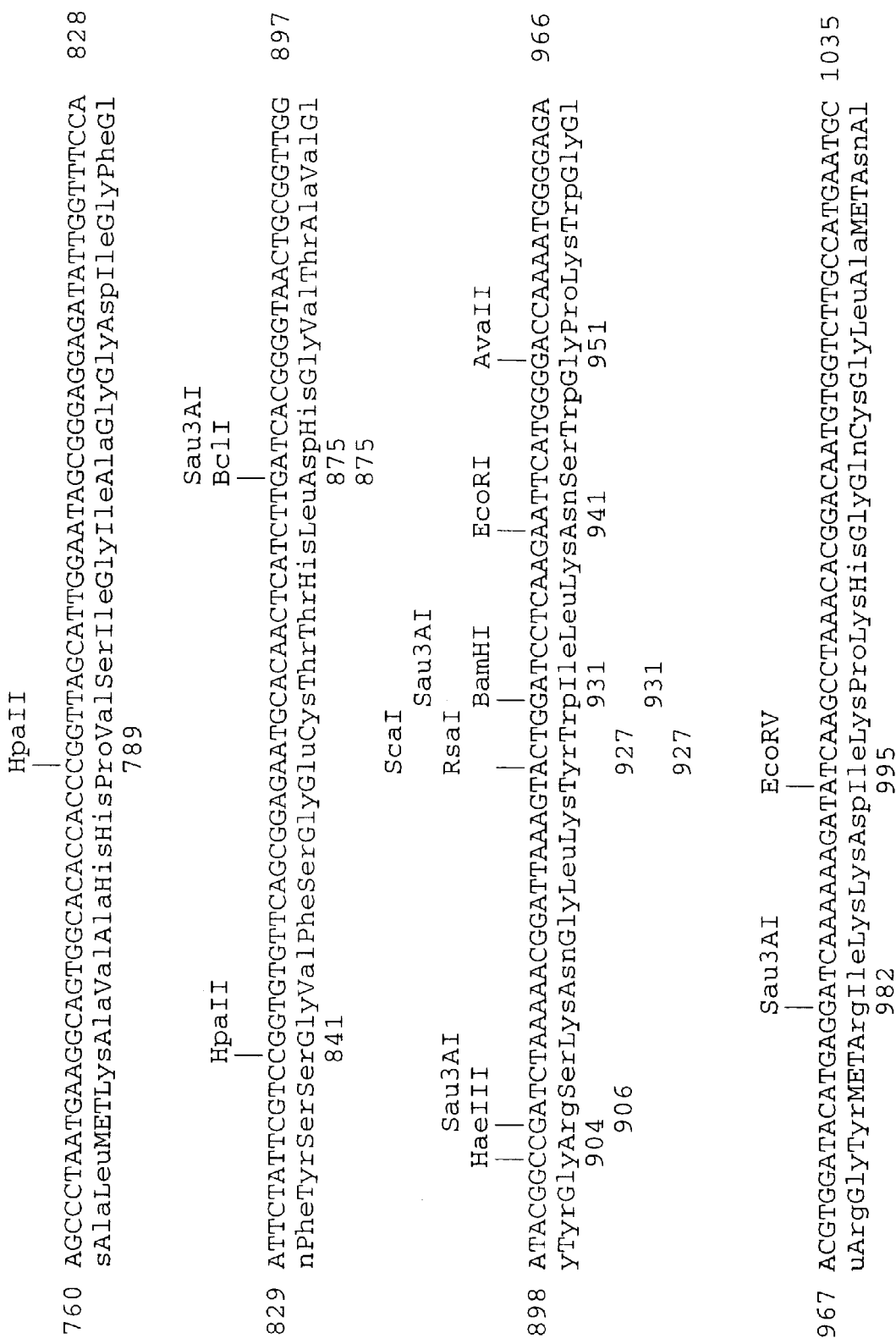

The restriction map and sequence of the EA9 cDNA clone have been determined (FIG. 4). Identification of a polyadenylation signal (Proudfoot and Brownlee, *Nature* (1976) 263:211–214) and of polyA tails at the 3'-end of EA9 indicated the orientation of the cDNA clone and the direction of transcription of the mRNA. The function of the encoded protein is unknown at this time.

EA9 s a member of a small gene family as shown by Southern blot analysis. DNA was isolated from *B. campestris* leaves (as described in Example I, Southern analysis), digested with either BamHI, BglII or BindIII and probed with a labeled fragment of EA9. Three fragments of genomic DNA hybridized in both BamHI and BGlII digests. Only 2 bands hybridized in the HindIII digest. The data suggests that the EA9 family comprises between one and three genes.

The sequence of EA9 is used to synthesize a probe which identifies a unique class of Brassica seed-specific genes from a genomic library in the manner described in Examples II and III. The regulatory sequences of these genes is used to construct an expression cassette similar to those described for the napin genes, with the EA9 construct directing seed coat specific expression of any gene inserted in it.

Example 6
Other Seed Specific Examples

Other seed-specific genes also can serve as useful sources of promoters. cDNA clones of cruciferin, the other major seed storage protein of *B. napus*, have been identified (Simon et. al., (1985) supra) and could be used to screen a genomic library for promoters. Without knowing the specific functions, yet other cDNA clones can be classified as to their level of expression in seed tissues, their timing of expression (i.e., when postanthesis they are expressed) and their approximate representation (copy number) in the *B. campestris* genome. Clones fitting the criteria necessary for expressing genes related to fatty acid synthesis or other seed functions can be used to screen a genomic library for genomic clones which contain the 5' and 3' regulatory regions necessary for expression. The non-coding regulatory regions can be manipulated to make a tissue-specific expression cassette in the general manner described for other genes in previous examples.

Example 7
Construction of Tomato Rive Fruit cDNA Bank and Screening for Fruit-Specific Clones Tomato plants (*Lycopersicon esculentum* cv UC82B) were grown under greenhouse conditions. Poly(A)$^+$RNA was isolated as described by Mansson et al., *Mol. Gen. Genet.* (1985) 200:356–361. The synthesis of cDNA from poly(A)$^{+RNA}$ prepared from ripe fruit, cloning into the PstI site of the plasmid pUC9 and transformation into an *E. coli* vector were all as described in Mansson et al., *Mol. Gen. Genet.* (1985) 200:356–361.

Library Screening

Two thousand recombinant clones were screened by colony hybridization with radiolabeled cDNA made from tomato red fruit mRNA, immature green fruit mRNA, and leaf MRNA. Bacterial colonies immobilized onto Gene-Screen Plus filters (New England Nuclear), were denatured in 1.5 M NaCl in 0.5 M NaOH, then neutralized in 1.5 M NaCl in 0.5 M Tris-HCl pH 8, and allowed to air dry. Hybridization, washing and autoradiography were all performed as described in Maniatis et al., Molecular Cloning: A Laboratory Manual (1982) Cold Spring Harbor, N.Y.

Sixty-five clones were selected which had more intense hybridization signals with fruit cDNA than with leaf cDNA and therefore appeared to be under-represented in the leaf MRNA population relative to the fruit population. Replicate slot blot filters were prepared using purified DNA from the selected clones and hybridized with radioactive cDNA from leaf, green fruit, and red fruit as before. This allowed selection of cDNA clone 2A11, also referred to as pCGN1299 which is on at high levels in both the fruit stages (red and green) and off in the leaf.

Example 8

Analysis of Clones

Synthesis of RNA Probes

The cDNA insert of pCGN1299 was excised as an EcoRI to HindIII fragment of approximately 600 bp (as measured on an agarose gel), and subcloned into the Riboprobe vector pGEM1 (Promega Biotec), creating pCGN488. $^{32}$P-labeled transcripts made from each strand of the pCGN488 insert using either SP6 or T7 polymerase were used as probes in separate Northern blots containing MRNA from leaf, immature green and mature red fruits. The RNA transcript from the SP6 promoter did not hybridize to the tomato mRNA. However, the transcript from the T7 promoter hybridized to an MRNA of approximately 700 nt in length from the green fruit and the red fruit but not to mRNA from tomato leaf. The direction of transcription of the corresponding mRNA was thus determined.

The tissue specificity of the pCGN1299 cDNA was demonstrated as follows. RNA from root, stem, leaf, and seven stages of fruit development (immature green, mature green, breaker, turning, pink, light red, and red) was sized on formaldehyde/agarose gels according to the method described by Maniatis et al., (1982), immobilized on nitrocellulose and hybridized to $^{32}$p-labeled RNA which was synthesized in vitro from pCGN488 using T7 polymerase. Each lane contained 100 ng of polyA$^+$ RNA except for two lanes (pink and light red lanes) which contained 10 µg of total RNA. The Northern analysis of mRNA from toot, stem, leaf, and various stages of fruit development indicated that pCGN1299 cDNA was expressed in all stages of fruit development from the early stages immediately after anthesis to red ripe fruit. No mRNA hybridizing to pCGN1299 was found in leaf, stem, or root tissue. The size of the mRNA species hybridizing to the pCGN488 probe was approximately 700 nt.

Message abundance corresponding to the pCGN1299 cDNA was determined by comparing the hybridization intensity of a known amount of RNA synthesized in vitro from pCGN488 using SP6 polymerase to mRNA from red tomato fruit in a Northern blot. The $^{32}$p-labeled transcript from pCGN488 synthesized in vitro using T7 polymerase was used as a probe. The Northern analysis was compared to standards which indicated that the pCGN1299 cDNA represents an abundant mRNA class in tomato fruit, being approximately 1% of the message.

Example 9

Sequencing of pCGN1299 and pCGN1298 cDNA Clones

DNA Sequencing

The polyA$^+$ sequence was missing from pCGN1299 cDNA. A longer cDNA clone, pCGN1298, therefore was identified by its hybridization with the pCGN488 probe. The complete DNA sequence of the two cDNA inserts was determined using both Maxam-Gilbert and the Sanger dideoxy techniques and is as follows. The sequence of pCGN1298 contains additional sequences at both the 5' and 3' end compared to pCGN1299. As shown in FIG. 8, the sequences are identical over the region that the two clones have in common.

Amino Acid Sequence

The pCGN1299 cDNA sequence was translated in three frames. The longest open reading frame (which starts from the first ATG) is indicated. Both pCGN1299 and pCGN1298 have an open reading frame which encodes a 96 amino acid polypeptide (see FIG. 8). The protein has a hydrophobic N-terminus which may indicate a leader peptide for protein targeting. A hydrophobicity profile was calculated using the Hopp and Woods, (*Proc. Natl. Acad. Sci. USA* (1981) 78:3824–3828) algorithm. Residues 10–23 have an extremely hydrophobic region. A comparison of 2A11 to pea storage proteins and other abundant storage proteins is shown in FIG. 6. The sulfur-rich composite of the fruit-specific protein is similar to a pea storage protein which has recently been described (see Higgins et al., *J. Biol. Chem.* (1986) 261:11124–11130, for references to the individual peptides). This may indicate a storage role for this fruit-specific protein abundant species.

Example 10

Screening Genomic Library for Genomic Clones

Southern Hybridization

Southern analysis was performed as described by Maniatis et al., 1982. Total tomato DNA from cultivar UC82B was digested with EcoRI or HindIII, separated by agarose gel electrophoresis and transferred to nitrocellulose. Southern hybridization was performed using a $^{32}$p-labeled probe produced by nick translation of pCGN488 (Maniatis et al., 1982). The simple hybridization pattern indicated that the gene encoding pCGN1299 cDNA was present in a few or perhaps even one copy in a tomato genome.

Isolation of a Genomic Clone

A genomic library established in Charon35/Sau3A constructed from DNA of the tomato cultivar VFNT-Cherry was screened using the [$^{32}$P-]-RNA from cDNA clone pCGN488 as a probe. A genomic clone containing approximately 12.5 kb of sequence from the tomato genome was isolated. The region which hybridizes to a pCGN488 probe spans an XbaI restriction site which was found in the cDNA sequence and includes the transcriptional initiation region designated 2A11.

Sequence of Genomic Clone

The DNA sequence of the genomic clone was determined by Sanger dideoxy techniques and is as shown in FIG. 7. The sequence of the genomic clone is identical to the pCGN1299 cDNA clone over the region they have in common.

Subcloning

The region surrounding the XbaI restriction site, approximately 2.4 kb in the 5' direction and approximately 2.1 kb in the 3' direction was subcloned to provide an expression cassette. The 5' XhoI to XbaI fragment and the 3' XbaI to EcoRI fragment from the 2A11 genomic clone were inserted into a pUC-derived chloromphenicol plasmid containing a unique XhoI site and no XbaI site. This promoter cassette plasmid is called pCGN1273.

Example 11

Construction of Fruit-Specific Antisense Cassette

Insertion of Antisense Fragment

The 2A11 genomic fragment was tagged with PG antisense sequences by insertion of PG into the unique XbaI site of the pCGN1273 promoter cassette in the antisense orientation. The inserted sequences increased the size of the mRNA over the endogenous transcript, and thus the expression pattern of the construct could be compared to the endogenous gene by a single Northern hybridization in a manner analogous to the detection of a tuber-specific potato gene described by Eckes et al., *Mol. Gen. Genet.* 1986 205:14–22.

Example 12

Insertion of Tagged Genomic Construction Into Agrobacterium Binary Vectors

The tagged genomic construction is excised using the flanking XhoI restriction enzyme sites and is cloned into the unique SalI site of the binary plasmid pCGN783 (see Example 2 for construction) containing a plant kanamycin resistance marker between the left and right borders to provide plasmid pCGN1269.

This plasmid binary vector in *E. coli* C2110 is conjugated into *A. tumefaciens* containing a disarmed Ti-plasmid capable of transferring the polygalacturonase antisense cassette and the kanamycin resistance cassette into the plant host genome.

The Agrobacterium system which is employed is *A. tumefaciens* PC2760 (G. Ooms et al., *Plasmid* (1982) 7:15–29; Hoekema et al., *Nature* (1983) 303:179–181; European Pat. Application 84-200239.6, 2424183).

Example 13

Transfer of Genomic Construction to Tomato via Cocultivation

Substantially sterile tomato cotyledon tissue is obtained from seedlings which have been grown at 24° C., with a 16 hr/8 hr day/night cycle in 100×25 mm petri dishes containing Murashige-Skoog salt medium and 0.8% agar (pH 6.0). Any tomato species may be used, however, here the inbred breeding line was UC82B, available from the Department of Vegetable Crops, University of California, Davis, Calif. 95616. The cotyledons are cut into three sections and the middle placed onto feeder plates for a 24-hour preincubation. The feeder plates are prepared by pipetting 0.5 ml of a tobacco suspension culture ($10^6$ cells/ml) onto 0.8% agar medium, containing Murashige minimal organic medium (K.C. Biologicals), 2,4-D (0.1 mg/l), kinetin (1 mg/l), thiamine (0.9 mg./l) and potassium acid phosphate (200 mg/l, pH 5.5). The feeder plates are prepared two days prior t use. A sterile 3 mm filter paper disk containing feeder medium is placed on top of the tobacco cells after the suspension cells are grown for two days.

Following the preincubation period, the middle one third of the cotyledon sections are placed into a liquid MG/L broth culture (1–5 ml) of the *A. tumefaciens* strain. The binary plasmid pCGN1269 is transferred to *A. tumefaciens* strain 2760 by conjugation or by transformation selecting for Gentamicin resistance encoded by the plasmid pCGN1269. The cotyledon sections are cocultivated with the bacteria for 48 hrs. on the feeder plates and then transferred to regeneration medium containing 500 mg/l carbenicillin and 100 mg/l kanamycin. The regeneration medium is a K.C. Biologicals Murashige-Skoog salts medium with zeatin (2 mg/l) myo-inositol (100 mg/l), sucrose (20 g/l), Nitsch vitamins and containing 0/8% agar (pH 6.0). In 2–3 weeks, shoots are observed to develop. When the shoots are approximately 1.25 cm, they are excised and transferred to a Murashige and Skoog medium containing carbenicillin (500 mg/l) and kanamycin (50 mg/l) for rooting. Roots develop within 10–12 days.

Shoots which develop and subsequently root on media containing the kanamycin are tested for APH3'II enzyme.

An aminoglycoside phosphotransferase enzyme (APH3'II) assay is conducted on putative transformed tomato plants and shoots. APH3'II confers resistance to kanamycin and neomycin. APH3'II's activity is assayed (Reiss et al., *Gene* (1984) 30:211–218) employing electrophoretic separation of the enzyme from other interfering proteins and detection of its enzymatic activity by in situ phosphorylation of kanamycin. Both kanamycin and [$\gamma^{-32}$P] ATP act as substrates and are embedded in an agarose gel which is placed on top of the polyacrylamide gel containing the proteins. After the enzymatic reaction, the phosphorylated kanamycin is transferred to P-81 phosphocellulose ion exchange paper and the radiolabeled kanamycin is finally visualized by autoradiography. The Reiss et al., method is modified in the final washing of the P-81 ion exchange paper by rinsing in 0.1 mg/ml of proteinase K.

Example 14

Construction of Tagged 2A11 Plasmids In Binary Vectors

The compete sequence of the 2A11 genomic DNA cloned into pCGN1273 from the XhoI site (position 1 at the 5' end) to the EcoRI site (position 4654) is shown in FIG. 7. pCGN1267 was constructed by deleting from pCGN1273 a portion of the plasmid polylinker from the EcoRV site to the BamHI site. Two DNA sequences were inserted into pCGN1273 at the unique XbaI site (position 2494). This site is in the 3' non-coding region of the 2A11 genomic clone before the poly A site.

pCGN1273 was tagged with 360 bp (from base number 1 to 360) from the 5' region of the tomato polygalacturonase (PG) cDNA clone, F1 (Sheehy et al., *Mol. Gen. Genet.* (1987) 208:30–36) at the unique XbaI restriction enzyme site. The tag was inserted in the antisense orientation resulting in plasmid pCGN1271 and in the sense orientation yielding plasmid pCGN1270. Each plasmid was linearized at the unique BglII restriction enzyme site and cloned into the binary vector pCGN783 at the unique BamHI restriction enzyme site.

pCGN1273 was also tagged with a 0.5 kb fragment of DNA (base number 1626 to 2115) from a PG genomic clone (see FIG. 8) which spans the 5' end of intron/exon junction. This fragment was cloned into the XbaI site resulting in plasmid pCGN1215. pCGN1215 was linearized at the unique BglII site and cloned into pCGN783 at the BamHI site resulting in two plasmids, pCGN1219 and pCGN1220, which differ only in the orientation of pCGN1215 within pCGN783.

Three DNA sequences were inserted into pCGN1267 at the unique restriction enzyme sites (position 2402, 2406). These sites are in the 3' non-coding region of the 2A11 genomic clone, 21 bp from the stop codon. The 383 bp XbaI fragment from the PG cDNA clone was cloned into the ClaI site of pCGN1267 after filling in the XbaI and ClaI ends with Klenow and blunt ligation. The fragment in a sense orientation resulted in plasmid pCGN1263 and in the antisense orientation gave pCGN1262. pCGN1263 was linearized at the unique BglII site and cloned into pCGN783 at the BamHI site yielding pCGN1260. pCGN1262 was also linearized at the BglII site and cloned into pCGN783 at the BamHI site resulting in two plasmids, pCGN1255 and pCGN1258, which differ only in the orientation of pCGN1262 in the binary vector pCGN783.

The 0.5 kb fragment of the PG genomic clone spanning the intron/exon junction (supra) was cloned into pCGN1267 at the ClaI site in an antisense direction yielding plasmid pCGN1225. This plasmid was linearized at the BglII restriction enzyme site and cloned in to pCGN783 at the BamHI site producing two plasmids, pCGN1227 and pCGN1228, which differ only in the orientation of pCGN1225 in the binary vector.

The Eco7 fragment (base numbers 5545 to 12,823) (Barker et al., *Plant Mol. Biol.* (1983) 2:335–350) from the octopine plasmid pTiA6 of *A. tumefaciens* (Knauf and Nester, *Plasmid* (1982) 8:45–54) was subcloned into pUC19 at the EcoRI site resulting in plasmid pCGN71. A RsaI digest allowed a fragment of DNA from bases 8487 to 9036 of the Eco7 fragment to be subcloned into the vector m13 BlueScript Minus (Stratagene, Inc.) at the SmaI site resulting in plasmid pCGN1278. This fragment contains the coding region of the genetic locus designated tmr which encodes a dimethylallyl transferase (isopentenyl transferase) (Akiyoshi et al., *Proc. Natl. Acad. Sci. USA* (1984) 81:5994–5998; Barry et al., ibid (1984) 81:4776–4780). An exonuclease/mung bean treatment (Promega Biotech) produced a deletion on the 5' end of the tmr gene to a point 39 base pairs 5' of the start codon. The tmr gene from pCGN1272 was subcloned into the ClaI site of pCGN1267. The tmr gene in the sense orientation yielded pCGN1261 and in the antisense orientation gave plasmid pCGN1266. pCGN1261 was linearized at the BglII site and cloned into pCGN783 at the BamHI site resulting in plasmid pCGN1254. pCGN1266 was also linearized at the BglII site and subcloned into pCGN783 at the BamHI site yielding two plasmids, pCGN1264 and pCGN1265, which differ only in the orientation of pCGN1266 in pCGN783.

Analysis of Expression in Transgenic Plants

Immature green fruit (approximately 3.2 cm in length) was harvested from two tomato plants cv. UC82B that had been transformed with a disarmed Agrobacterium strain containing pCGN1264. Transgenic plants are designated 12641-1 and 1264-11. The pericarp from two fruits of each plant was ground to a powder under liquid $N_2$, total RNA extracted and polyA$^+$ mRNA isolated (as described in Mansson et al., *Mol. Gen. Genet.* (1985) 200:356–361). Young green leaves were also harvested from each plant and polyA$^+$ mRNA isolated.

Approximately 19 μg of total RNA from fruit, 70 ng of polyA$^+$ mRNA from fruit and 70 ng of polyA$^+$ mRNA from leaves from transformed plants 1264-1 and 1264-11 was run on a 0.7% agarose formaldehyde Northern gel and blotted onto nitrocellulose (Maniatis et al., Molecular Cloning: A Laboratory Manual (1982) Cold Spring Harbor, N.Y.). Also included on the gel as a negative control was approximately 50 ng of polyA$^+$ mRNA from leaf and immature green fruit of a nontransformed UC82B plant.

As a positive control and to help in quantitating mRNA levels, in vitro transcribed RNA from pCGN1272 was synthesized using T3 polymerase (Stratagene, Inc.). Nineteen pg and 1.9 pg of this in vitro synthesized RNA were loaded on the Northern gel.

The probe for the Northern filter was the 1.0 kb tmr insert DNA (a KpnI to SAcI fragment) from pCGN1272 isolated by electroelution from an agarose gel (Maniatis, supra (1982)) and labeled by nick translation (Bethesda Research Laboratory kit) using $\alpha^{32}$P dCTP (Amershan).

The Northern filter was prehybridized at 42° C. for 5 hrs. in the following solution: 25 ml formamide, 12.5 ml 20× SSC, 2.5 ml 1 M NaP, 5 ml 50× Denhardts, 0.5 ml 10% SDS, 1 ml 250 mM EDTA, 1 ml 10 mg/ml ssDNA and 2 ml $H_2O$. Then one-fifth volume of 50% dextran sulfate and approximately $2.2 \times 10^7$ cpm of the probe was added and hybridization was for 15 hrs. at 42° C.

The Northern filter was washed one time in 2× SSC and 0.1% SDS at 55° for 20 minutes each wash. The filter was allowed to air dry before being placed with Kodak XAR film and an intensifying screen at $^-70°$ for two days.

Northern Results on Transgenic Plants

The nicked tmr probe hybridized with a mRNA species approximately 1.7 kb in length was observed in the total RNA and polyA$^+$ mRNA fruit lanes of the Northern blot. This is the expected length of the reintroduced 2A11 gene (0.7 kb) tagged with the tmr gene (1.0 kb) in the antisense orientation. The level of expression from the reintroduced tagged gene is somewhat lower than the level of expression of the endogenous 2A11 gene. The level of expression of the reintroduced gene in immature green fruit is higher than the expression level in leaf tissue with a small amount of hybridizing mRNA in leaf tissue in these transformants.

Example 15

Different Sized 2A11 5' Regions

The design of the 2A11 cassette is shown in FIG. 9. The cassette contains 3.8 kb of DNA 5' of the transcriptional start site and the entire 3' region (from the TGA stop codon to a site 2.0 kb 3' of the poly A addition site.) of the 2A11 gene. FIG. 7 shows the restriction sites and indicates (below the representation of the gene) the regions of the 2A11 gene used to construct the 2A11 cassette. The 2A11 cassette was constructed as follows.

Transcriptional Initiation Region

The 5' end of the 2A11 cassette was constructed starting with an EcoRI subclone genomic clone as described in application PCTUS88/01811 cloned into the EcoRI of Bluescript (+) (Stratagene) resulting in pCGN1288. This clone contains sequences from the EcoRI site at position 1651 in the intron of the 2A11 gene to the EcoRI site located 2.5 Kb upstream of the XhoI site at position 1 of the sequenced region (see FIG. 7). The XHOI fragment from position 1 of the sequenced region to the XHOI site in the Bluescript polylinker was deleted creating plasmid pCGN2004 which contain the 2A11 region from position 1 to position 1651. The coding region of 2A11 was deleted by treating this plasmid with ExonucleaseIII/S1 using the commercially available Erase-a-Base Kit (Promega Biotec) and sequencing deletion plasmids until one was found which had the coding region deleted to position 1366. The resulting plasmid, pCGN1251, had the genomic region from the XhoI site (position 1) to position 1366. The EcoRI fragment of pCGN1288 was then transferred to a chloramphenicol resistant plasmid vector, pCGN2015, to make pCGN1231. pCGN2015 is a Cm resistant derivative of the Bluescript plasmid. A BstEII/BamHI fragment of pCGN1251 was then transferred into BstEII/BamHI digested pCGN1231 to make pCGN1235 which contains the region from the EcoRI site (2.5 kb upstream of the sequenced region) to position 1366 of the sequenced region flanked by the Bluescript polylinker in a Cm resistant vector.

Transcriptional and Translational Termination Region

The 3' end of the 2A11 cassette was constructed from pCGN1273 (described in application PCT/US8801811) by digesting the plasmid with PvuI and EcoRI, isolating the 2249 bp insert (from position 2402 to 4653), ligating with a double-stranded oligonucleotide containing the sequence shown in FIG. 7 from the BamHI sticky end to a PvuI sticky end into a Bluescript vector which had been digested with BamHI and EcoRI. The resulting plasmid, pCGN1238, contains the 3' end of the 2A11 gene from the stop codon at position 2381 to the EcoRI site at position 4653.

Final Construction

Several versions of the 2A11 cassette in different vectors with different flanking restriction sites have been constructed; maps of the plasmids are shown in FIG. 10.

A cassette containing the 5' and 3' regions of the 2A11 gene was constructed by ligating the BamHI to EcoRI insert of pCGN1238 into pCGN1235 which had been digested with BamHI and XbaI (the XbaI site having been filled in with Klenow polymerase to make a blunt-ended fragment). The resulting plasmid, pCGN1240, has the 5' end of the 2A11 gene from the EcoRI site 2.5 kb upstream of the XhoI site (position 1) to position 1366 (which is located between the transcriptional initiation site of the 2A11 gene and the ATG), followed by a polylinker region with sites for SmaI, BamHI, PstI and SalI which can be conveniently used to insert genes followed by the 3' region from position 2381 to 4653. The plasmid backbone of pCGN1240 is the Bluescript cm plasmid described above.

Construction of Plasmid pCGN1241

A more convenient version has the EcoRI of pCGN1240 excised and inserted into a Bluescript vector called pCGN1239 which has an altered polylinker region such that the entire cassette can be excised as a SacI-KpnI fragment. The altered Bluescript vector, pCGN1239, was constructed by modifying the BlueScript polybinder from the SacI site to the KpnI site including a synthetic polylinker with the following sequence: AGCTCGGTACCGAATTC-GAGCTCGGTAC to create a polylinker with the following sites: SacI-KpnI-EcoRI SacI-KpnI. The EcoRI insert of pCGN1240 was inserted into pCGN1239 to make pCGN1241 (see FIG. 9).

Construction of pCGN2610 and pCGN2611

A chloramphenicol resistant version of the 2A11 promoter cassette was constructed by inserting the synthetic polylinker described above (see construction of pCGN1241) into pCGN2015 to make pCGN1246, followed by insertion of the EcoRI fragment of pCGN1241 to make pCGN2610 and pCGN2611 which differ only by the orientation of the inserted fragment in the plasmid vector (see FIG. 8).

Example 16

Comparison of Expression from Different Sized 2A11 5' Regions

A beta-glucuronidase (Gus) reporter gene was used to evaluate the level of expression and tissue specificity of various 2A11-Gus constructions. Gus is a useful reporter gene in plant systems because it produces a highly stable enzyme, there is little or no background (endogenous) enzyme activity in plant tissues, and the enzyme is easily assayed using fluorescent or spectrophotometric substrates. See, for example, Jefferson *Plant Mol. Biol. Rep.* (1988) 5:387–405. Histochemical stains for Gus enzyme activity are also available which can be used to analyze the pattern of enzyme expression in transgenic plants. Jefferson (1988), supra.

Constructions containing 1.3 kb (short), 1.8 kb (intermediate length), or 3.8 kb (long) 2A11 5' sequences fused to the Gus reporter gene were prepared. In addition, constructions were prepared which have altered 3' ends. The altered 3' ends are either a shorter 2A11 3' end from tr5 of the T-DNA of the Ti plasmid (Willmitzer et al., *Embo. J.* (1982) 1:139–146; Willmitzer et al., *Cell* (1983) 42:1045–1056. The constructions were transferred to a binary vector (pCGN1578), and used in *A. Tumefaciens* cocultivations. The resulting binary was used to transform tomato plants. The transgenic plants obtained were fluorometrically analyzed for Gus enzyme activity.

Example 17

Screening Genomic Library for Polygalacturonase Genomic Clones

Isolation of a Genomic Clone

An EcoRI partial genomic library established in Charon 4 constructed from DNA of a *Lycopersicon esculentum* cultivar was screened using a probe from the polygalacturonase cDNA (Sheehy et al., *Mol. Gen. Genet.* (1987) 208:30–36). A lambda clone containing an approximately 16 kb insert was isolated from the library, of which an internal 2207 bp HindIII to EcoRI was sequenced. The HindIII-EcoRI fragment includes the polygalacturonse promoter region.

Sequence of Genomic Clone

The DNA sequence of the genomic clone was determined by Sanger dideoxy techniques and is as shown in FIG. 8. The sequence of the genomic clone bases 1427 to 1748 are homologous to the polygalacturonase cDNA sequence.

The above results demonstrate the ability to identify inducible regulatory sequences in a plant genome, isolate the sequences and manipulate them. In this way, the production of transcription cassettes and expression cassettes can be produced which allow for differentiated cell production of the desired product. Thus, the phenotype of a particular plant part may be modified, without requiring that the regulated product be produced in all tissues, which may result in various adverse effects on the growth, health, and production capabilities of the plant. Particularly, fruit-specific transcription initiation capability is provided for modifying the phenotypic properties of a variety of fruits to enhance properties of interest such as processing, organoleptin properties, storage, yield, or the like. Further, the results demonstrate one can use transcriptional initiation regions associated with the transcription of sequences in seeds in conjunction with sequences other than the normal sequence to produce endogenous or exogenous proteins or modulate the transcription of expression of nucleic acid sequences. In this manner, seeds can be used to produce novel products, to provide for improved protein compositions, to modify the distribution of fatty acid, and the like.

It is also evident from the above results that not only can soybean be transformed, so as to introduce heterologous genes, but transformed soybean cells may be regenerated into plants and the plants demonstrate the phenotype of the heterologous gene. In addition, native promoters can find use in conjunction with heterologous genes and retain their capability to be induced in the same manner as the native gene. Therefore, one can provide for regulated expression of a heterologous gene, where regulation may be by an external condition, such as light. Furthermore, Ti- or Ri-DNA may be employed for introducing the heterologous gene as part of an expression cassette into the soybean cell without formation of a tumor and the resulting cells grown in culture and plants regenerated from the cells. By appropriate choice of various genes, various properties of the cell may be enhanced by introduction of additional copies of a homologous gene or new phenotypes may be provided by expression of heterologous genes. In addition, mutated genes may be employed which can impart novel properties to the host cell, providing for host resistance to biocides, enhanced production of specific metabolites or products at the same or different times from the normal regulated expressions, or the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising as operably linked components in the direction of transcription, a promoter region obtainable from a gene selected from the group consisting of a napin gene, an EA9 gene and an acyl carrier protein gene; a DNA sequence of interest other than the native coding sequence of said gene; and a transcription termination region, wherein said components are functional in a plant cell, and wherein said DNA construct is flanked by T-DNA.

2. The DNA construct according to claim 1, wherein said DNA sequence of interest encodes an enzyme.

3. The DNA construct according to claim 1, wherein said DNA sequence of interest is an antisense sequence.

4. A plant cell having an altered phenotype as a result of expression of a DNA construct according to claim 1.

5. The plant cell according to claim 4, wherein said DNA construct is flanked by T-DNA.

6. The plant cell according to claim 5 wherein said plant cell is one from the group consisting of a soybean cell and rapeseed cell.

7. The plant cell according to claim 4, wherein said DNA sequence of interest encodes an enzyme.

8. The plant cell according to claim 4, wherein said DNA sequence of interest is an antisense sequence.

9. A plant comprising cells comprising a DNA construct according to any one of claims 1, 2 or 3.

10. The plant according to claim 9, wherein said plant is dicotyledonous.

11. Seed obtained from a plant according to claim 10.

12. Seed having a DNA construct according to claim 1.

13. The seed according to claim 12, wherein said seed is an oil seed or a grain seed.

14. The seed according to claim 12, wherein said seed is from a dicotyledonous plant.

15. The seed according to claim 14, wherein said seed is from a plant of the genus Brassica.

16. The seed according to claim 14, wherein said dicotyledonous plant is selected from the group consisting of cotton, soybean, safflower and sunflower.

* * * * *